US010772733B2

(12) United States Patent
Lintula et al.

(10) Patent No.: US 10,772,733 B2
(45) Date of Patent: Sep. 15, 2020

(54) IMPLANTS AND METHODS OF USE AND ASSEMBLY

(71) Applicant: Paragon 28, Inc., Englewood, CO (US)

(72) Inventors: Eric Lintula, Parker, CO (US); Albert Dacosta, Lone Tree, CO (US); Dimitri Protopsaltis, Memphis, TN (US); Thomas R. Williams, Bon Aqua, TN (US); Francis D. Barmes, Parker, CO (US); Naser Rahman, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 16/519,270

(22) Filed: Jul. 23, 2019

(65) Prior Publication Data

US 2019/0343562 A1 Nov. 14, 2019

Related U.S. Application Data

(63) Continuation of application No. PCT/US2019/020383, filed on Mar. 1, 2019.

(Continued)

(51) Int. Cl.

*A61F 2/42* (2006.01)
*A61B 17/56* (2006.01)

(52) U.S. Cl.

CPC ...... *A61F 2/4225* (2013.01); *A61B 2017/564* (2013.01); *A61F 2002/4228* (2013.01)

(58) Field of Classification Search

CPC ... A61B 17/86; A61B 17/8605; A61B 17/861; A61B 17/8615; A61B 17/862; A61B 17/8625; A61B 17/863; A61B 17/8635; A61B 17/864; A61B 17/8645; A61B 17/866; A61B 2017/564; A61F 2/42; A61F 2/4225; A61F 2/4241; A61F 2002/4228; A61F 2002/4233; A61F 2002/4238; A61F 2002/4243; A61F 2002/4251; A61F 2002/4256

See application file for complete search history.

(56) References Cited

U.S. PATENT DOCUMENTS 5,011,497 A * 4/1991 Persson ................ A61F 2/4241 623/23.41
8,529,611 B2 * 9/2013 Champagne .......... A61F 2/4225 606/328

(Continued)

FOREIGN PATENT DOCUMENTS

WO 2017147537 8/2017

OTHER PUBLICATIONS

International Search Report and Written Opinion issued in corresponding PCT Application No. PCT/US2019/020383, dated May 23, 2019, 11 pages.

*Primary Examiner* — Eric S Gibson
(74) *Attorney, Agent, or Firm* — Heslin Rothenberg Farley & Mesiti P.C.; Jacquelyn A. Graff, Esq.

(57) ABSTRACT

Implants, devices and methods for maintaining, correcting and/or fusing joint deformities are disclosed. The implant including a first member, a second member, and a coupling member with a first end and a second end, wherein the first end engages the first member and the second end engages the second member. Methods of using the implants for maintaining, correcting and/or fusing joint deformities are also disclosed.

56 Claims, 66 Drawing Sheets

Related U.S. Application Data

(60) Provisional application No. 62/805,942, filed on Feb. 14, 2019, provisional application No. 62/637,051, filed on Mar. 1, 2018.

(56) References Cited

U.S. PATENT DOCUMENTS

| | | | | |
|---|---|---|---|---|
| 9,044,287 | B2* | 6/2015 | Reed | A61B 17/8891 |
| 9,138,274 | B1 | 9/2015 | Biesinger | |
| 9,168,074 | B2* | 10/2015 | Prandi | A61B 17/7233 |
| 9,211,192 | B2* | 12/2015 | Stahl Wernersson | A61F 2/4241 |
| 9,474,561 | B2* | 10/2016 | Shemwell | A61B 17/7291 |
| 9,545,274 | B2* | 1/2017 | McCormick | A61B 17/7291 |
| 9,603,643 | B2* | 3/2017 | Reed | A61B 17/1682 |
| 9,724,139 | B2* | 8/2017 | McCormick | A61B 17/7291 |
| 9,724,140 | B2* | 8/2017 | McCormick | A61B 17/8883 |
| 9,744,048 | B2* | 8/2017 | Merle | A61F 2/4637 |
| 9,757,168 | B2* | 9/2017 | Seavey | A61B 17/8872 |
| 9,808,296 | B2* | 11/2017 | McCormick | A61B 17/7291 |
| 10,080,597 | B2* | 9/2018 | Shemwell | A61B 17/7283 |
| 2007/0270855 | A1* | 11/2007 | Partin | A61B 17/8685 606/279 |
| 2011/0004255 | A1* | 1/2011 | Weiner | A61B 17/7291 606/301 |
| 2011/0054545 | A1* | 3/2011 | Champagne | A61B 17/7225 606/301 |
| 2011/0082508 | A1 | 4/2011 | Reed | |
| 2011/0301653 | A1 | 12/2011 | Reed | |
| 2012/0065692 | A1* | 3/2012 | Champagne | A61B 17/888 606/311 |
| 2013/0131822 | A1 | 5/2013 | Lewis et al. | |
| 2013/0274814 | A1* | 10/2013 | Weiner | A61B 17/8875 606/301 |
| 2014/0163624 | A1 | 6/2014 | Siegal et al. | |
| 2015/0223942 | A1* | 8/2015 | Merle | A61F 2/4637 623/21.15 |
| 2016/0045324 | A1 | 2/2016 | Austin et al. | |
| 2016/0354074 | A1* | 12/2016 | Miller | A61B 17/863 |
| 2017/0065424 | A1* | 3/2017 | Lauf | A61F 2/4225 |
| 2017/0360489 | A1* | 12/2017 | Palmer | A61B 17/84 |
| 2019/0343562 | A1* | 11/2019 | Lintula | A61B 17/7225 |
| 2020/0038189 | A1* | 2/2020 | Williams | A61F 2/4225 |

* cited by examiner

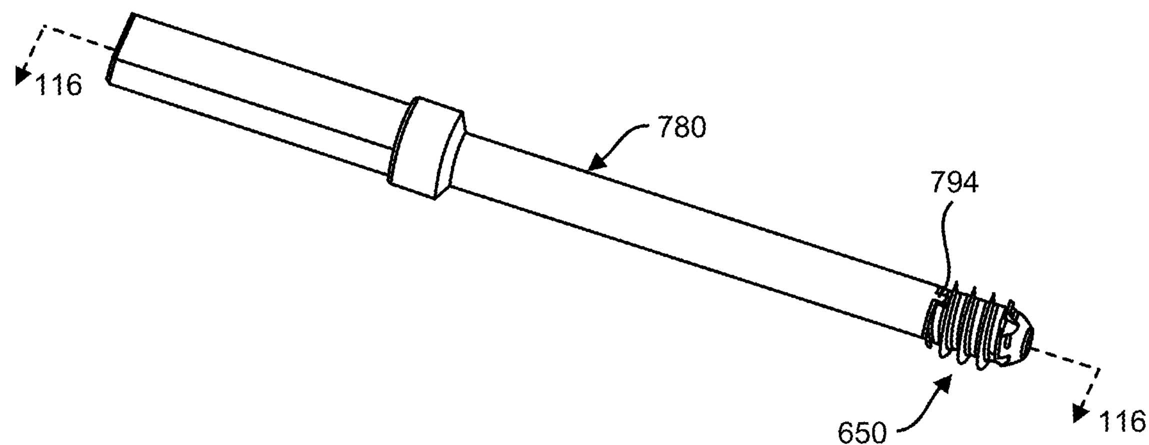
FIG. 114
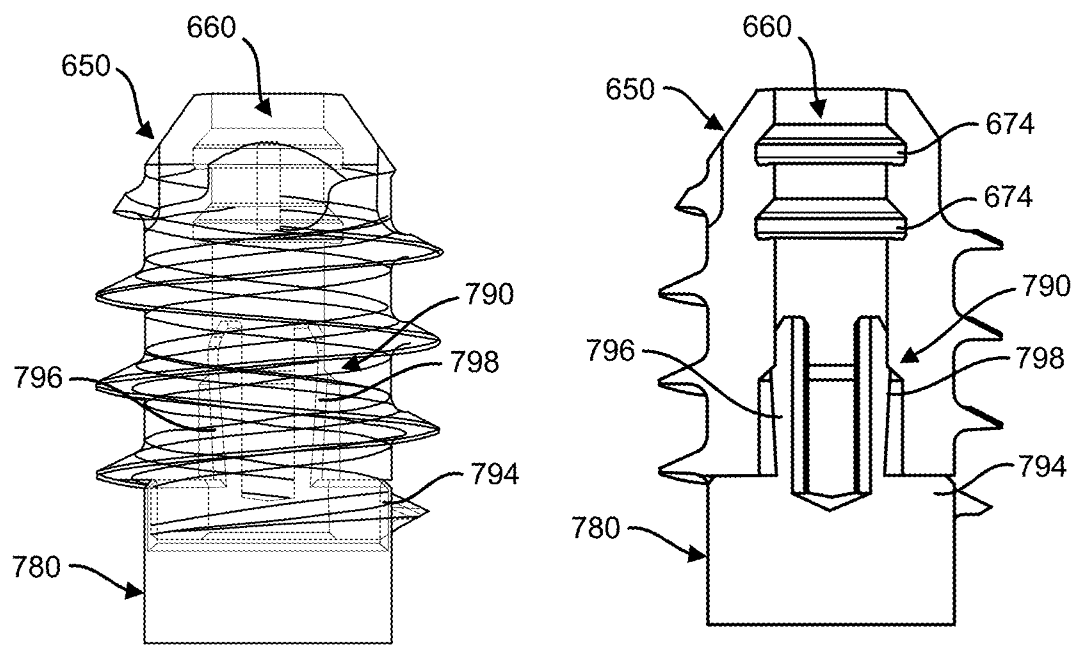
FIG. 115
FIG. 116

IMPLANTS AND METHODS OF USE AND ASSEMBLY

CROSS REFERENCE TO RELATED APPLICATIONS

This application is a continuation of PCT/US2019/020383 filed on Mar. 1, 2019 and entitled Implants and Methods of Use and Assembly, which claims priority benefit under 35 U.S.C. § 119(e) of U.S. provisional application No. 62/637,051 filed Mar. 1, 2018 and U.S. provisional application No. 62/805,942 filed Feb. 14, 2019, which are incorporated herein by reference in their entireties.

TECHNICAL FIELD

The present disclosure relates generally to general, podiatric, and orthopaedic surgery related to joint deformities. More specifically, but not exclusively, the present disclosure relates to implants, devices, and methods for maintaining, correcting and/or fusing joint deformities.

BACKGROUND OF THE INVENTION

Hammertoe is a foot deformity which may occur due to an imbalance in the muscles, tendons or ligaments of the toe. Currently available implants to correct the deformity rely on external compression during implantation. The compression applied during implantation is not maintained long-term resulting in a decrease in the loads across the joint after implantation.

Accordingly, it is an object of the present invention to overcome one or more of the above-described drawbacks and/or disadvantages of the currently used procedures. For example, in view of the deficiencies of the current implants, it would be desirable to develop implants, devices, and/or systems which maintain compression on the joint after implantation of the implant.

SUMMARY OF THE INVENTION

The present disclosure is directed toward implants, devices and methods for use in maintaining, correcting and/or fusing joint deformities.

In one aspect of the present disclosure provided herein, is an implant system. The implant system includes a first member, a second member, and a coupling member with a first end and a second end, wherein the first end engages the first member and the second end engages the second member In another aspect of the present disclosure provided herein, is a method for using the implant. The method includes obtaining an implant. The implant includes a first member, a second member, and a coupling member with a first end and a second end. The method also includes making an incision to expose a joint with a first bone and a second bone and preparing the bones for receiving the implant. The method further includes inserting the second member into the first bone and inserting the first end of the coupling member into the first member. In addition, the method includes inserting the first member with the engaged coupling member into the second bone and inserting a retention clip to engage the coupling member and the first member. Next, the method includes inserting the second end of the coupling member into the second member and removing the retention clip from engagement with the coupling member and the first member. Then, the method includes closing the incision.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 114 is a perspective view of a distal driver of the implant system of FIG. 69, in accordance with an aspect of the present disclosure;

FIG. 115 is an enlarged view of a portion of the distal driver of FIG. 114 engaging a transparent first member the implant of FIG. 69, in accordance with an aspect of the present disclosure;

FIG. 116 is a cross-sectional view of FIG. 115 taken along line 116-116 in FIG. 114, in accordance with an aspect of the present disclosure;

FIG. 119 is a perspective view of the proximal driver and retention clip of FIG. 117 with the proximal driver coupled to the coupling member of the implant system of FIG. 69, in accordance with an aspect of the present disclosure;

FIG. 120 is a perspective view of another implant system including the retention clip of FIG. 91, in accordance with an aspect of the present disclosure; and FIG. 121 is a side view of the implant system of FIG. 120, in accordance with an aspect of the present disclosure.

DETAILED DESCRIPTION FOR CARRYING OUT THE INVENTION

Figure 1:
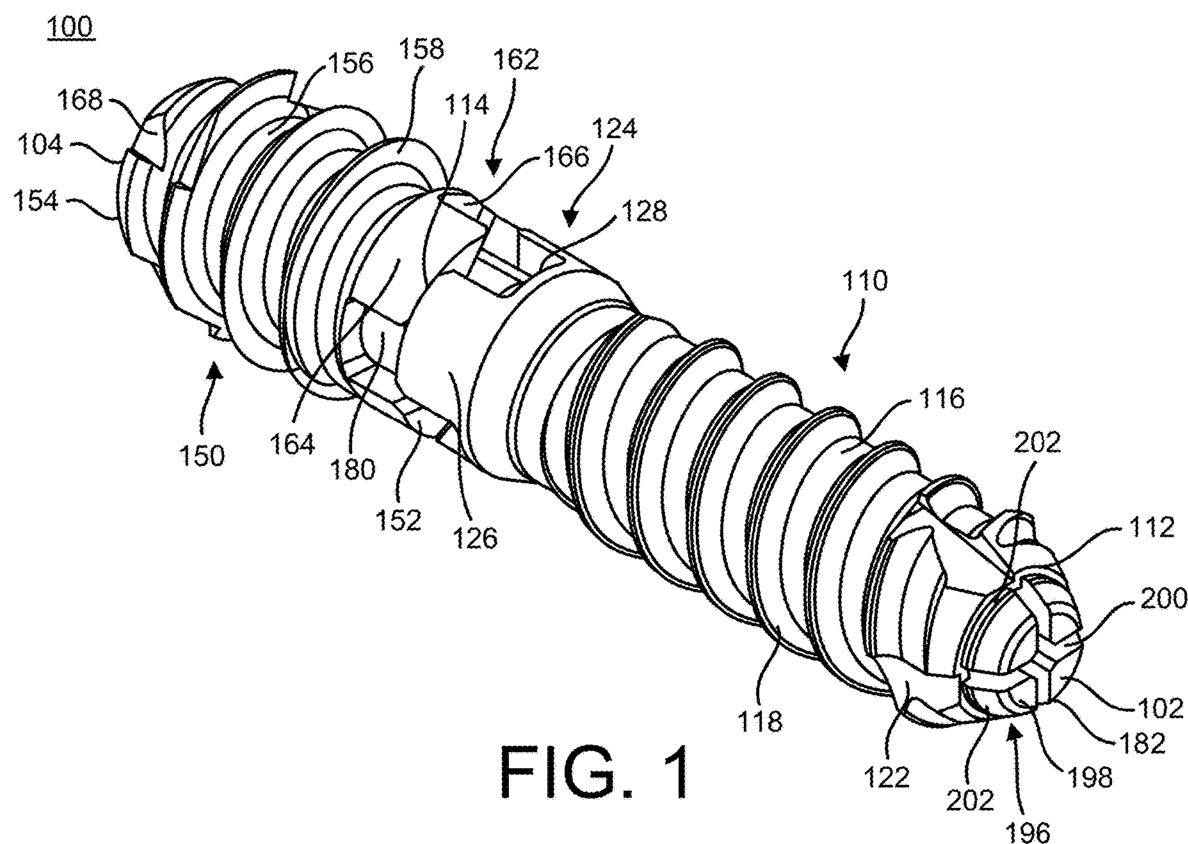
FIG. 1 is a first perspective view of one embodiment of an implant, in accordance with an aspect of the present disclosure.
Figure 2:
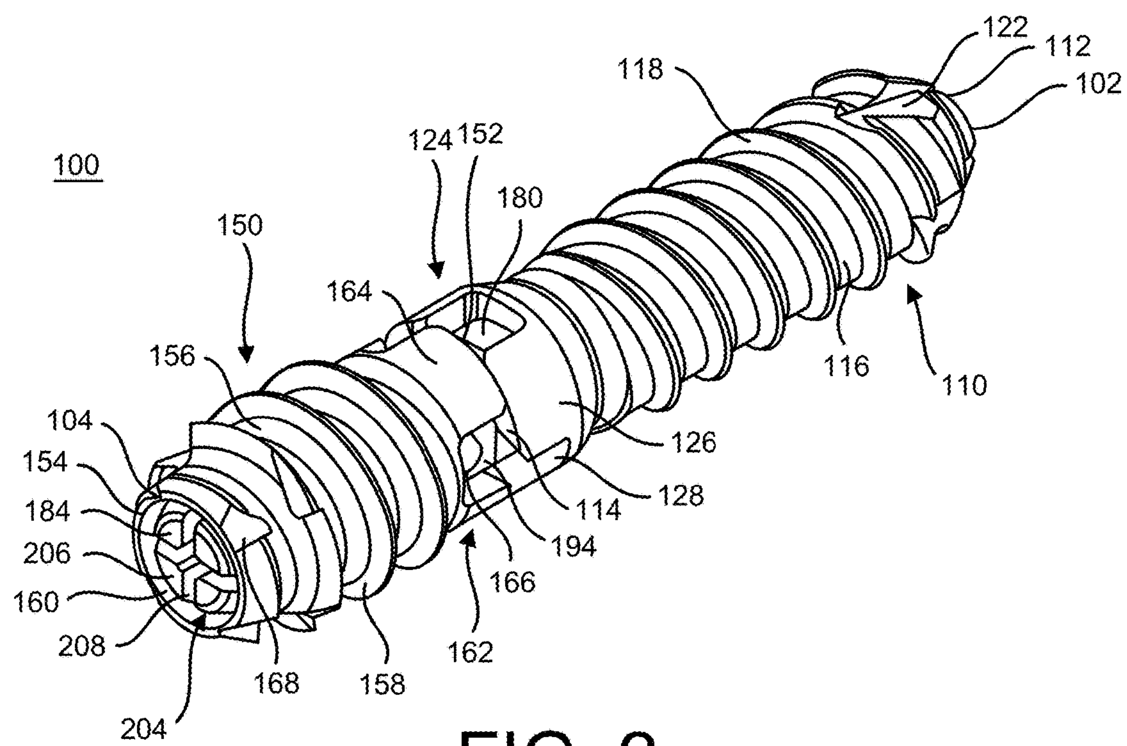
FIG. 2 is a second perspective view of the implant of FIG. 1, in accordance with an aspect of the present disclosure.
Figure 3:
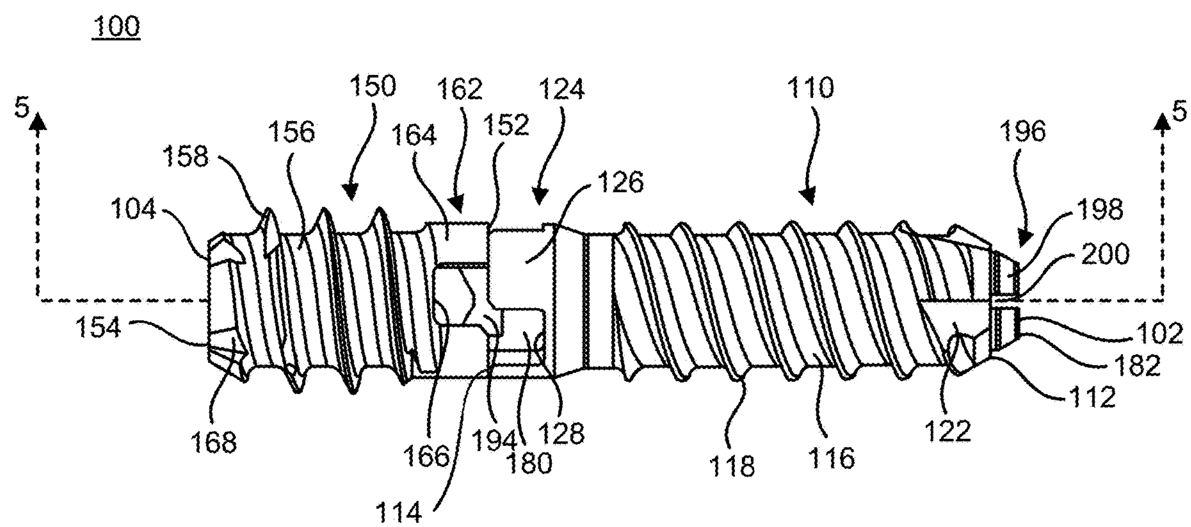
FIG. 3 is a first side view of the implant of FIG. 1, in accordance with an aspect of the present disclosure.
Figure 4:
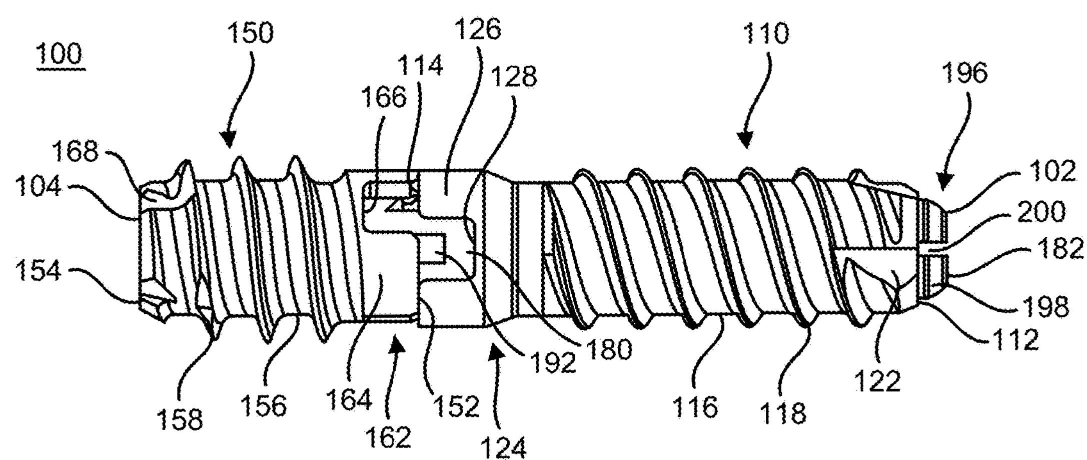
FIG. 4 is a second side view of the implant of FIG. 1, in accordance with an aspect of the present disclosure.

Generally stated, disclosed herein are devices, systems, and methods for maintaining, correcting and/or fusing joint deformities. Further, methods for using the devices and systems for maintaining, correcting and/or fusing joint deformities are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the foot, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right foot may be mirrored so that they likewise function with the left foot. Further, the devices, systems, instrumentation and methods, and the aspects, components, features and the like thereof, disclosed herein are described with respect to the foot for brevity purposes, but it should be understood that the devices, systems, instrumentation and methods may be used with other bones of the body having similar structures.

Referring to the drawings, wherein like reference numerals are used to indicate like or analogous components throughout the several views, and with particular reference to FIGS. 1-15, there is illustrated an implant 100. The implant 100 includes a first end 102 and a second end 104, as shown in FIGS. 1-5. The implant 100 also includes a first or proximal member 110, a second or distal member 150, and a coupling member 180 positioned to engage the first member 110 on one end and the second member 150 on another end. The implant 100 may be made of, for example, PEEK, titanium, stainless steel, nitinol or another similar biocompatible material, as known by one of ordinary skill in the art.

Figure 6:
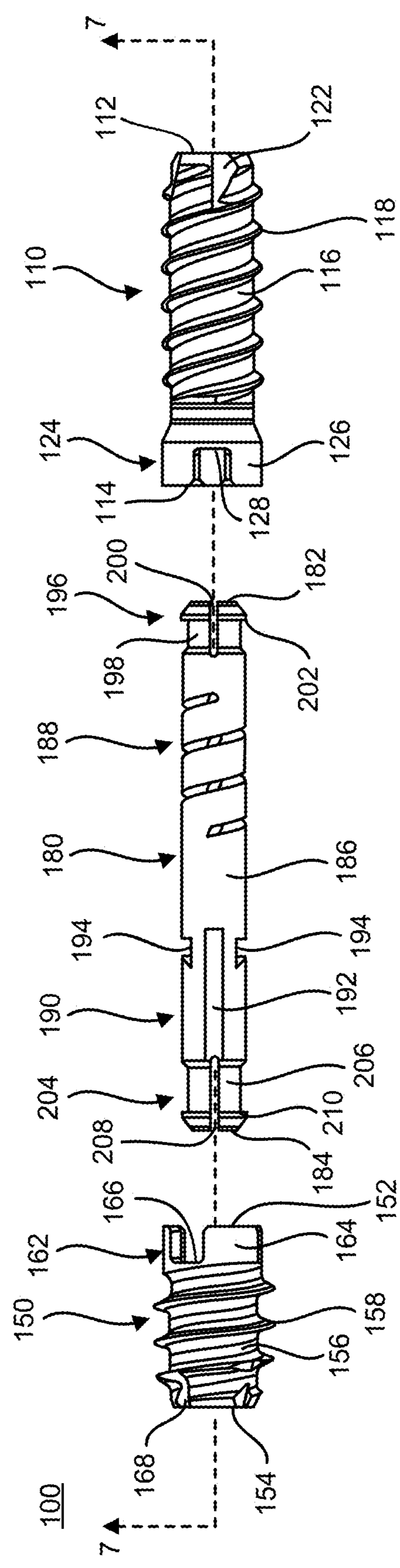
FIG. 6 is an exploded side view of the implant of FIG. 1, in accordance with an aspect of the present disclosure.
Figure 7:
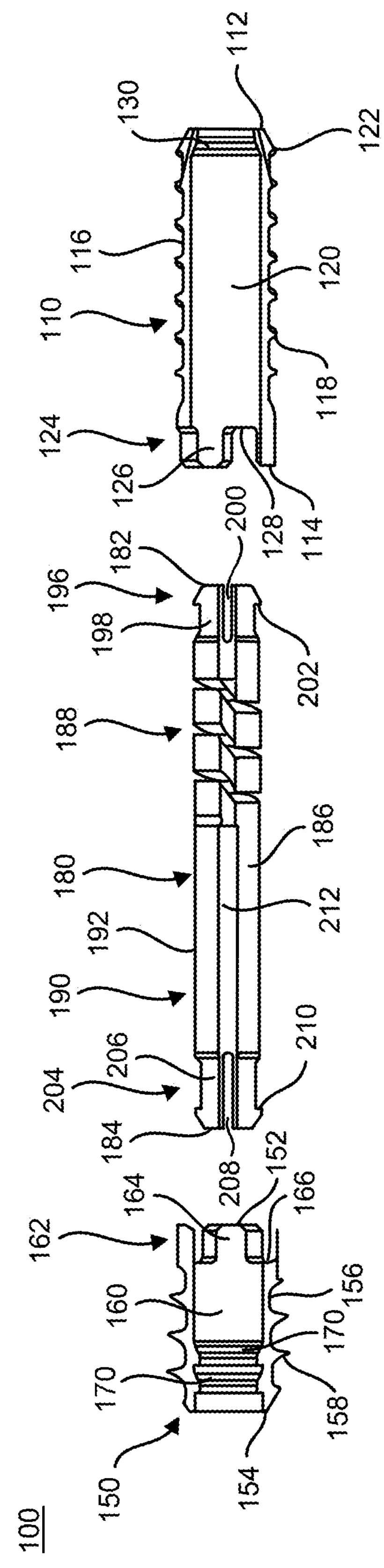
FIG. 7 is a cross-sectional view of the implant of FIG. 6 taken along line 7-7, in accordance with an aspect of the present disclosure.
Figure 8:
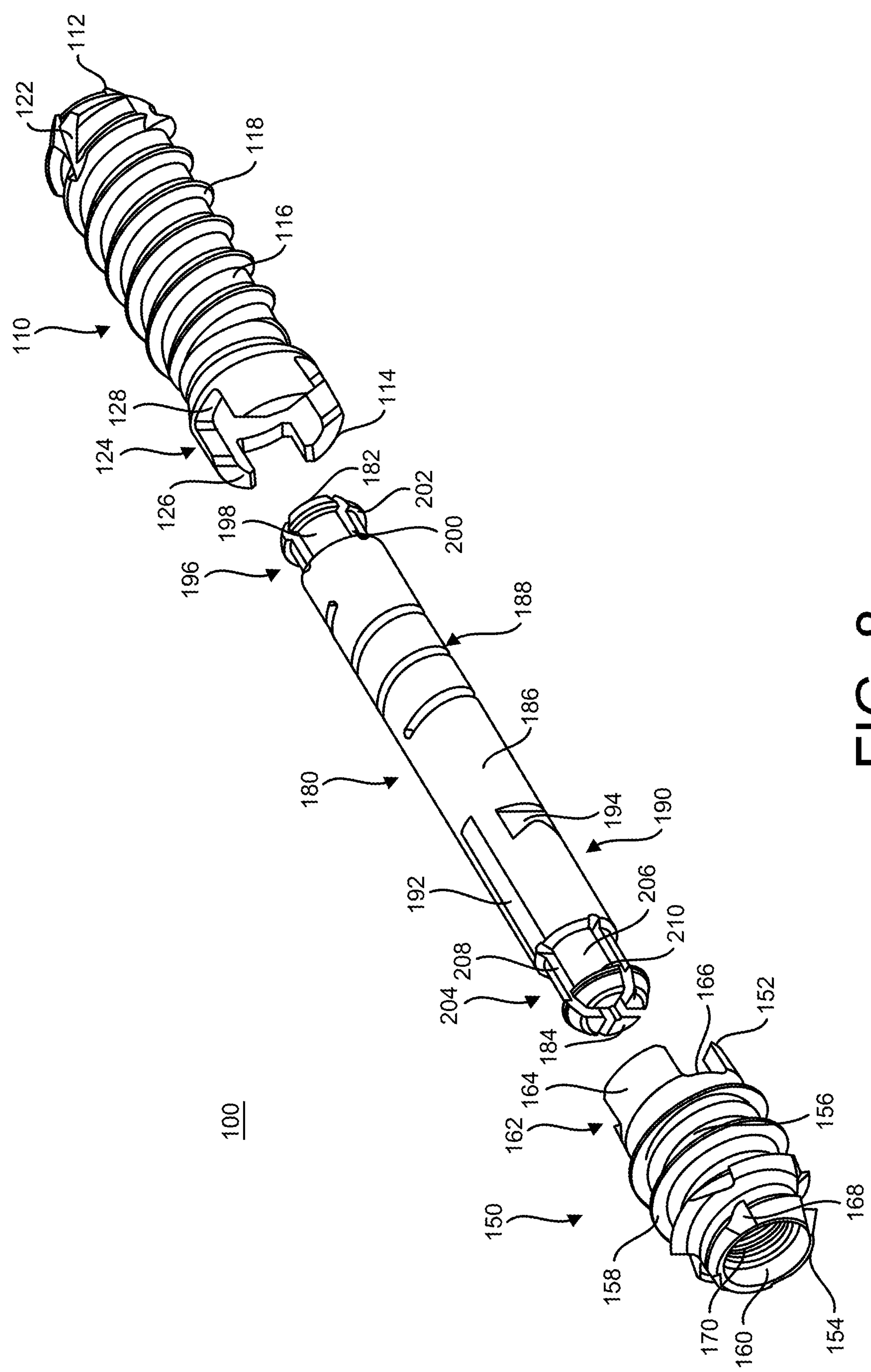
FIG. 8 is a first exploded perspective view of the implant of FIG. 1, in accordance with an aspect of the present disclosure.
Figure 9:
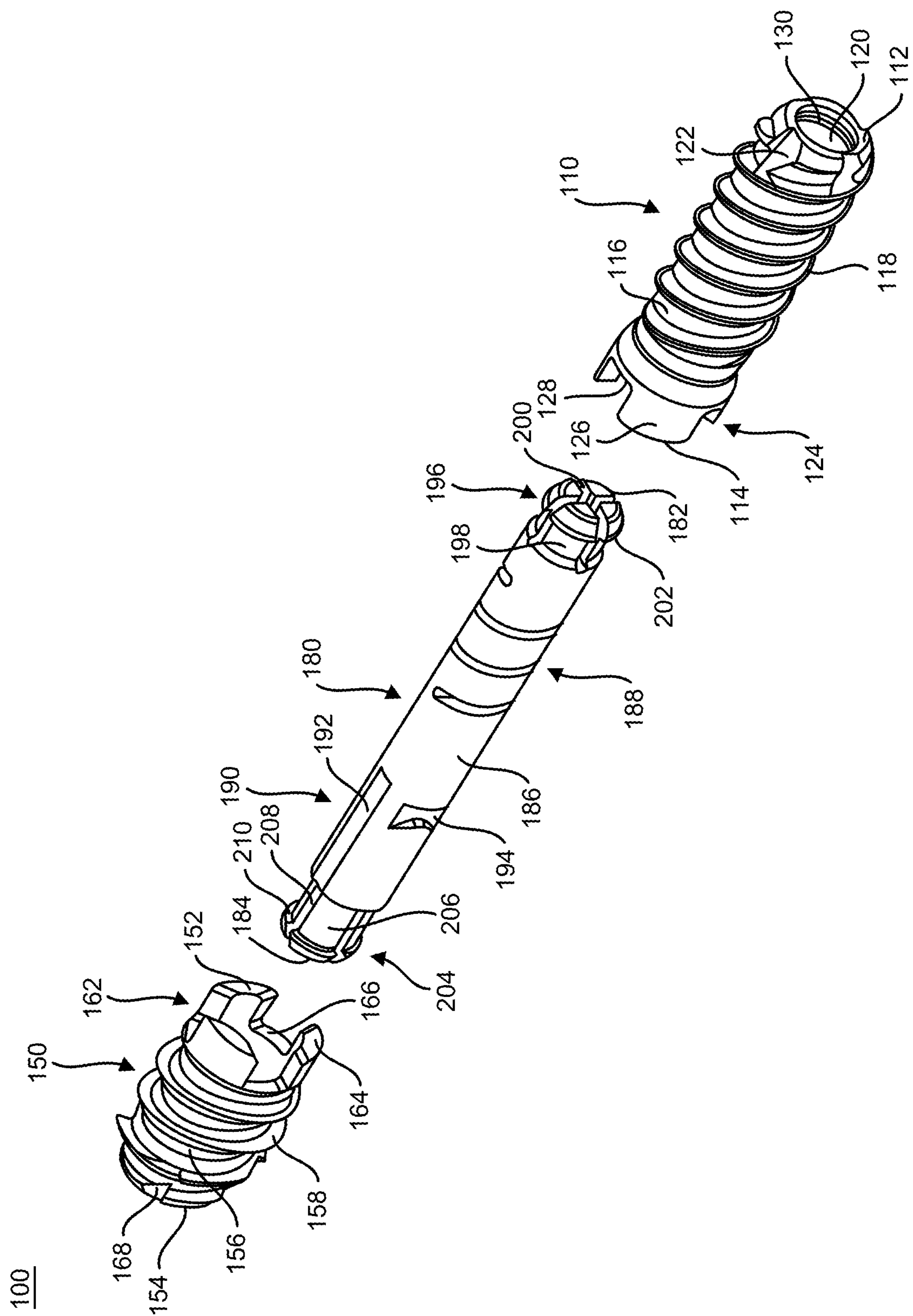
FIG. 9 is a second exploded perspective view of the implant of FIG. 1, in accordance with an aspect of the present disclosure.
Figure 10:
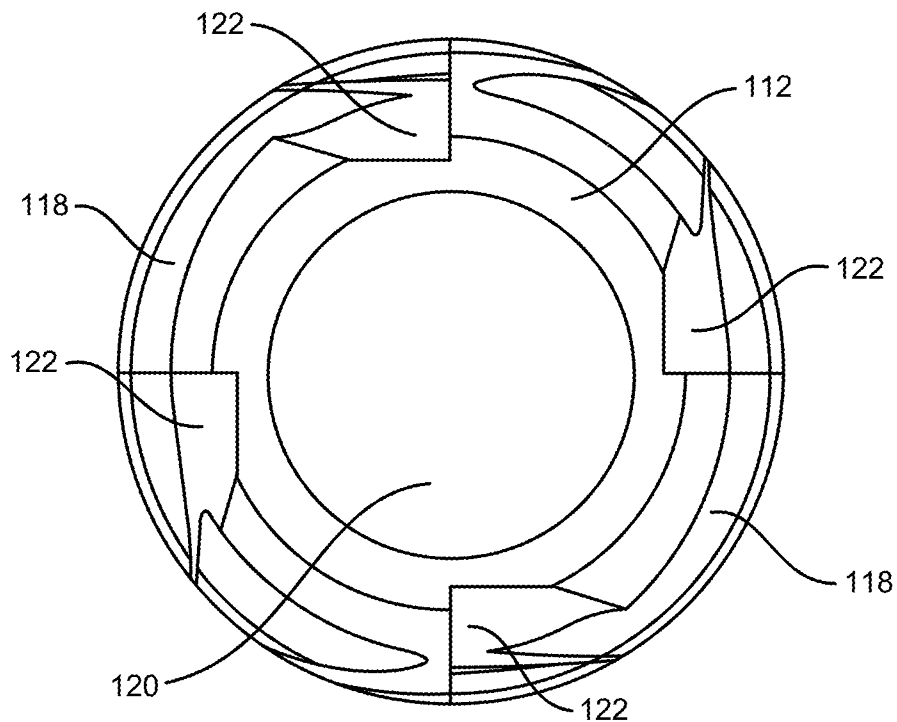
FIG. 10 is a first end view of a proximal member of the implant of FIG. 1, in accordance with an aspect of the present disclosure.
Figure 11:
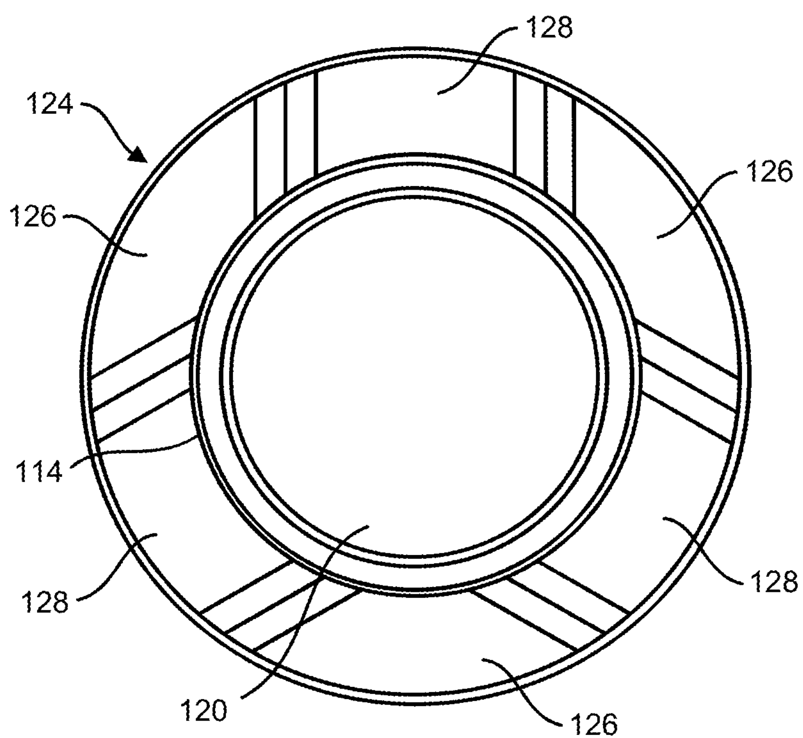
FIG. 11 is a second end view of the proximal member of FIG. 10, in accordance with an aspect of the present disclosure.

As shown in FIGS. 6-9, 10 and 11, the first or proximal member 110 includes a first end 112 and a second end 114. The first member 110 also includes a body 116 extending between the first end 112 and the second end 114. The body 116 may include at least one thread 118 positioned on an exterior surface of the body 116. The first member 110 may also include an opening or through hole 120 extending from the first end 112 to the second end 114, as shown in FIG. 7. The first end 112 may include at least one cutting flute 122 recessed into the thread 118 and body 116. As shown in FIG. 10, the first end 112 may include, for example, four cutting flutes 122. The second end 114 may include a drive feature, engagement end, or mating jaw 124, as shown in FIGS. 6-8, and 11. The engagement end 124 may include, for example, at least one protrusion or tooth 126 and at least one recess or groove 128. In the depicted embodiment, the drive feature 124 includes, for example, three protrusions 126 alternating with three recesses 128. The first member 110 may further include a groove or engagement channel 130 inset into the interior surface of the body 116 formed by the opening 120, as shown in FIG. 7.

Figure 12:
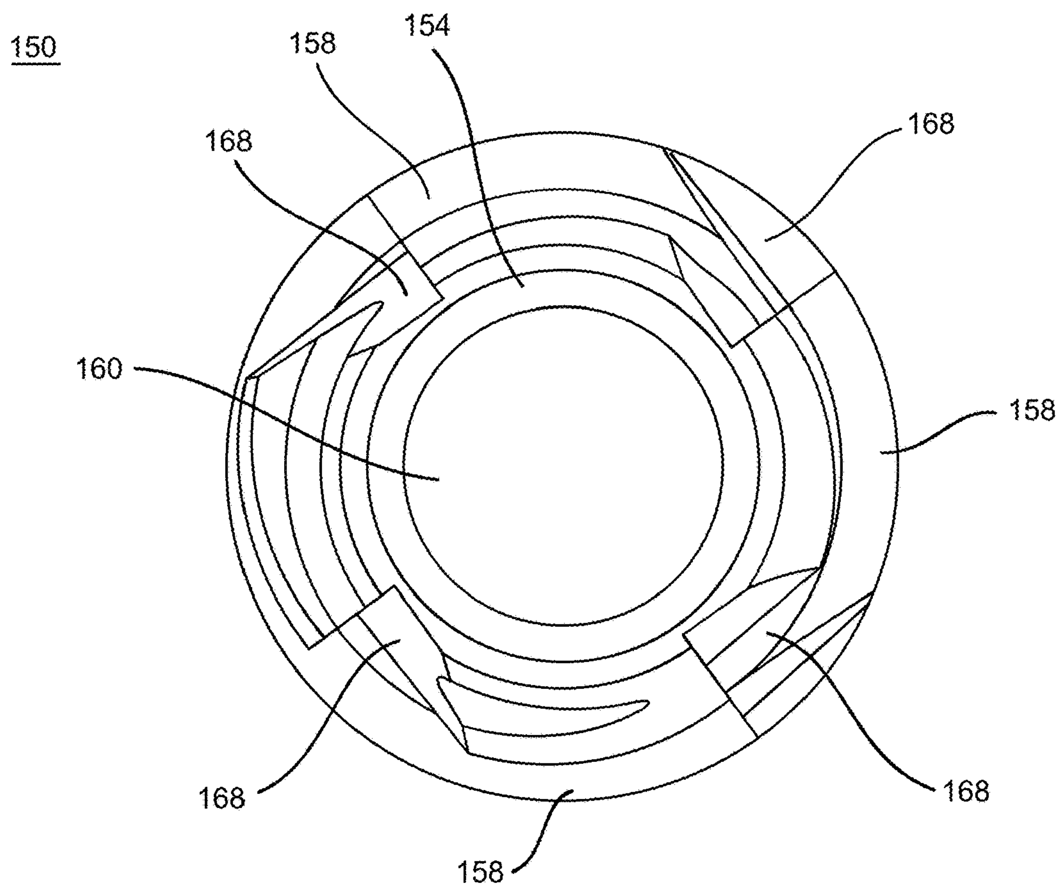
FIG. 12 is a first end view of a distal member of the implant of FIG. 1, in accordance with an aspect of the present disclosure.
Figure 13:
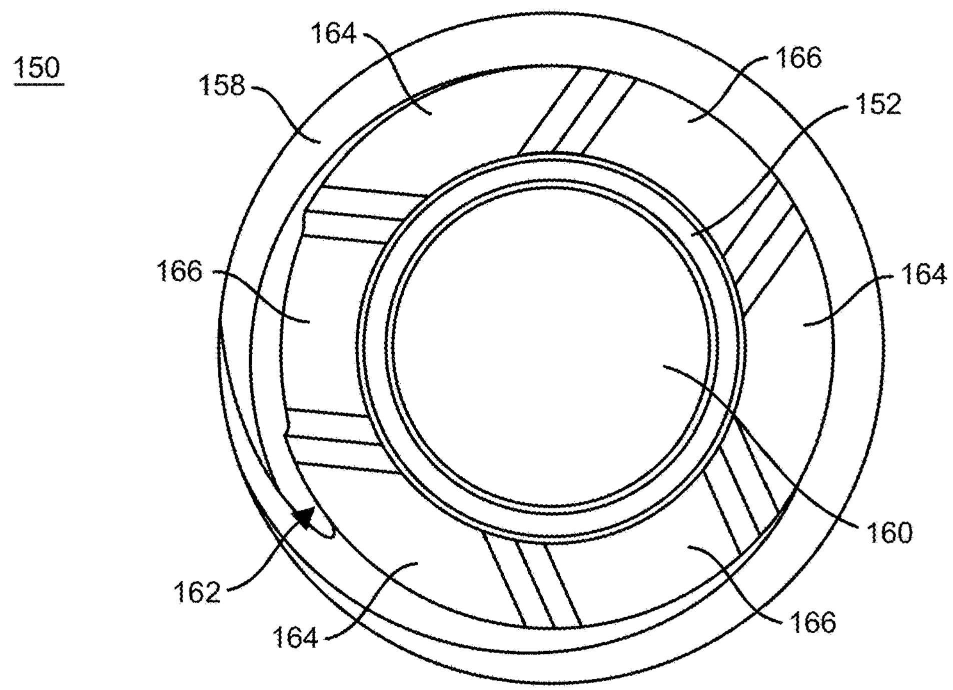
FIG. 13 is a second end view of the distal member of FIG. 12, in accordance with an aspect of the present disclosure.

Referring now to FIGS. 6-9, 12, and 13, the second or distal member 150 includes a first end 152 and a second end 154. The second member 150 also includes a body 156 extending between the first end 152 and the second end 154. The body 156 may include at least one thread 158 positioned on an exterior surface of the body 156. The second member 150 may also include an opening or through hole 160 extending from the first end 152 to the second end 154, as shown in FIG. 7. The first end 152 may include a drive feature, engagement end, or mating jaw 162, as shown in FIGS. 6, 7, 9, and 13. The engagement end 162 may include, for example, at least one protrusion or tooth 164 and at least one recess or groove 166. In the depicted embodiment, the drive feature 162 includes, for example, three protrusions 164 alternating with three recesses 166, although alternative numbers of protrusions 164 and recesses 166 are also contemplated. The second end 154 may include at least one cutting flute 168 recessed into the thread 158 and body 156. As shown in FIG. 12, the second end 154 may include, for example, four cutting flutes 168, although alternative numbers of cutting flutes 168 are also contemplated. The second member 150 may further include at least one groove or engagement channel 170 inset into an interior surface of the body 156 formed by the opening 160, as shown in FIG. 7. As shown, the at least one groove 170 may be, for example, two grooves 170.

The coupling member, compression member, or core spring 180, as shown in FIGS. 6-9, 14 and 15, includes a first end 182 and a second end 184. The coupling member 180 also includes a body 186 extending between the first end 182 and the second end 184. The body 186 may include, for example, a helical portion, helical spring, or helical member 188 near the first end 182. The helical portion 188 may be, for example, integral or one piece with the body 186 of the coupling member 180. The helical portion 188 may form, for example, a helical channel recessed into the body 186 of the coupling member 180.

With continued reference to FIGS. 6-9, 14 and 15, the body 186 may also include, for example, a pin portion or grenade pin 190 near a second end 184. The pin portion 190 may include, for example, at least one alignment mark or channel 192 extending along the longitudinal axis of the coupling member 180. The at least one alignment mark or channel 192 may be, for example, two alignment marks or channels 192 positioned on opposite sides of the body 186. The pin portion 190 may also include, for example, at least one alignment groove or recess 194. The at least one alignment groove 194 may extend, for example, perpendicular to the longitudinal axis of the body 186. The at least one alignment groove 194 may be, for example, two alignment grooves or recesses 194 positioned on opposite sides of the body 186. The at least one alignment groove 194 may be shaped, for example, to have one straight or flat side and an opposite side that includes at least one angle. In the depicted embodiment, for example, one side is flat and the opposite side includes a triangular protrusion extending into the groove 194.

Figure 14:
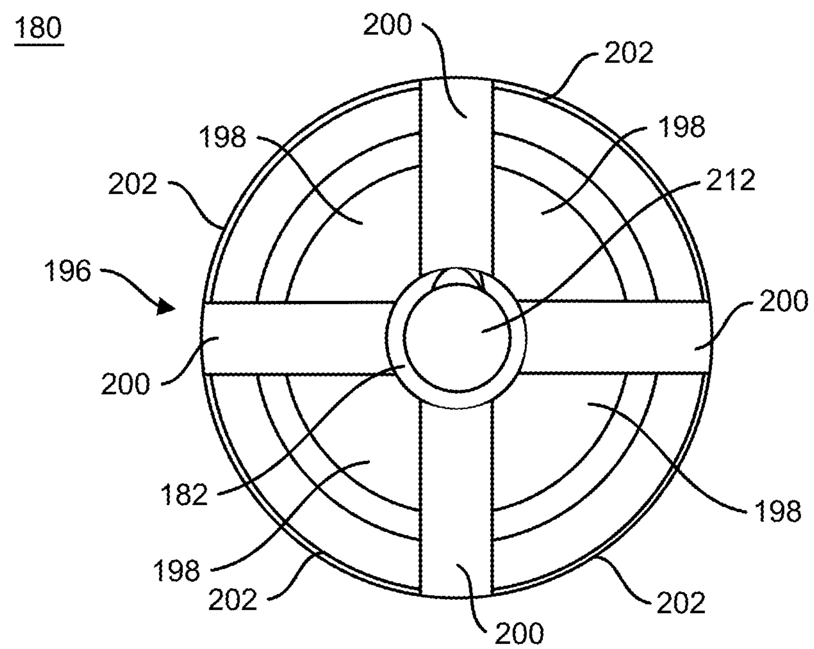
FIG. 14 is a first end view of a coupling member of the implant of FIG. 1, in accordance with an aspect of the present disclosure.

The coupling member 180 may also include a proximal snap member 196 at the first end 182, a distal snap member 204 at the second end 184, and a through hole 212 extending through the body 186 between the proximal snap member 196 and the distal snap member 204, as shown in FIGS. 6-9, 14 and 15. It is also contemplated that the interior of the coupling member 180 may be solid and not include a through hole or cannulation 212. The proximal snap member 196 may include at least one resilient member or deflecting member 198 extending away from the helical portion 188 of the body 186 and at least one groove 200. As shown in FIGS. 9 and 14, the resilient members 198 may be separated by the grooves 200 and the proximal snap member 196 may include, for example, four resilient members 198 and four grooves 200, although other numbers are also contemplated. In addition, each resilient member 198 may include at least one engagement tab or protrusion 202 positioned near the free end of the resilient member 198 opposite the end of the resilient member 198 coupled to the helical portion 188 of the body 186. The distal snap member 204 may include at least one resilient member or deflecting member 206 extending away from the pin portion 190 of the body 186 and at least one groove 208.

Figure 15:
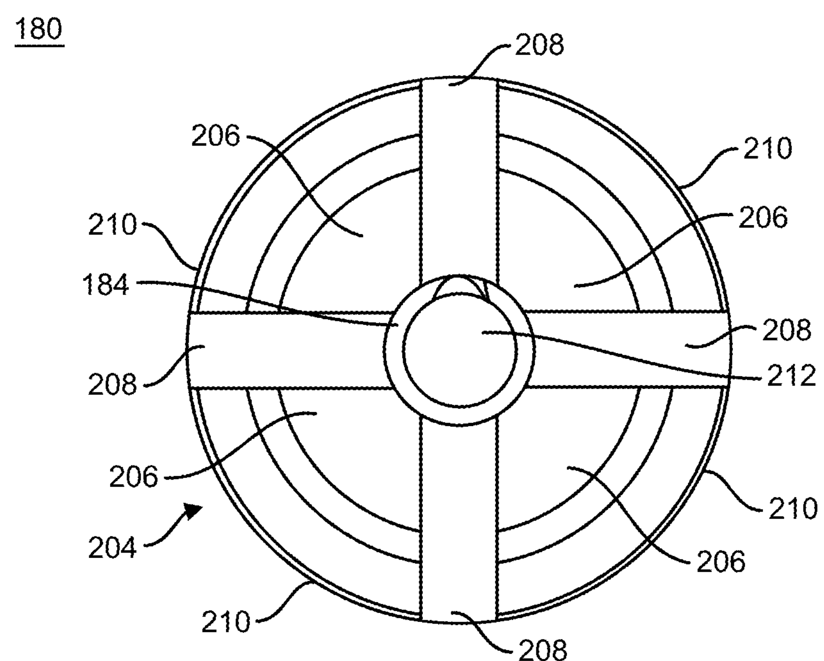
FIG. 15 is a second end view of the coupling member of FIG. 14, in accordance with an aspect of the present disclosure.
Figure 16:
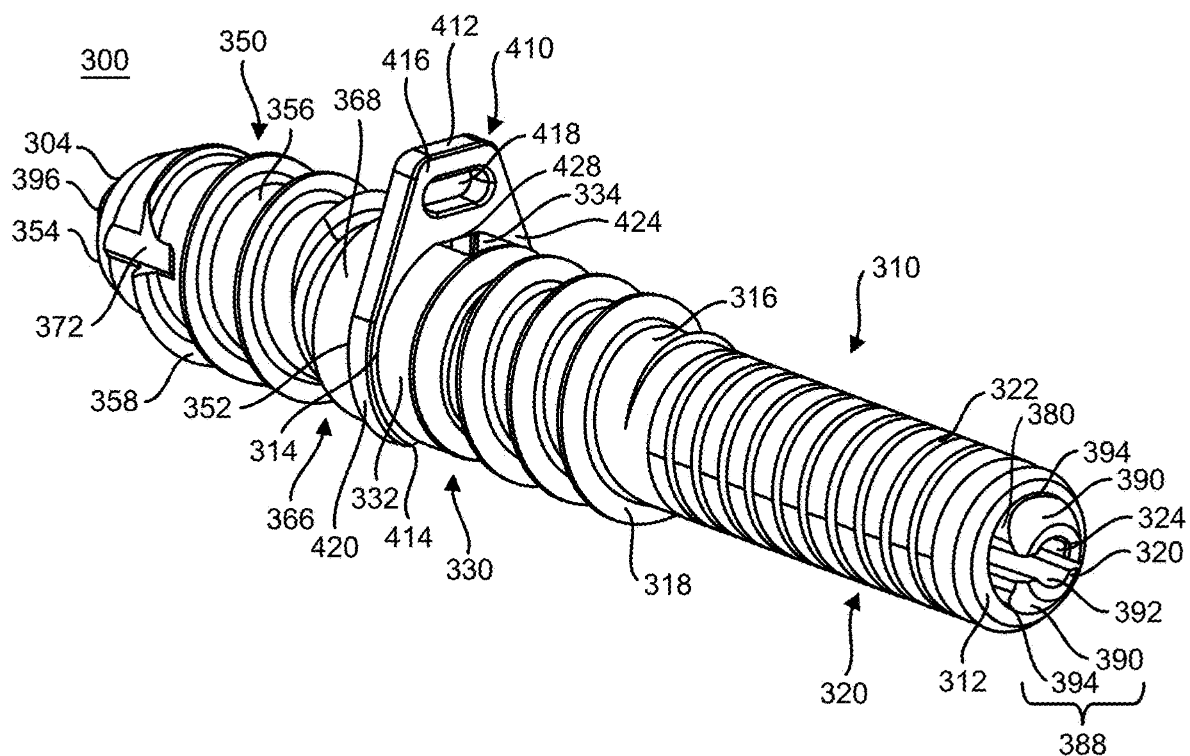
FIG. 16 is a first perspective view of another embodiment of an implant, in accordance with an aspect of the present disclosure.
Figure 17:
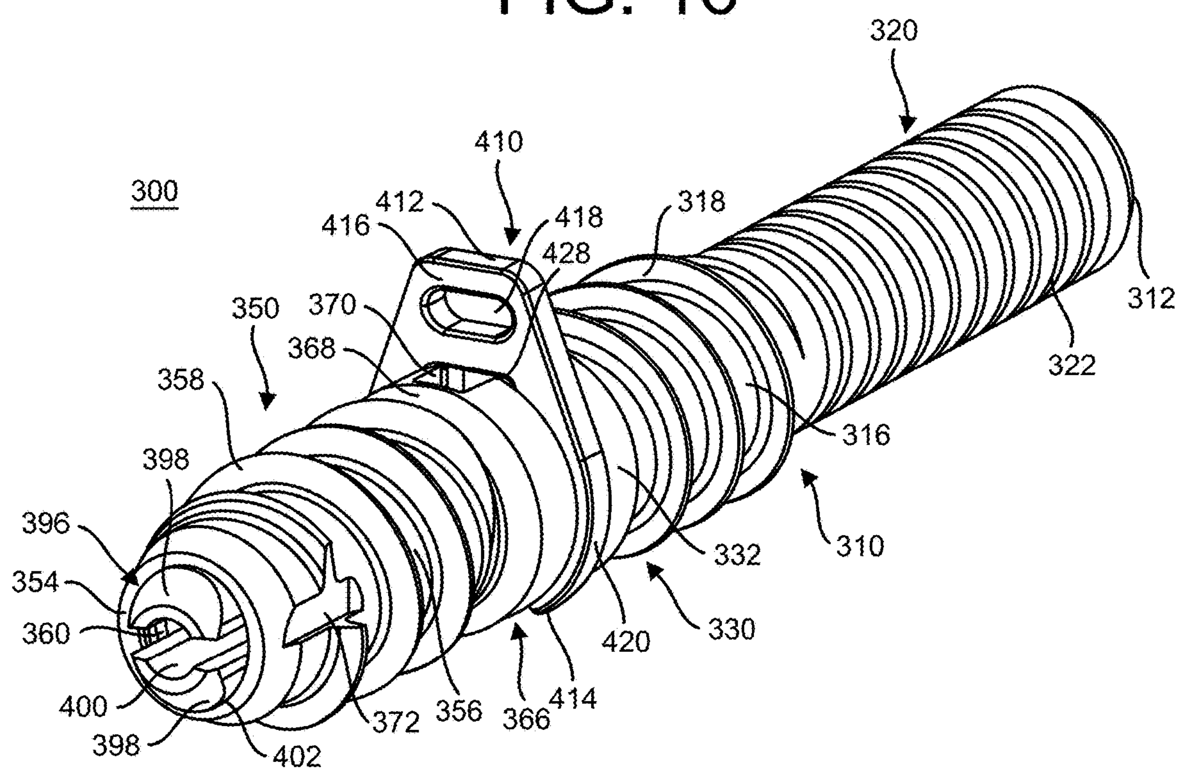
FIG. 17 is a second perspective view of the implant of FIG. 16, in accordance with an aspect of the present disclosure.
Figure 18:
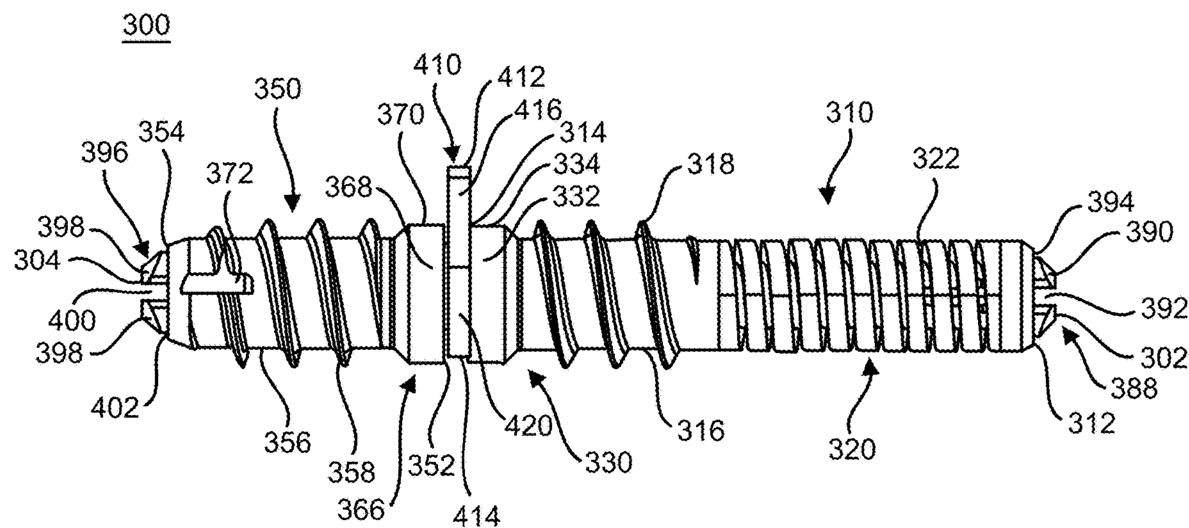
FIG. 18 is a side view of the implant of FIG. 16, in accordance with an aspect of the present disclosure.
Figure 19:
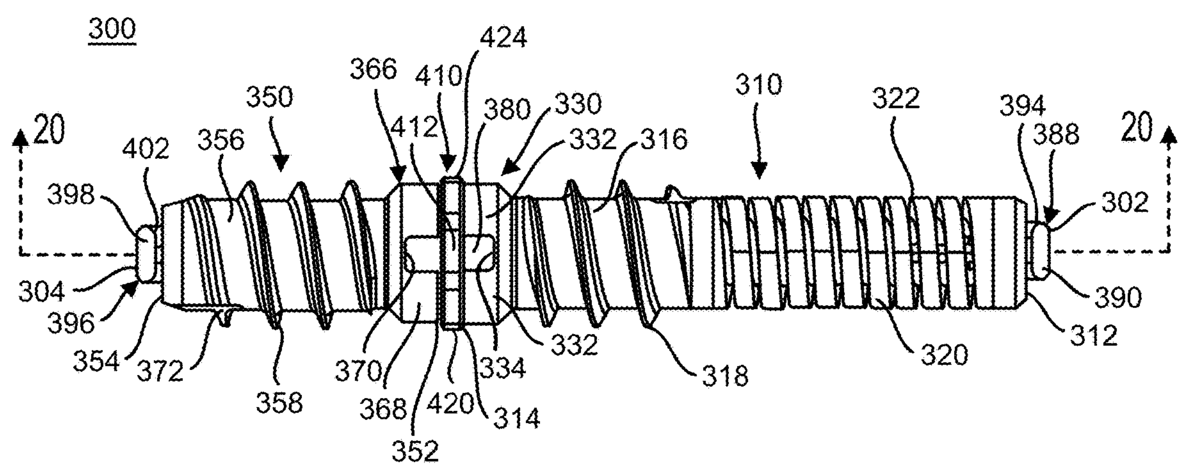
FIG. 19 is another side view of the implant of FIG. 16, in accordance with an aspect of the present disclosure.

As shown in FIGS. 8 and 15, the resilient members 206 may be separated by the grooves 208 and the distal snap member 204 may include, for example, four resilient members 206 and four grooves 208, although other numbers are also contemplated. In addition, each resilient member 206 may include at least one engagement tab or protrusion 210 positioned near the free end of the resilient member 206 opposite the end of the resilient member 206 coupled to the pin portion 190 of the body 186.

Figure 5:
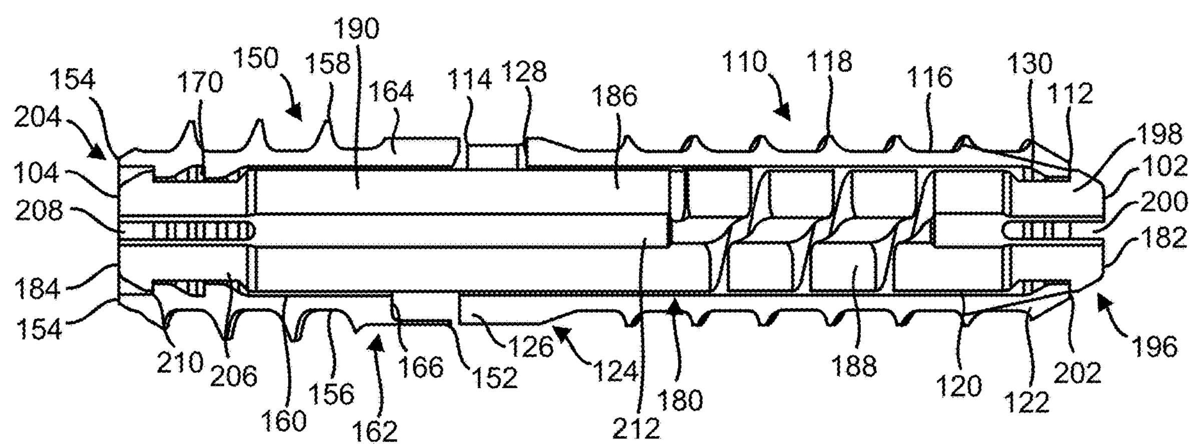
FIG. 5 is a cross-sectional view of the implant of FIG. 1 taken along line 5-5 in FIG. 3, in accordance with an aspect of the present disclosure.

Referring now to FIG. 5, the implant 100 may be assembled by, for example, inserting the first end 182 of the coupling member 180 into the through hole 120 of the first member 110. The proximal snap member 196 may be inserted until the engagement tabs 202 engage the engagement channel 130 or the first end 112 of the first member 110 to secure the coupling member 180 to the first member 110. Next, a biasing member (not shown) may be inserted to engage the alignment grooves 194, as shown in FIG. 6, to tension the helical portion 188. The biasing member (not shown) may be, for example, a fork, pin or other insert that can engage both the alignment grooves 194. After the helical portion 188 is tensioned, the coupling member 180 may be inserted into the through hole 160 of the second member 150. The distal snap member 204 may be inserted until the engagement tabs 210 are received within the engagement channels 170 or engage the second end 154 of the second member 150. Once the coupling member 180 is coupled to the first and second members 110, 150, the biasing member (not shown) may be positioned between the first end 152 of the second member 150 and the second end 114 of the first member 110 and engaging the alignment grooves 194 of the compression member 180. The biasing member (not shown) may then be removed from the alignment grooves 194 activating the helical portion 188 to apply compression to any joint coupled to the first and second members 110, 150. The biasing member (not shown) may be, for example, similar to biasing member 410 or biasing member 460, as described in greater detail below.

Referring now to FIGS. 16-35, an implant 300 is shown. The implant 300 includes a first end 302 and a second end 304, as shown in FIGS. 16-20. The implant 300 also includes a first or proximal member 310, a second or distal member 350, a coupling member 380 positioned to engage the first member 310 on one end and the second member 350 on another end, and a biasing member 410 positioned between the first and second members 310, 350 and configured or sized and shaped to engage the coupling member 380. The components of the implant 300 may be made of, for example, titanium, stainless steel, nitinol, PEEK, or another similar biocompatible material, as known by one of ordinary skill in the art.

Figure 20:
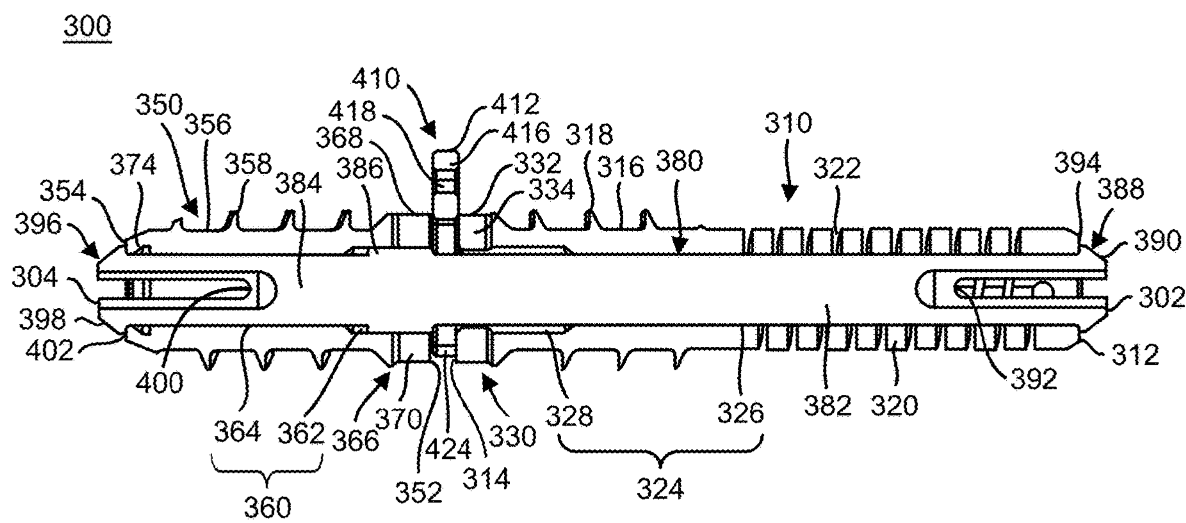
FIG. 20 is a cross-sectional view of the implant of FIG. 16 taken along line 20-20 of FIG. 19, in accordance with an aspect of the present disclosure.
Figure 21:
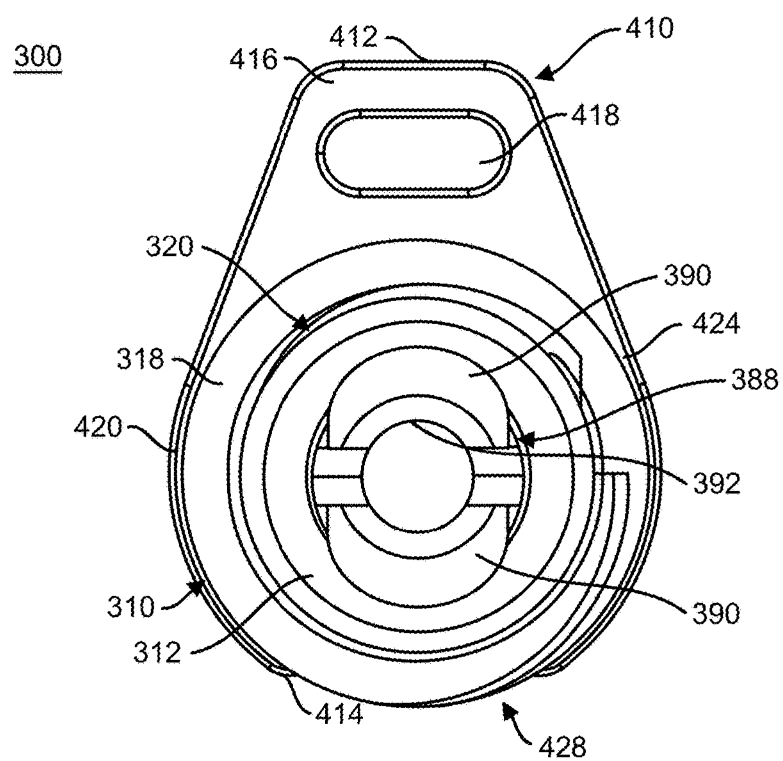
FIG. 21 is a first end view of the implant of FIG. 16, in accordance with an aspect of the present disclosure.
Figure 22:
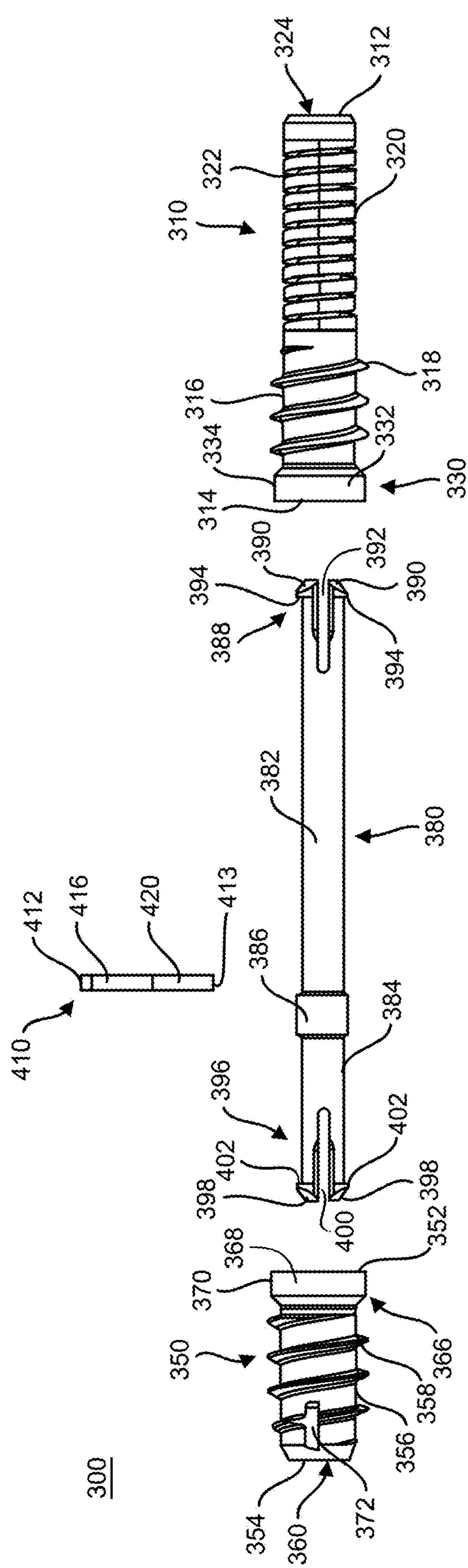
FIG. 22 is an exploded, side view of the implant of FIG. 16, in accordance with an aspect of the present disclosure.
Figure 23:
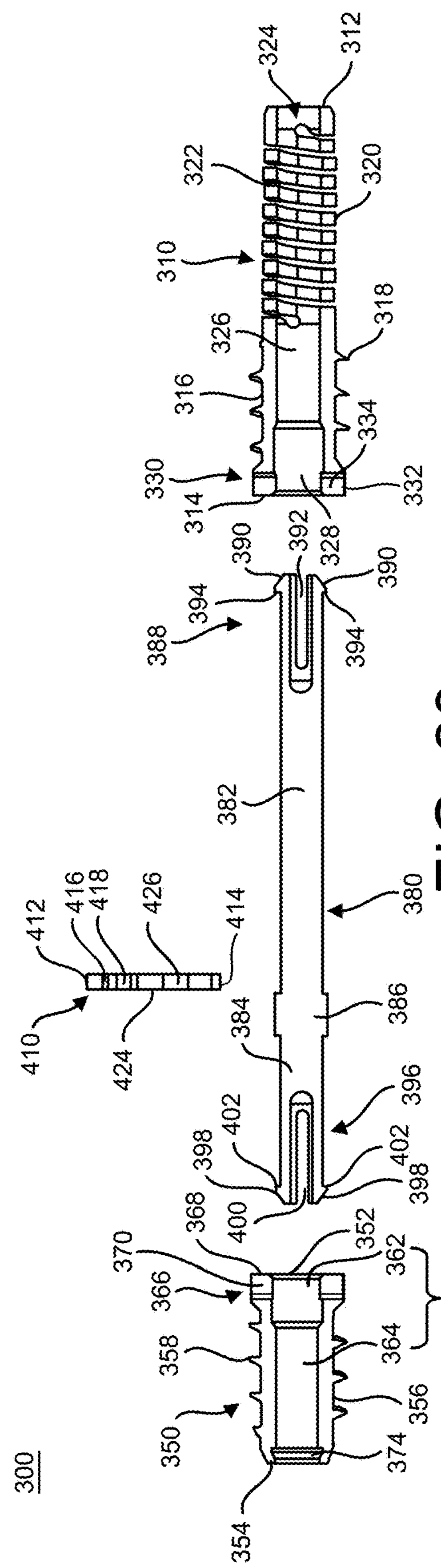
FIG. 23 is an exploded, cross-sectional view of the implant of FIG. 16 taken along line 20-20 in FIG. 19, in accordance with an aspect of the present disclosure.
Figure 24:
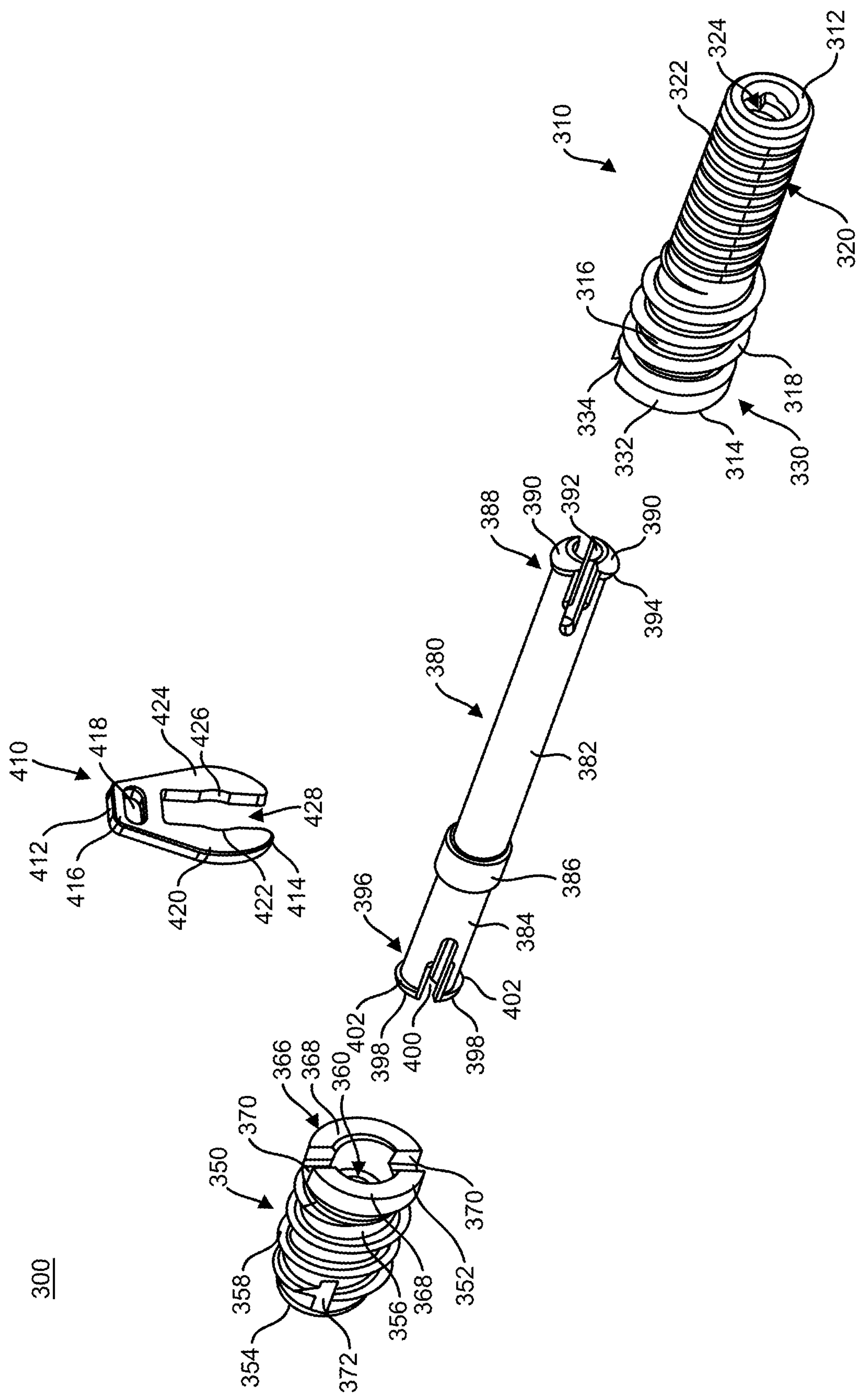
FIG. 24 is an exploded, first perspective view of the implant of FIG. 16, in accordance with an aspect of the present disclosure.
Figure 25:
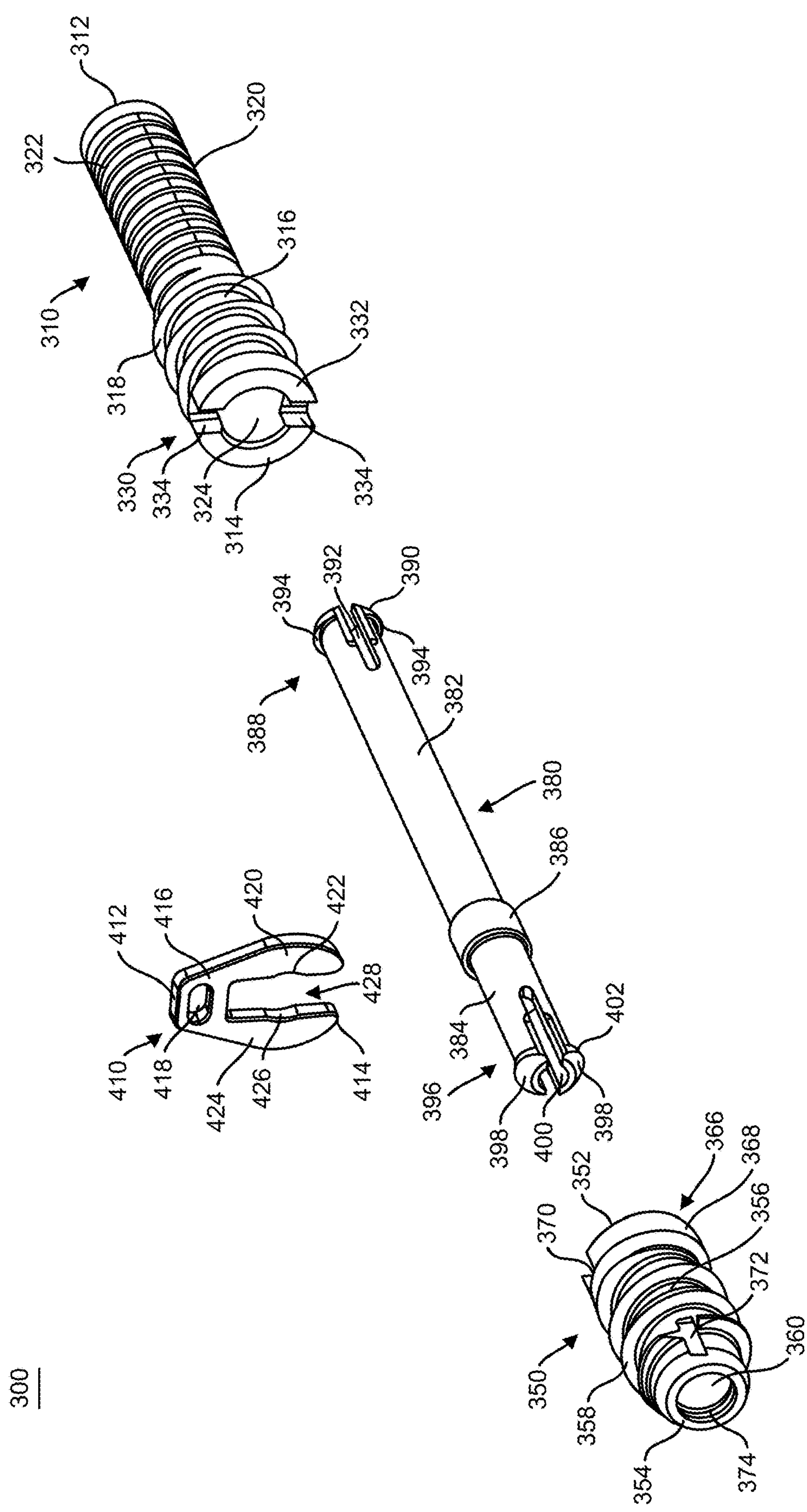
FIG. 25 is an exploded, second perspective view of the implant of FIG. 16, in accordance with an aspect of the present disclosure.
Figure 26:
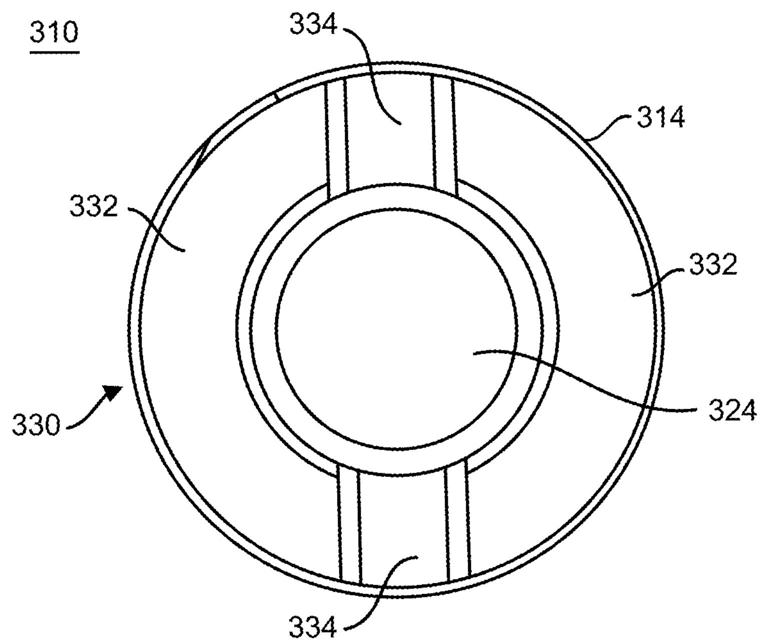
FIG. 26 is an end view of a first member of the implant of FIG. 16, in accordance with an aspect of the present disclosure.
Figure 27:
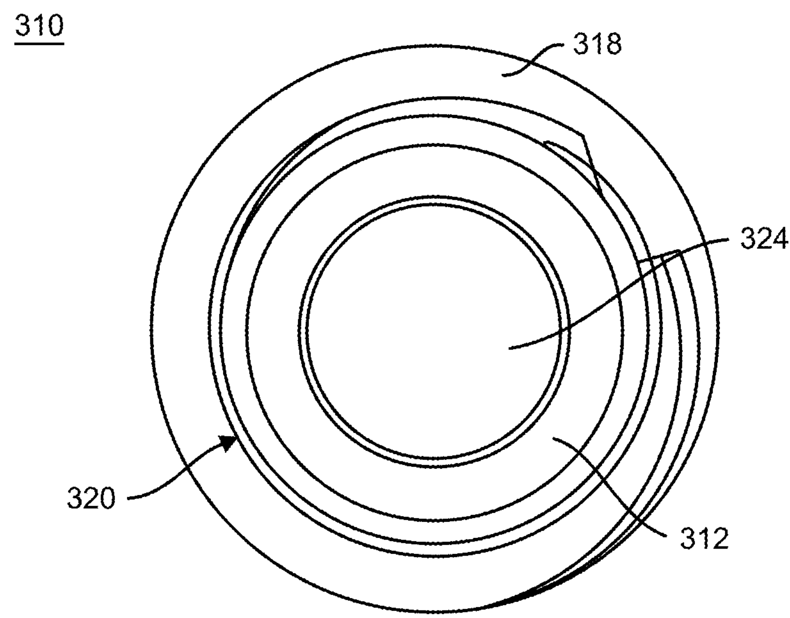
FIG. 27 is another end view of the first member of FIG. 26, in accordance with an aspect of the present disclosure.

As shown in FIGS. 16-20 and 22-27, the first or proximal member 310 includes a first end 312 and a second end 314. The first member 310 also includes a body portion 316 coupled to or integral with a deformable member, spring member or spring portion 320. In the depicted embodiment of FIGS. 16-20 and 22-27, the body portion 316 and deformable member 320 are coupled together to form a one-piece construct. It is also contemplated that the body portion 316 and deformable member 320 could be, for example, at least two separate pieces that engage when assembled to form the first member 310, one example of such an arrangement is discussed in greater detail below with respect to implant 500. The body portion 316 extends from the second end 314 toward the first end 312, the deformable member 320 extends from the first end 312 toward the second end 314, and the body portion 316 transitions to the deformable member 320 at a point between the first and second ends 312, 314. The first member 310 may also include an opening or through hole 324 extending from the first end 312 to the second end 114, as shown in FIGS. 20 and 23. The through hole 324 may include, for example, a first portion 326 with a first diameter and a second portion 328 with a second diameter, as shown in FIG. 23. The first portion 326 may be positioned, for example, inside of the deformable member 320. The second portion 328 may be positioned, for example, inside of the body portion 316. The body portion 316 may include at least one thread 318 positioned on an exterior surface of the body portion 316. The deformable member 320 may include a helical opening or continuous helical opening 322 extending along the length of the deformable member 320. The helical opening 322 may extend from an exterior surface of the deformable member 320 into the through hole 324, as shown in FIGS. 20, 23, and 24. The helical opening 322 may form, for example, a spring portion allowing for deformation of the deformable member 320 when force is applied. The body portion 316 of the first member 310 may also include a drive feature or engagement end 330 at the second end 314, as shown in FIGS. 20, 23-25 and 26. The drive feature 330 may include, for example, at least one protrusion 332 and at least one recess 334. In the depicted embodiment, the drive feature 330 includes two protrusions 332 and two recesses 334, although other numbers of protrusions 332 and recesses 334 are also contemplated.

Figure 28:
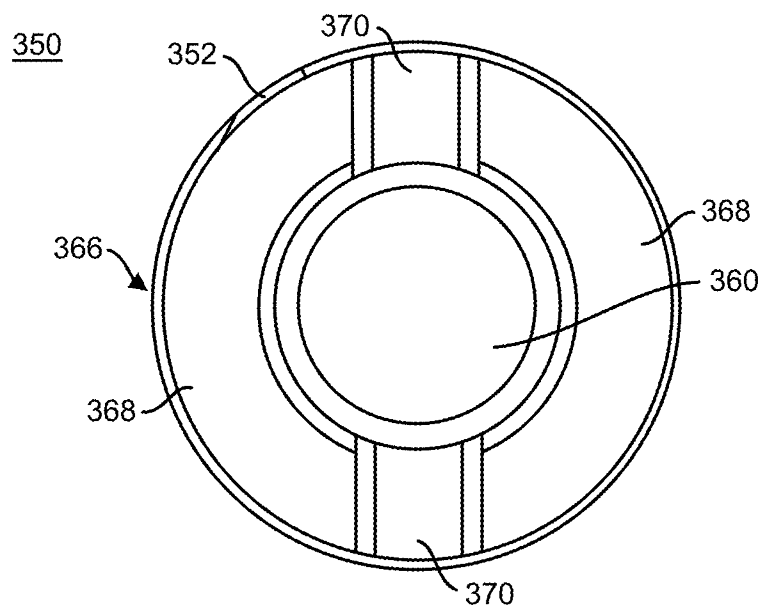
FIG. 28 is an end view of a second member of the implant of FIG. 16, in accordance with an aspect of the present disclosure.
Figure 29:
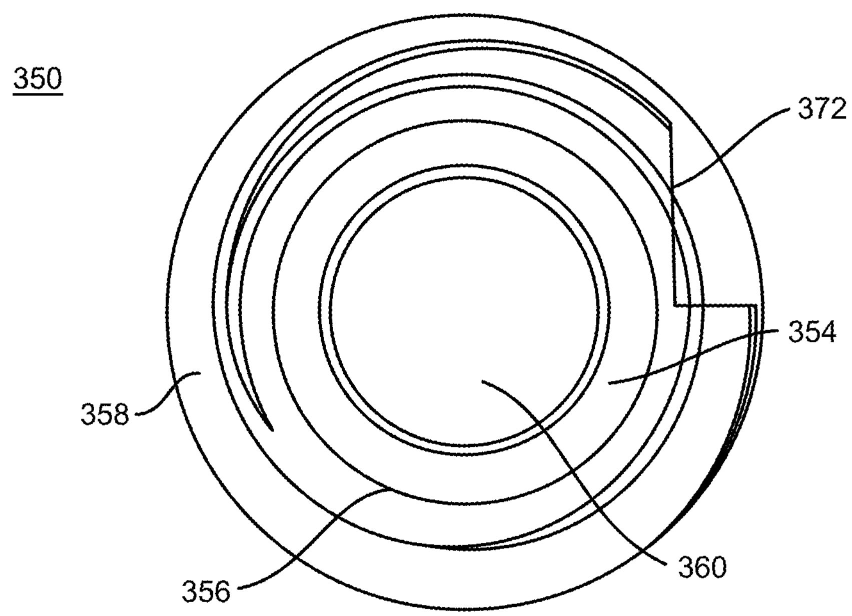
FIG. 29 is another end view of the second member of FIG. 28, in accordance with an aspect of the present disclosure.
Figure 30:
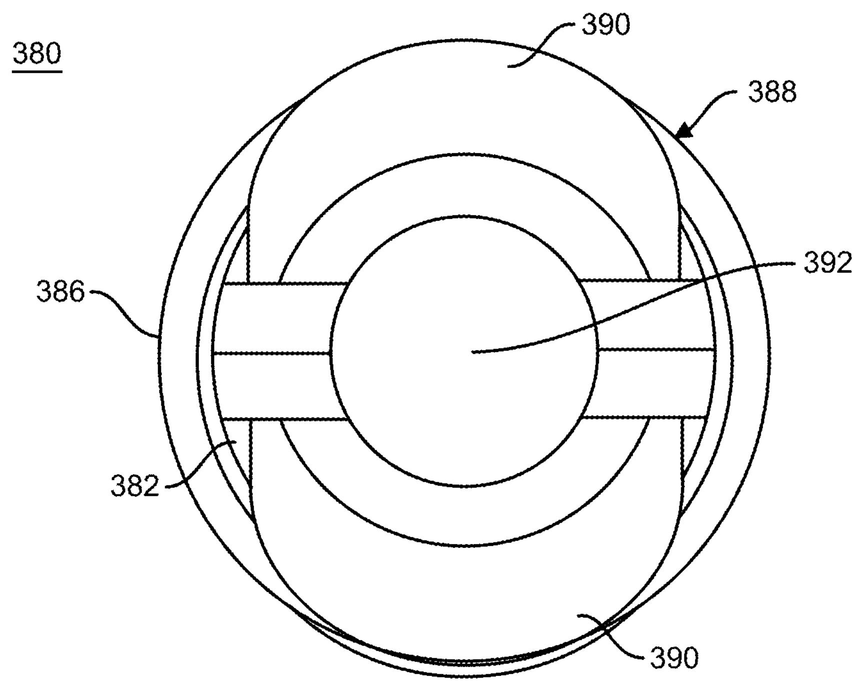
FIG. 30 is an end view of a coupling member of the implant of FIG. 16, in accordance with an aspect of the present disclosure.
Figure 31:
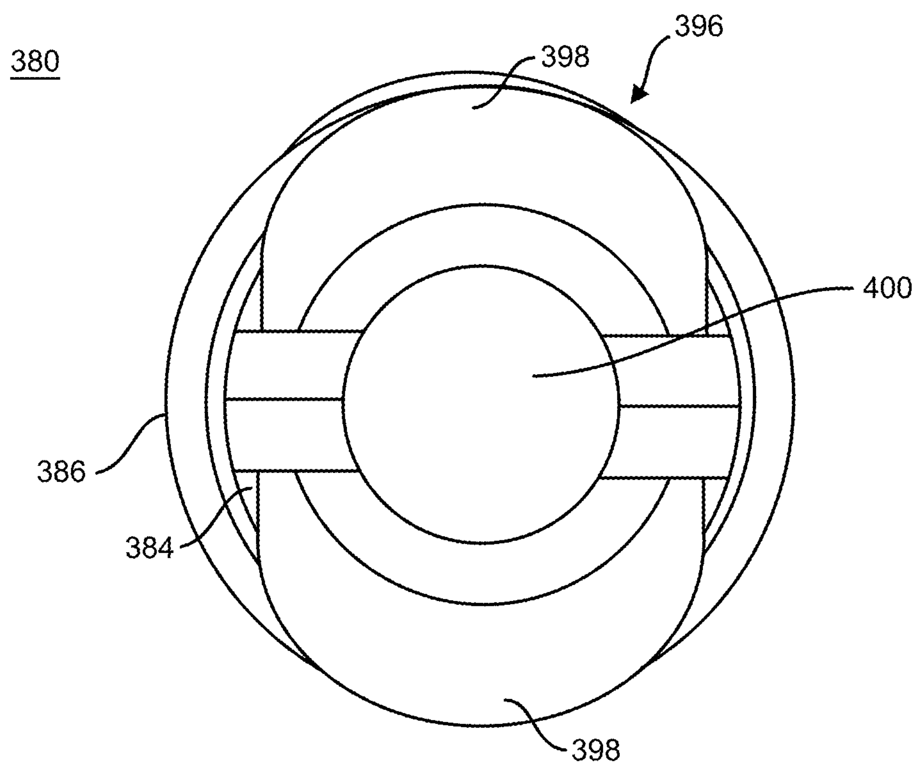
FIG. 31 is another end view of the coupling member of FIG. 30, in accordance with an aspect of the present disclosure.
Figure 32:
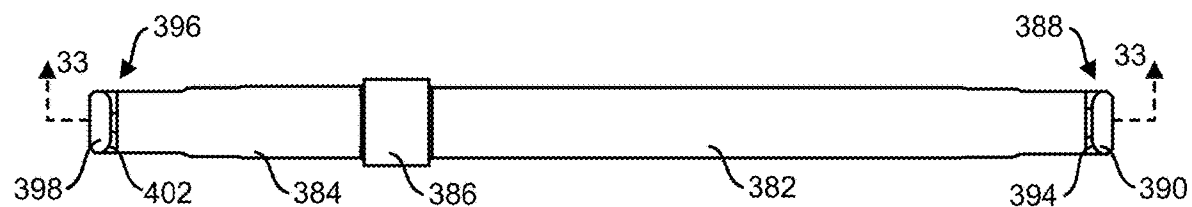
FIG. 32 is a top view of the coupling member of FIG. 30, in accordance with an aspect of the present disclosure.
Figure 33:
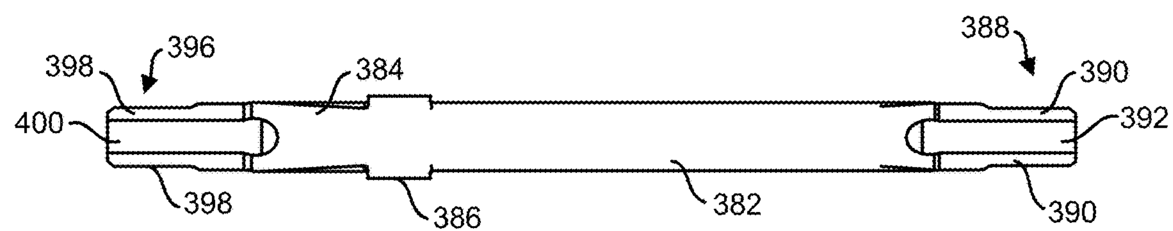
FIG. 33 is a cross-sectional view of the coupling member of FIG. 30 taken along line 33-33 in FIG. 32, in accordance with an aspect of the present disclosure.
Figure 34:
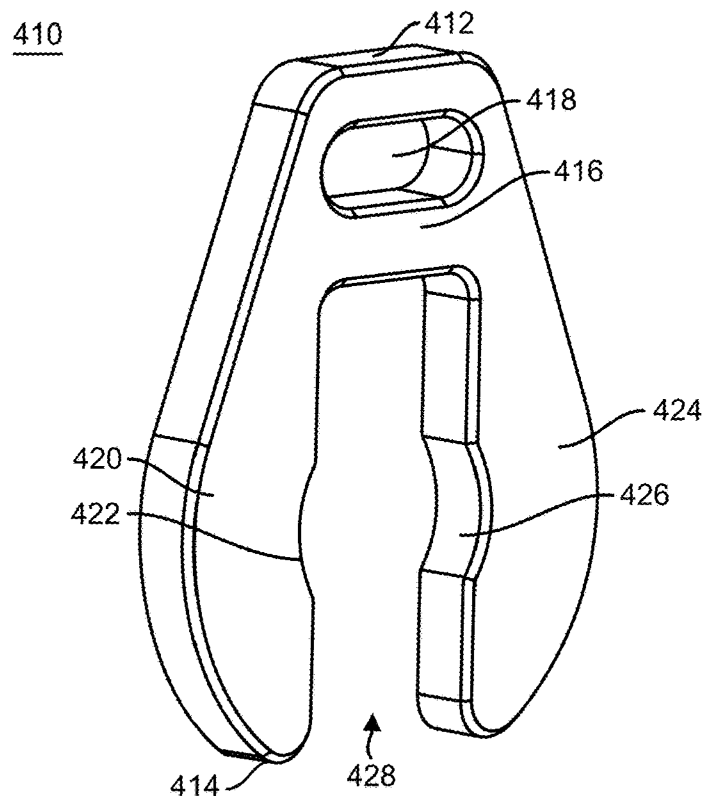
FIG. 34 is a perspective view of a biasing member of the implant of FIG. 16, in accordance with an aspect of the present disclosure.
Figure 35:
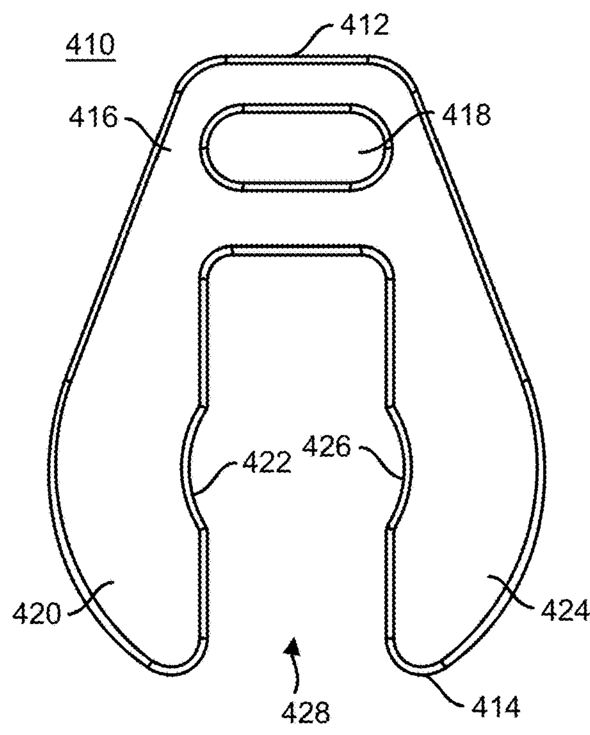
FIG. 35 is an end view of the biasing member of FIG. 34, in accordance with an aspect of the present disclosure.
Figure 36:
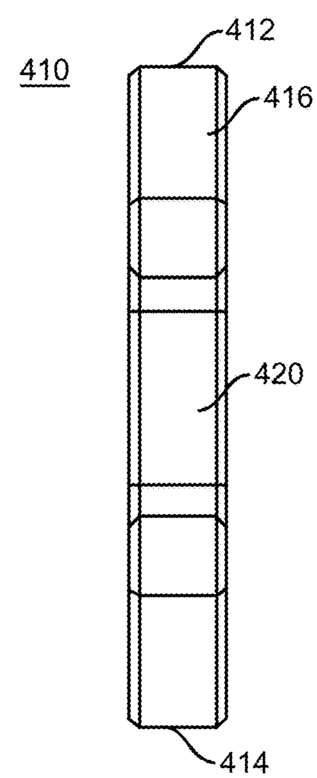
FIG. 36 is a side view of the biasing member of FIG. 34, in accordance with an aspect of the present disclosure.
Figure 37:
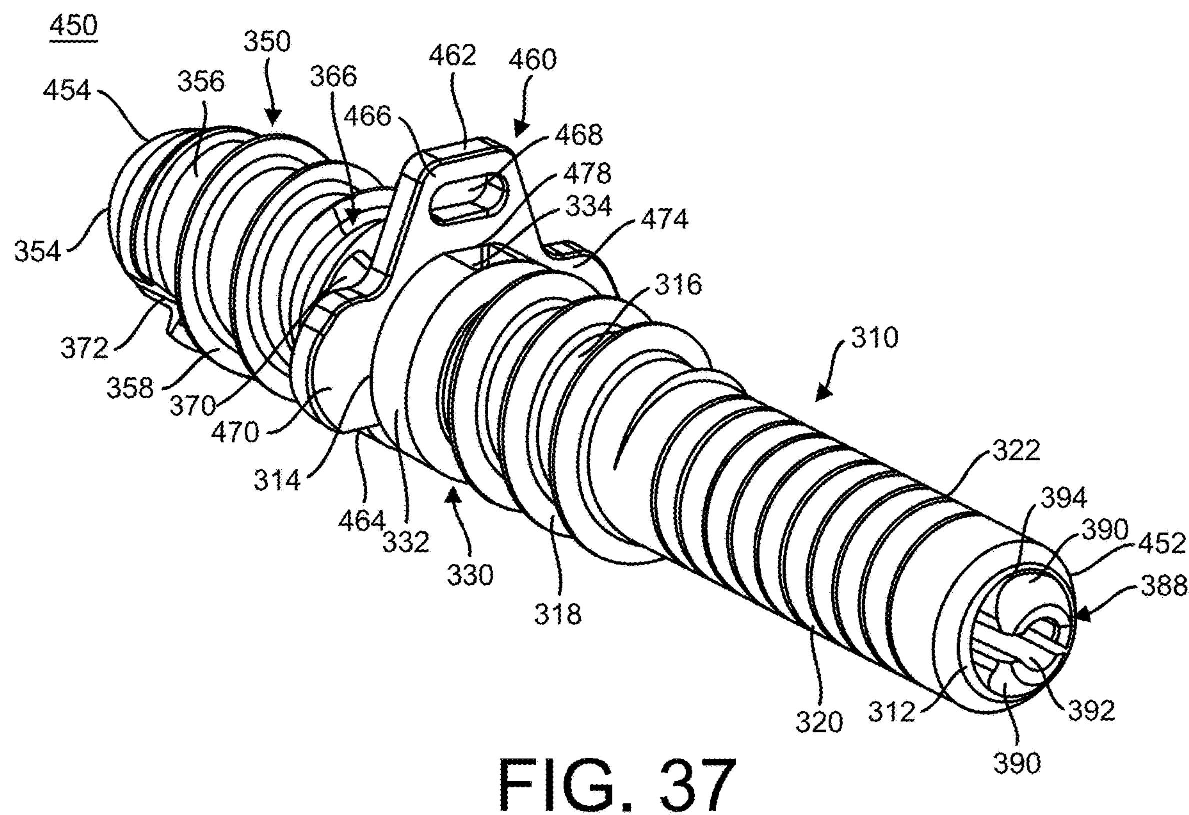
FIG. 37 is a first perspective view of another embodiment of an implant, in accordance with an aspect of the present disclosure.
Figure 38:
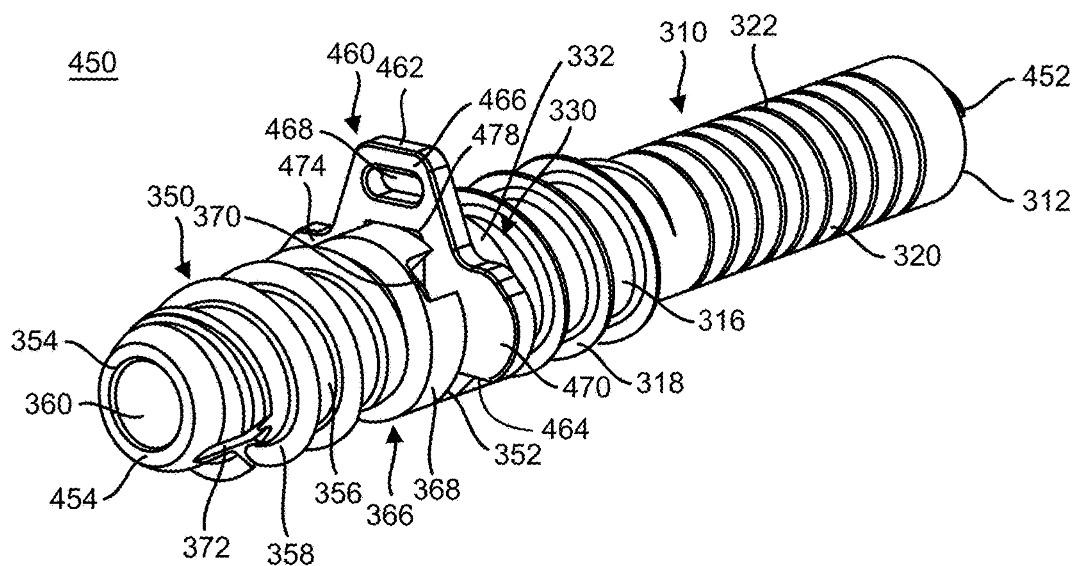
FIG. 38 is a second perspective view of the implant of FIG. 37, in accordance with an aspect of the present disclosure.
Figure 39:
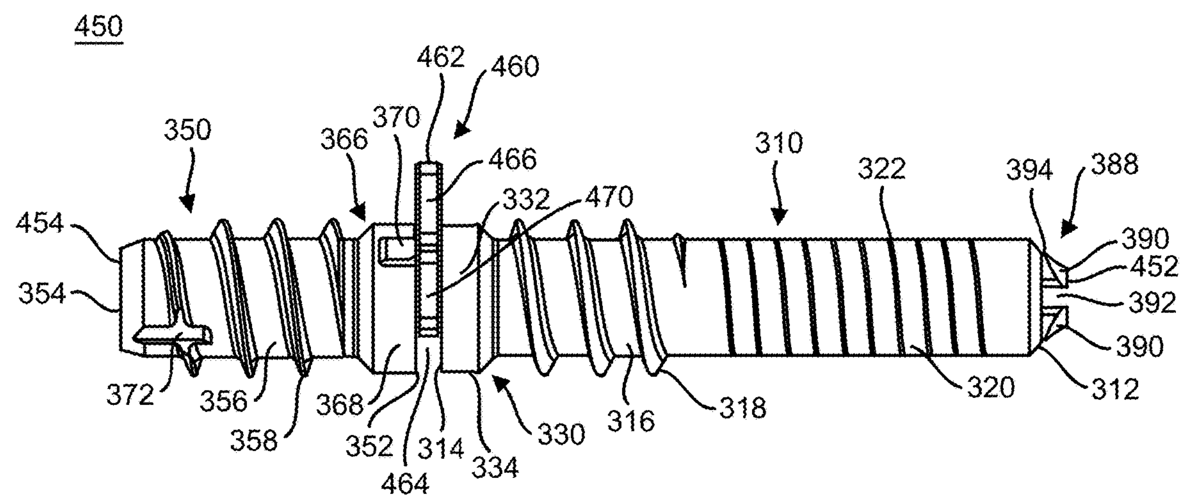
FIG. 39 is a first side view of the implant of FIG. 37, in accordance with an aspect of the present disclosure.
Figure 40:
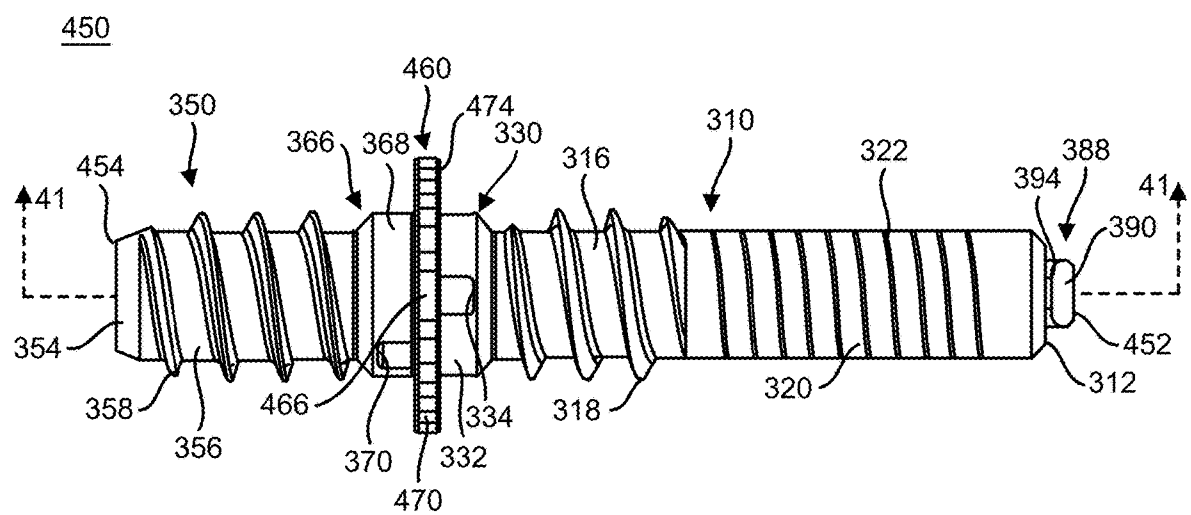
FIG. 40 is a second side view of the implant of FIG. 37, in accordance with an aspect of the present disclosure.

Referring now to FIGS. 16-20 and 22-27, the second or distal member 350 includes a first end 352 and a second end 354. The second member 350 also includes a body 356 extending between the first end 352 and the second end 354. The body 356 may include at least one thread 358 positioned on an exterior surface of the body 356. The second member 350 may also include an opening or through hole 360 extending from the first end 352 to the second end 354, as shown in FIG. 23. The through hole 360 may include, for example, a first portion 362 and a second portion 364. The first portion 362 may extend from the first end 352 into the body 356 and the second portion 364 may extend from the second end 354 into the body 356 until the second portion 364 engages the first portion 362. The first end 352 of the body 356 may also include a drive feature or engagement end 366, as shown in FIGS. 23, 24, and 28. The drive feature 366 may include, for example, at least one protrusion 368 and at least one recess 370. In the depicted embodiment, the drive feature 366 includes two protrusions 368 and two recesses 370, although other numbers of protrusions 368 and recesses 370 are also contemplated. The second end 354 may also include at least one cutting flute 372 recessed into the thread 358 and the body 356. As shown in FIG. 29, the second end 354 may include, for example, one cutting flute 372, although other numbers of cutting flutes 372 are also contemplated. The second member 350 may further include at least one groove or engagement channel 370 inset into the body 356 from the through hole 360, as shown in FIG. 23.

The coupling member or compression member 380, as shown in FIGS. 22-25 and 30-33, includes a first portion 382, a second portion 384, and a stop member 386 positioned between and coupled to the first portion 382 and the second portion 384. The first portion 382 extends from a first end of the coupling member 380 to the stop member 386. The second portion 384 extends from a second end of the coupling member 380 to the stop member 386. The first portion 382 may have, for example, a first diameter and a first length. The second portion 384 may have, for example, a second diameter and a second length. The stop member 386 may have, for example, a third diameter and a third length. The first diameter may be, for example, the same size or a different size than the second diameter. The third diameter may be, for example, larger than the first and second diameters. In the depicted embodiment, the first length may be, for example, longer than the second length and the first and second lengths may be, for example, longer than the third length. Although shown as a solid member, it is also contemplated that the coupling member 380 may include, for example, a through hole or cannulation extending from the first end of the coupling member 380 to the second end of the coupling member 380.

The coupling member 380 may also include a proximal snap member 388 at the first end and a distal snap member 396 at the second end, as shown in FIGS. 22-25 and 30-33. The proximal snap member 388 may include at least one resilient member or deflecting member 390 extending away from the first portion 382 and at least one channel or groove 392. The at least one channel 392 may be positioned between the at least one resilient member 390. As shown in the depicted embodiment, the proximal snap member 388 may include, for example, two resilient members 390 and one channel 392 extending into the first portion 382 between the two resilient members 390, although alternative combinations of resilient members 390 and channels 392 are also contemplated. In addition, each resilient member 390 may include at least one engagement tab or protrusion 394 positioned near the free end of the resilient member 390 opposite the end of the resilient member 390 coupled to the first portion 382. The distal snap member 396 may include at least one resilient member or deflecting member 398 extending away from the second portion 384 and at least one channel or groove 400. The at least one channel 400 may be positioned between the at least one resilient member 398. As shown in the depicted embodiment, the distal snap member 396 may include, for example, two resilient members 398 and one channel 400 extending into the second portion 384 between the two resilient members 398, although alternative numbers of resilient members 398 and channels 400 are also contemplated. In addition, each resilient member 398 may include at least one engagement tab or protrusion 402 positioned near the free end of the resilient member 398 opposite the end of the resilient member 398 coupled to the second portion 384.

As shown in FIGS. 24, 25 and 34-36, the biasing member or activation member 410 may have a first end 412 and a second end 414. The biasing member 410 may also include a body portion 416 at the first end 412. The body portion 416 may include an opening 418 for receiving or engaging with a tool for insertion or removal of the biasing member 410. The biasing member 410 may further include a first leg 420 and a second leg 424. The legs 420, 424 may extend away from the body portion 416 to the second end 414 of the biasing member 410. The legs 420, 424 may be separated by a channel 428 extending into the biasing member 410 from the second end 414 to the body portion 416. The outer or outward facing surfaces of the legs 420, 424 may be, for example, curved or rounded. The inner or inward facing surfaces of the legs 420, 424 are positioned adjacent to the channel 428 and may have, for example, relatively parallel sides to each other. The inner surface of the first leg 420 may also include, for example, a first groove 422 inset into the inner surface of the first leg 420. The inner surface of the second leg 424 may also include, for example, a second groove 426 inset into the inner surface of the second leg 424. The first and second grooves 422, 426 may be, for example, sized and shaped or configured to receive the coupling member 380. The grooves 422, 426 may be positioned, for example, along the legs 420, 424 at a depth corresponding to the desired depth of insertion of the biasing member 410 between the bones of a joint.

Referring now to FIG. 20, the implant 300 may be assembled by, for example, inserting the proximal snap member 388 of the coupling member 380 into the through hole 324 of the first member 310. The proximal snap member 388 may be inserted until the engagement tabs 394 engage the first end 312 of the first member 310 to secure the coupling member 380 to the first member 310. A biasing member 410 may be inserted to engage the coupling member 380, for example, the first portion 382 of the coupling member 380. The biasing member 410 may be, for example, inserted next to the stop member 386 on the first portion 382 of the coupling member 380 to tension the deformable member 320 of the first member 310 between the stop member 386 and the proximal snap member 388 of the coupling member 380. The second portion 384 of the coupling member 380 may be inserted into the through hole 360 of the second member 350. The distal snap member 396 may be inserted until the engagement tabs 402 are received within the groove 374 of the second member 350 or engage the second end 354 of the second member 350. Once the coupling member 380 is coupled to the first and second members 310, 350, the biasing member 410 may be removed resulting in the deformable member 320 to applying a compressive force to any two opposing bones coupled to the first and second members 310, 350, respectively. After the biasing member 410 is removed, the stop member 386 may be, for example, positioned within the first portion 362 of the through hole 360 of the second member 350, the second portion 328 of the through hole 324 of the first member 310, or at least a portion of the first portion 362 of the second member 350 and at least a portion of the second portion 328 of the first member 310.

Referring now to FIGS. 37-49, another implant 450 is shown. The implant 450 includes a first end 452 and a second end 454, as shown in FIGS. 37-41. The implant 450 also includes the first or proximal member 310, the second or distal member 350, the coupling member 380 positioned to engage the first member 310 on one end and the second member 350 on another end, and a biasing member 460 positioned between the first and second members 310, 350 and engaging the coupling member 380. The first member 310, second member 350, and coupling member 380 may be the same or similar to the type described above with reference to implant 300 and will not be described again here in complete detail for brevity sake. The components of the implant 450 may be made of, for example, titanium, stainless steel, nitinol, PEEK, or another similar biocompatible material, as known by one of ordinary skill in the art.

Figure 46:
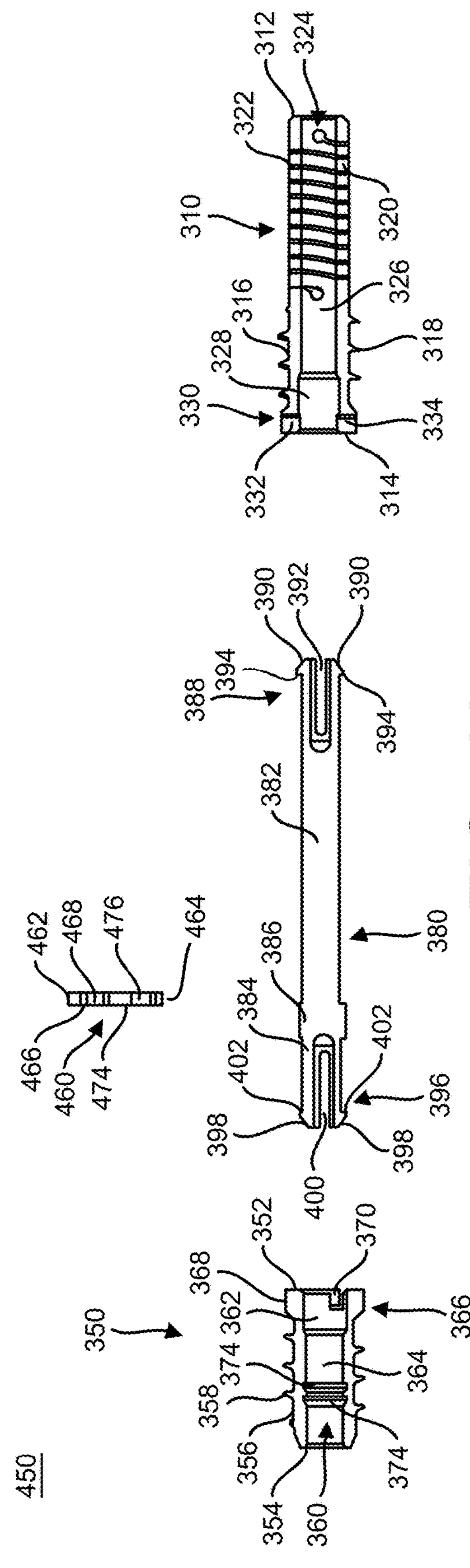
FIG. 46 is an exploded, cross-sectional view of the implant of FIG. 37 taken along line 41-41 in FIG. 40, in accordance with an aspect of the present disclosure.
Figure 47:
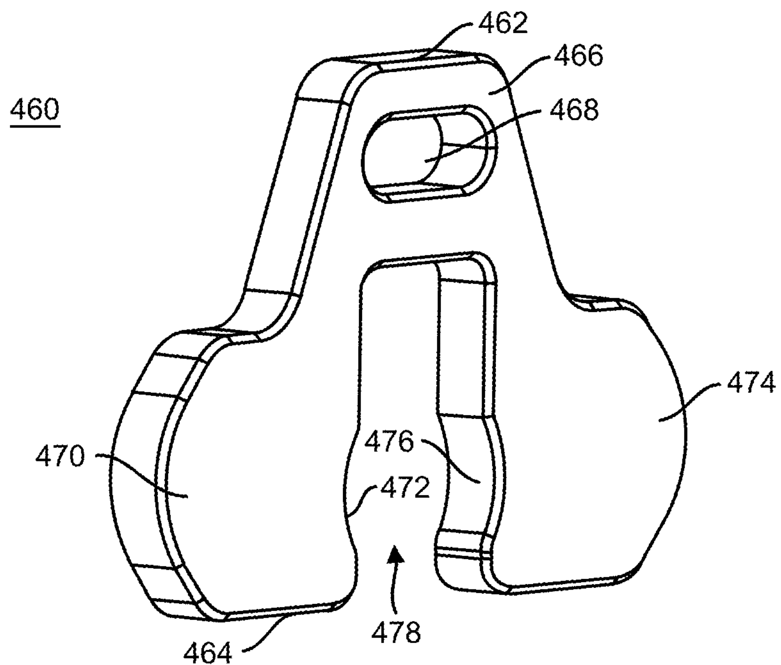
FIG. 47 is a perspective view of a biasing member of the implant of FIG. 37, in accordance with an aspect of the present disclosure.
Figure 48:
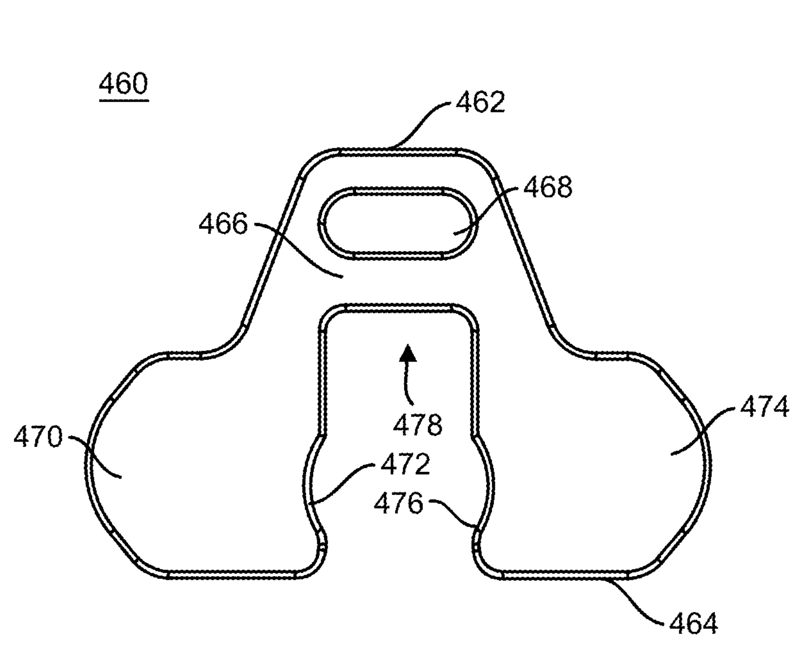
FIG. 48 is an end view of the biasing member of FIG. 47, in accordance with an aspect of the present disclosure.
Figure 49:
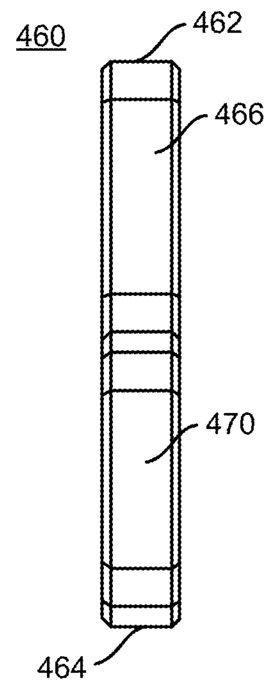
FIG. 49 is a side view of the biasing member of FIG. 47, in accordance with an aspect of the present disclosure.

Referring now to FIG. 46 and as described in greater detail above, the second member 350 may include at least one groove or engagement channel 374. In the depicted embodiment the second member 350 of the implant 450 includes at least two grooves 374 recessed into the body 356 of the second member 350 between the first end 352 and the second end 354 of the through hole 360. As shown in FIG. 46, the at least two grooves 374 may be, for example, two grooves 374. With continued reference to FIG. 46, the coupling member 380 of the implant 450 includes a first portion 382, a second portion 384 and a stop member 386. As shown in the embodiment of FIG. 46, the stop member 386 may be, for example, positioned directly adjacent to the end of the channel 400 of the distal snap member 396.

The biasing member or activation member 460 may have a first end 462 and a second end 464, as shown in FIGS. 43-49. The biasing member 460 may also include a body portion 466 at the first end 462. The body portion 466 may include an opening 468 for receiving or engaging with a tool for insertion or removal of the biasing member 460. The biasing member 460 may further include a first leg 470 and a second leg 474. The legs 470, 474 may extend away from the body portion 466 to the second end 464 of the biasing member 460. The legs 470, 474 may be separated by a channel 478 extending into the biasing member 460 from the second end 464 to the body portion 466. The outer or outward facing surfaces of the legs 470, 474 may be, for example, curved, arced, or rounded. The inner or inward facing surfaces of the legs 470, 474 are positioned adjacent to the channel 478 and may have, for example, relatively parallel sides to each other. The inner surface of the first leg 470 may also include, for example, a first groove 472 inset into the inner surface of the first leg 470. The inner surface of the second leg 474 may also include, for example, a second groove 476 inset into the inner surface of the second leg 474. The first and second grooves 472, 476 may be, for example, sized and shaped to receive the coupling member 380. The grooves 472, 476 may be positioned, for example, along the legs 470, 474 at a depth corresponding to the desired depth of insertion of the biasing member 460 between the bones of a joint and perpendicular to the joint axis.

Figure 41:
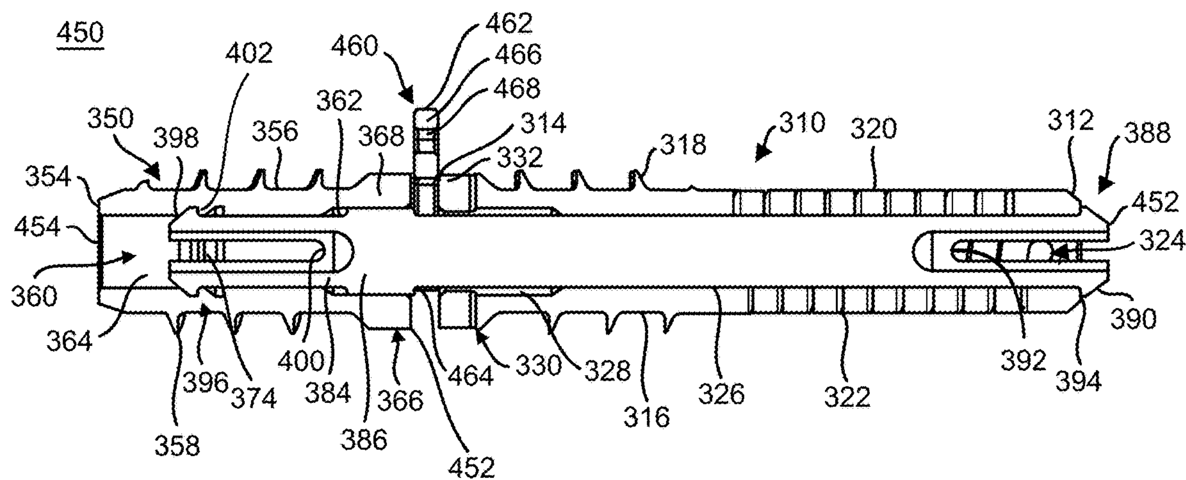
FIG. 41 is a cross-sectional view of the implant of FIG. 37 taken along line 41-41 in FIG. 40, in accordance with an aspect of the present disclosure.
Figure 42:
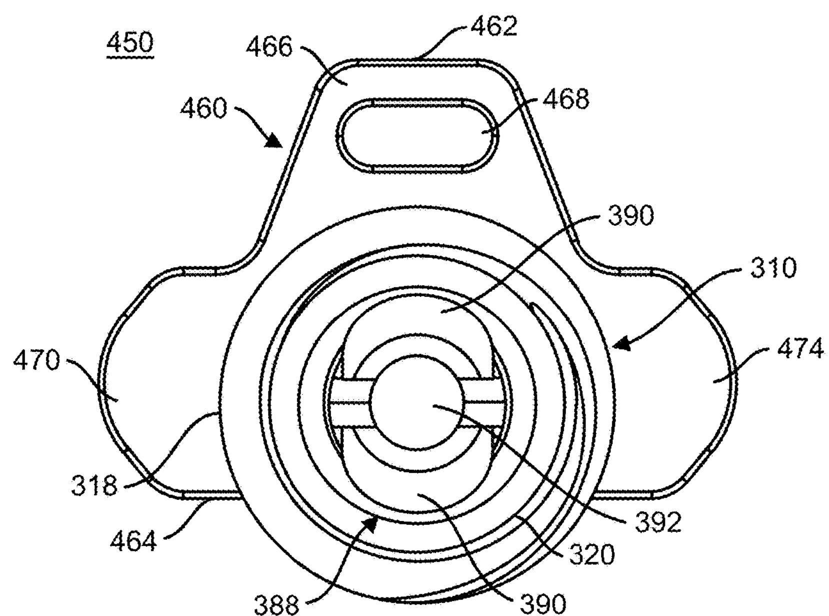
FIG. 42 is an end view of the implant of FIG. 37, in accordance with an aspect of the present disclosure.
Figure 43:
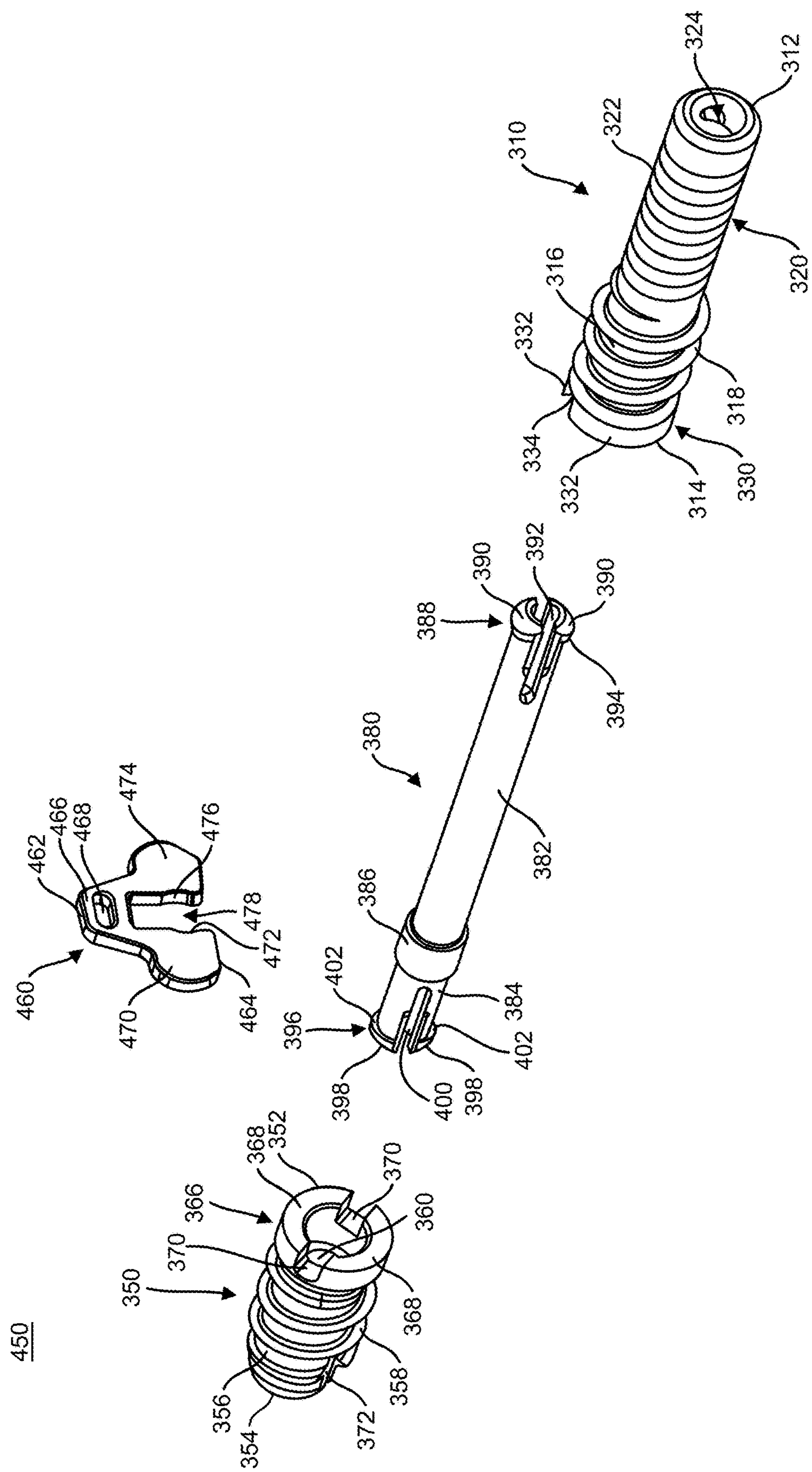
FIG. 43 is an exploded, perspective view of the implant of FIG. 37, in accordance with an aspect of the present disclosure.
Figure 44:
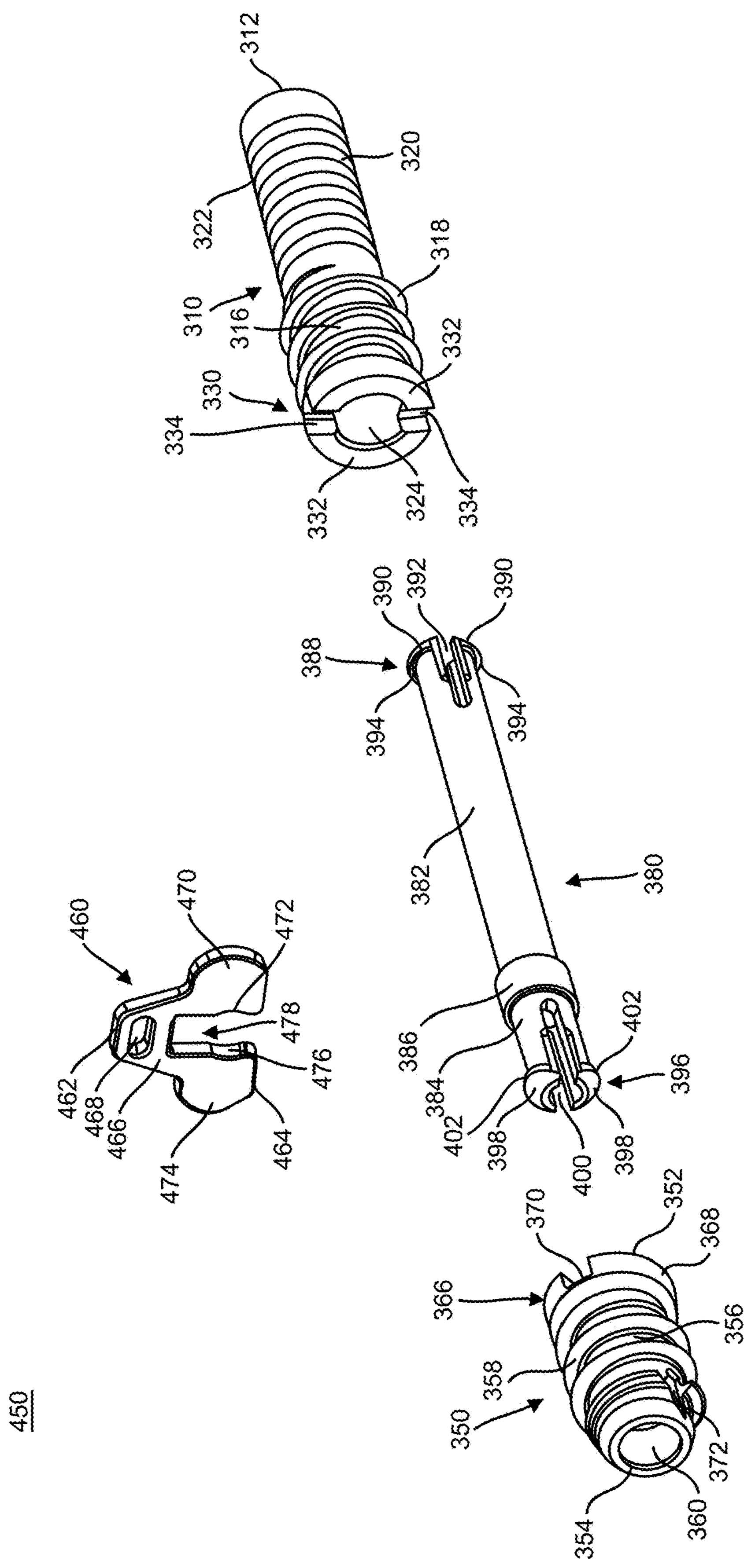
FIG. 44 is another exploded, perspective view of the implant of FIG. 37, in accordance with an aspect of the present disclosure.
Figure 45:
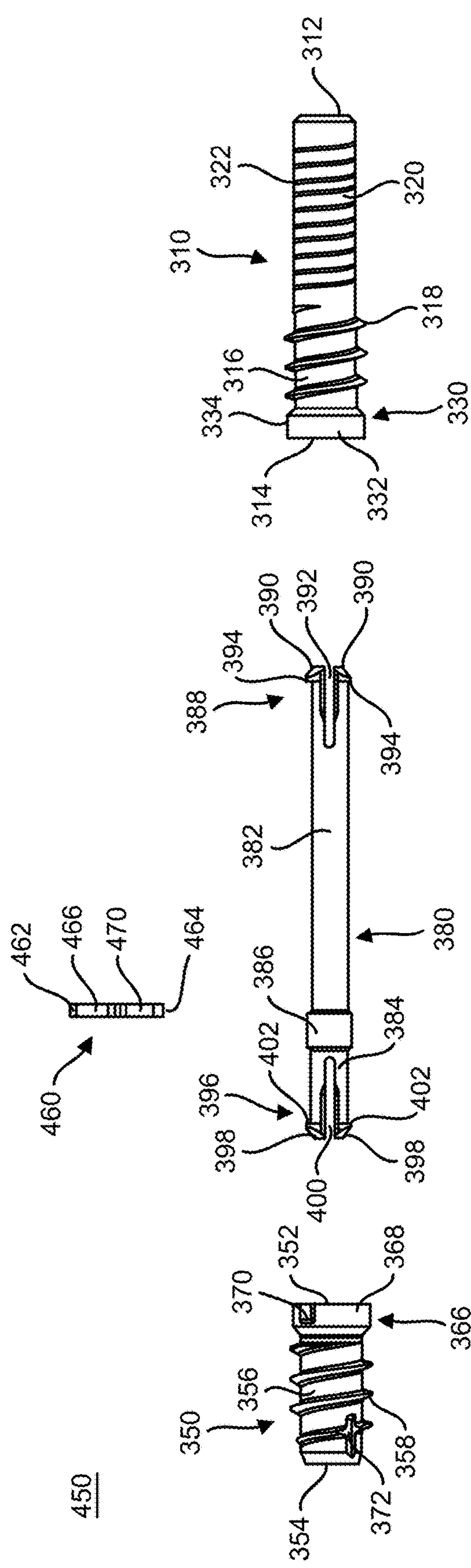
FIG. 45 is an exploded, side view of the implant of FIG. 37, in accordance with an aspect of the present disclosure.

Referring now to FIG. 41, the implant 450 may be assembled by, for example, inserting the proximal snap member 388 of the coupling member 380 into the through hole 324 of the first member 310. The proximal snap member 388 may be inserted until the engagement tabs 394 engage the first end 312 of the first member 310 to secure the coupling member 380 to the first member 310. A biasing member 460 may be inserted to engage the coupling member 380, for example, the first portion 382 of the coupling member 380. The biasing member 460 may be, for example, inserted next to the stop member 386 on the first portion 382 of the coupling member 380 to tension the deformable member 320 of the first member 310 between the stop member 386 and the proximal snap member 388 of the coupling member 380. The second portion 384 of the coupling member 380 may be inserted into the through hole 360 of the second member 350. The distal snap member 396 may be inserted until the engagement tabs 402 are received within the groove 374 of the second member 350 or engage the second end 354 of the second member 350. Once the coupling member 380 is coupled to the first and second members 310, 350, the biasing member 460 may be removed causing the deformable member 320 to apply a compressive force across any bone joint in which the first and second members 310, 350 are implanted. After the biasing member 460 is removed, the stop member 386 may be, for example, positioned within the first portion 362 of the through hole 360 of the second member 350, the second portion 328 of the through hole 324 of the first member 310, or at least a portion of the first portion 362 of the second member 350 and at least a portion of the second portion 328 of the first member 310.

Figure 50:
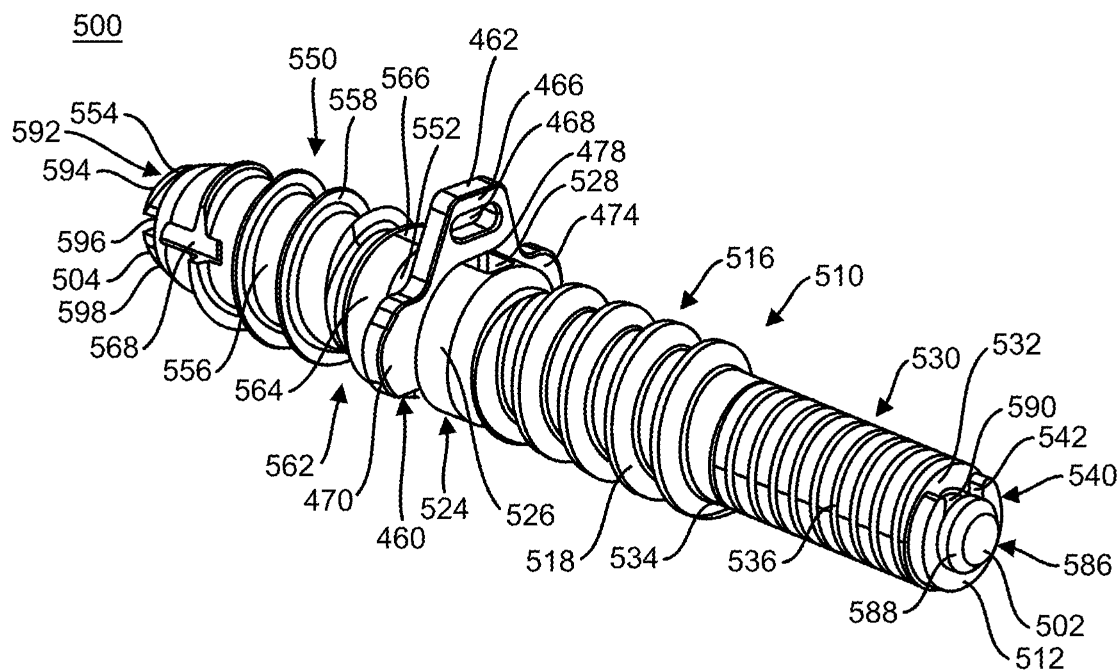
FIG. 50 is a first perspective view of another embodiment of an implant, in accordance with an aspect of the present disclosure.
Figure 51:
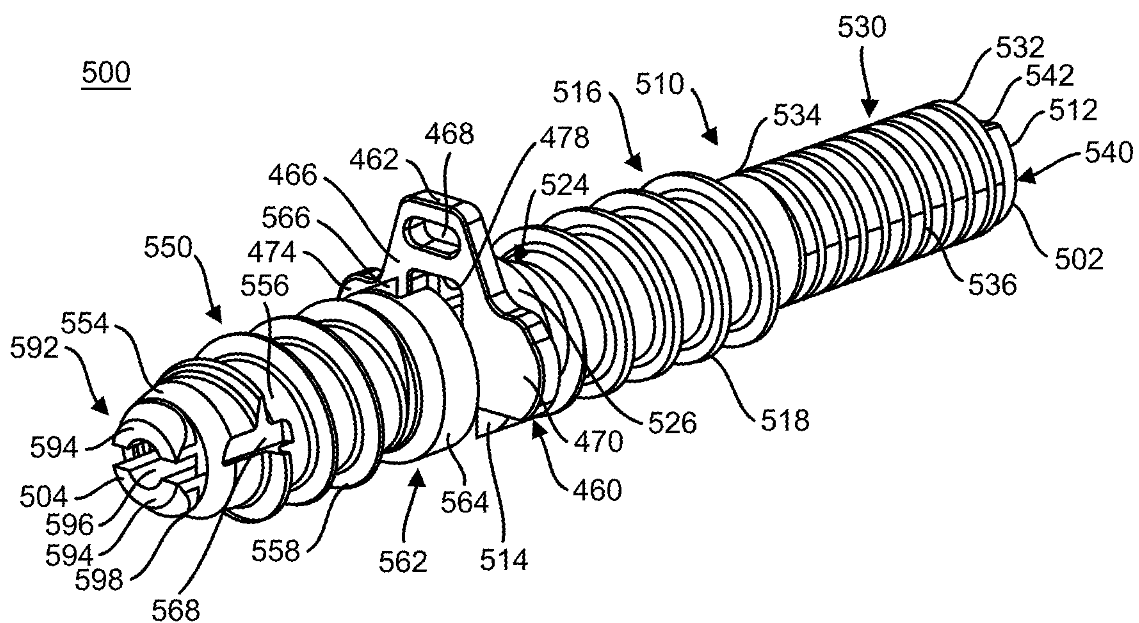
FIG. 51 is another perspective view of the implant of FIG. 50, in accordance with an aspect of the present disclosure.
Figure 52:
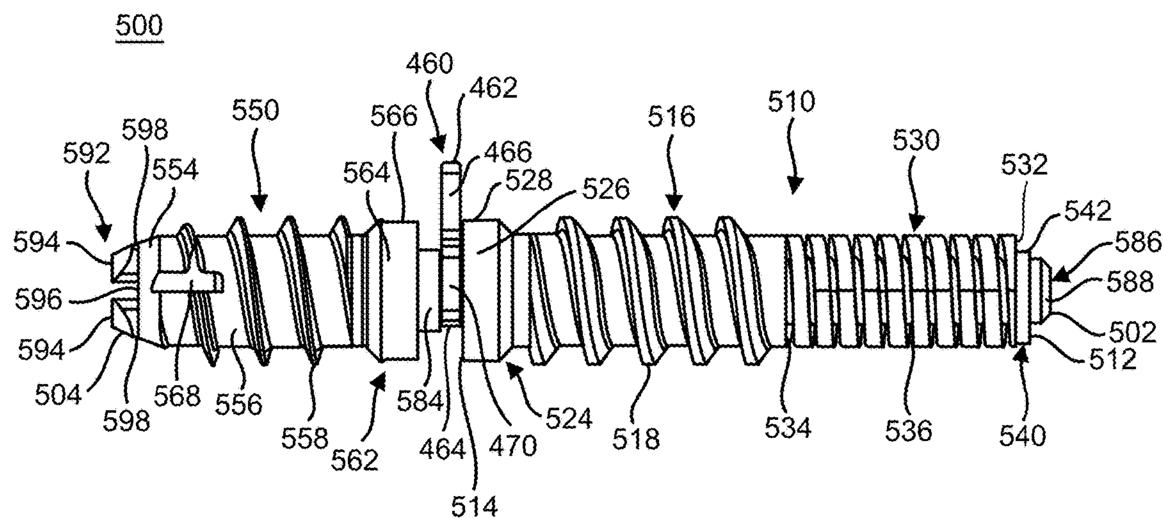
FIG. 52 is a side view of the implant of FIG. 50, in accordance with an aspect of the present disclosure.
Figure 53:
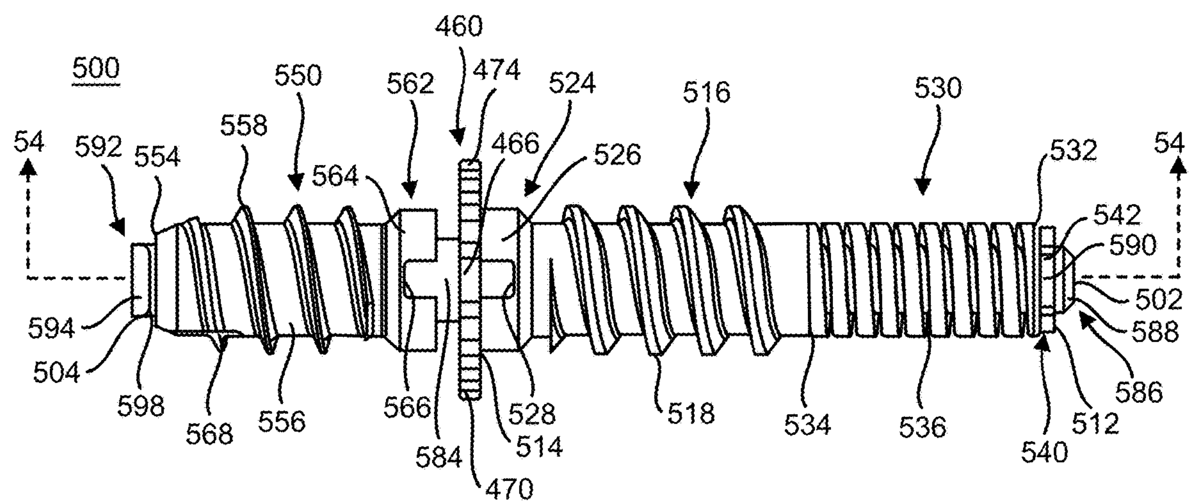
FIG. 53 is a top view of the implant of FIG. 50, in accordance with an aspect of the present disclosure.

Referring now to FIG. 50-67, another implant 500 is shown. The implant 500 includes a first end 502 and a second end 504, as shown in FIG. 50. The implant 500 also includes a first or proximal member 510, a second or distal member 550, a coupling member 580 positioned to engage the first member 510 on one end and the second member 550 on another end, and a biasing member or activation member 460 positioned between the first and second members 510, 550 and engaging the coupling member 580. The components of the implant 500 may be made of, for example, titanium, stainless steel, nitinol, PEEK, or another similar biocompatible material as known by one of ordinary skill in the art.

Figure 54:
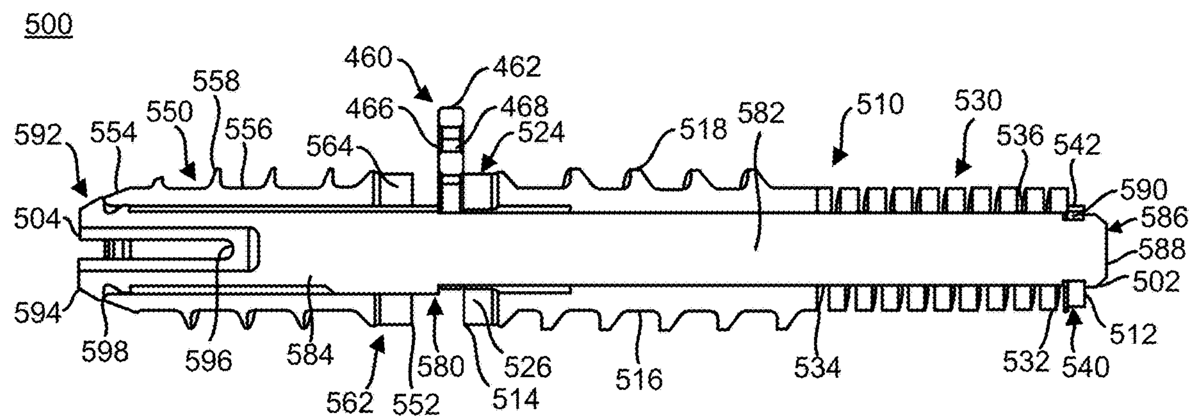
FIG. 54 is a cross-sectional view of the implant of FIG. 50 taken along line 54-54 in FIG. 53, in accordance with an aspect of the present disclosure.
Figure 55:
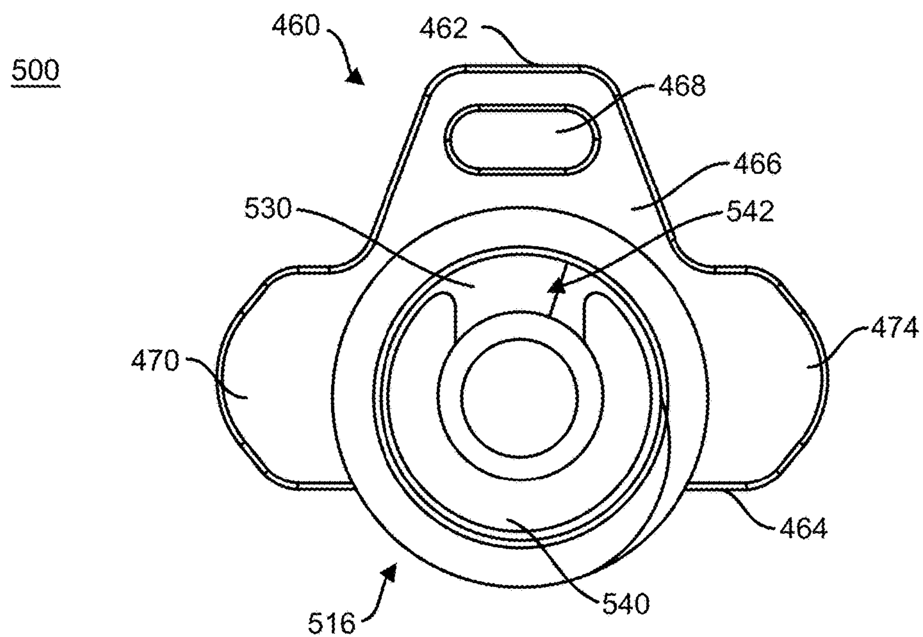
FIG. 55 is an end view of the implant of FIG. 50, in accordance with an aspect of the present disclosure.
Figure 56:
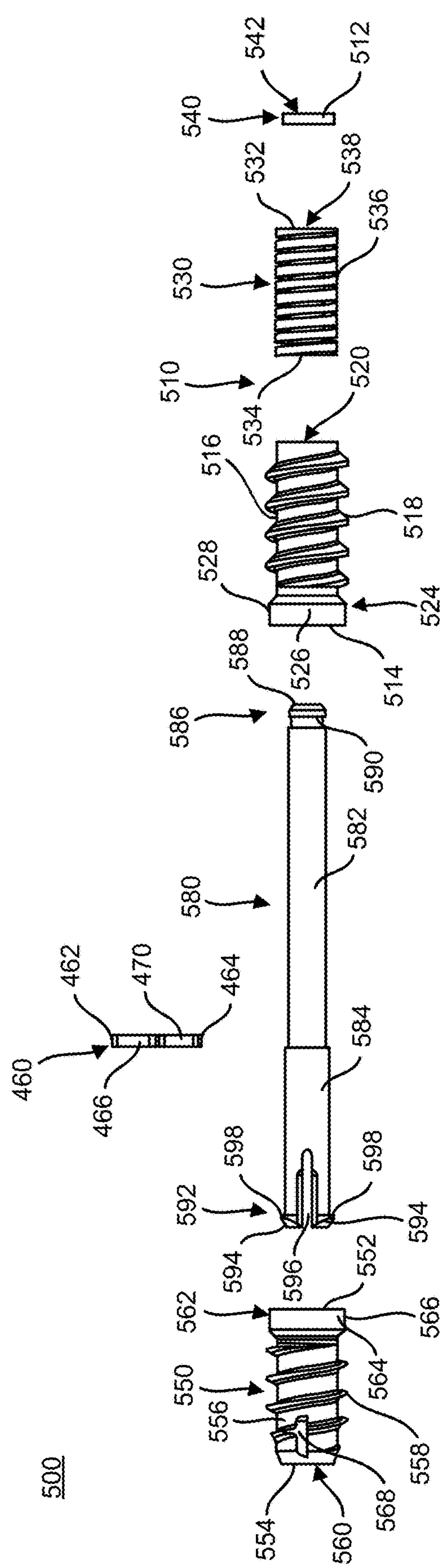
FIG. 56 is an exploded, side view of the implant of FIG. 50, in accordance with an aspect of the present disclosure.
Figure 57:
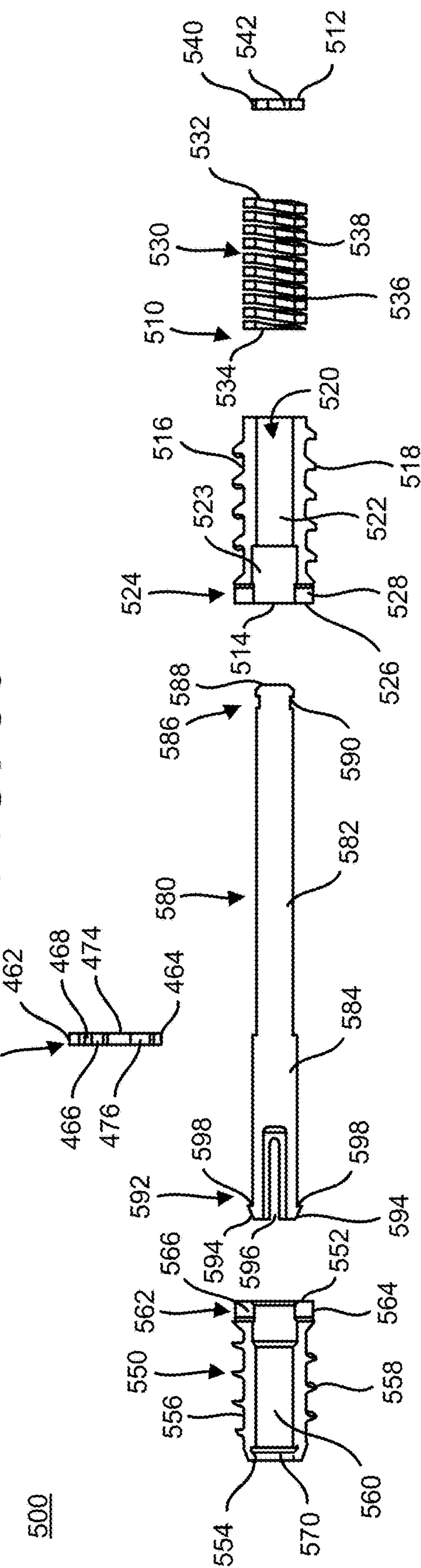
FIG. 57 is an exploded, cross-sectional view of the implant of FIG. 50 taken along line 54-54 in FIG. 53, in accordance with an aspect of the present disclosure.

With continued reference to FIGS. 50-59, 66, and 67, the first or proximal member 510 includes a first end 512 and a second end 514. The first member 510 includes a screw portion or body portion 516, a deformable member, spring member or spring portion 530, and a retaining member or clip 540. As shown in FIGS. 50-54 and 56-59, the screw portion 516 and deformable member 530 are separate components that engage each other when positioned on the coupling member 580. The screw portion 516 is positioned at the second end 514, the retaining member 540 is positioned at the first end 512, and the deformable member 530 is positioned between the screw portion 516 and the retaining member 540. The screw portion 516 may include at least one thread 518 positioned on an exterior surface of the screw portion 516. The screw portion 516 may also include an opening or through hole 520 extending from the second end 514 of the first member 510 through the entire screw portion 516, as shown in FIGS. 54 and 57. The through hole 520 may include, for example, a first portion 522 with a first diameter and a second portion 523 with a second diameter, as shown in FIG. 57. The first portion 522 may be positioned, for example, on the end that engages the deformable member 530. The second portion 523 may be positioned, for example, near the second end 514 of the first member 510. The second diameter may be, for example, larger than the first diameter to allow for the second portion 523 of the through hole 520 to receive at least a portion of the second portion 584 of the coupling member 580. The screw portion 516 of the first member 510 may also include a drive feature or engagement end 524 at the second end 514, as shown in FIGS. 56, 57, 59 and 61. The drive feature 524 may include, for example, at least one protrusion 526 and at least one recess 528. In the depicted embodiment, the drive feature 524 includes two protrusions 526 and two recesses 528, although other numbers of protrusions 526 and recesses 528 are also contemplated.

The deformable member 530 may include a first end 532 and a second end 534, as shown in FIGS. 50-54 and 56-59. The second end 534 may be positioned to engage the screw portion 516, as shown in FIGS. 50-54, 66, and 67. The deformable member 530 may also include a helical opening 536 extending along the length of the deformable member 530. The helical opening 536 may extend from an exterior surface of the deformable member 530 into a through hole 538. The through hole 538 may extend through the deformable member 530 from the first end 532 to the second end 534, as shown in FIGS. 54 and 57. The helical opening 536 may form, for example, a spring allowing for deformation of the deformable member 530 when force is applied. The retaining member 540 may include an opening or passage 542 extending through the retaining member 540, as shown in FIGS. 50, 55, 58, 59, 64 and 65. The opening or passage 542 allows the retaining member 540 to engage the coupling member 580.

Figure 58:
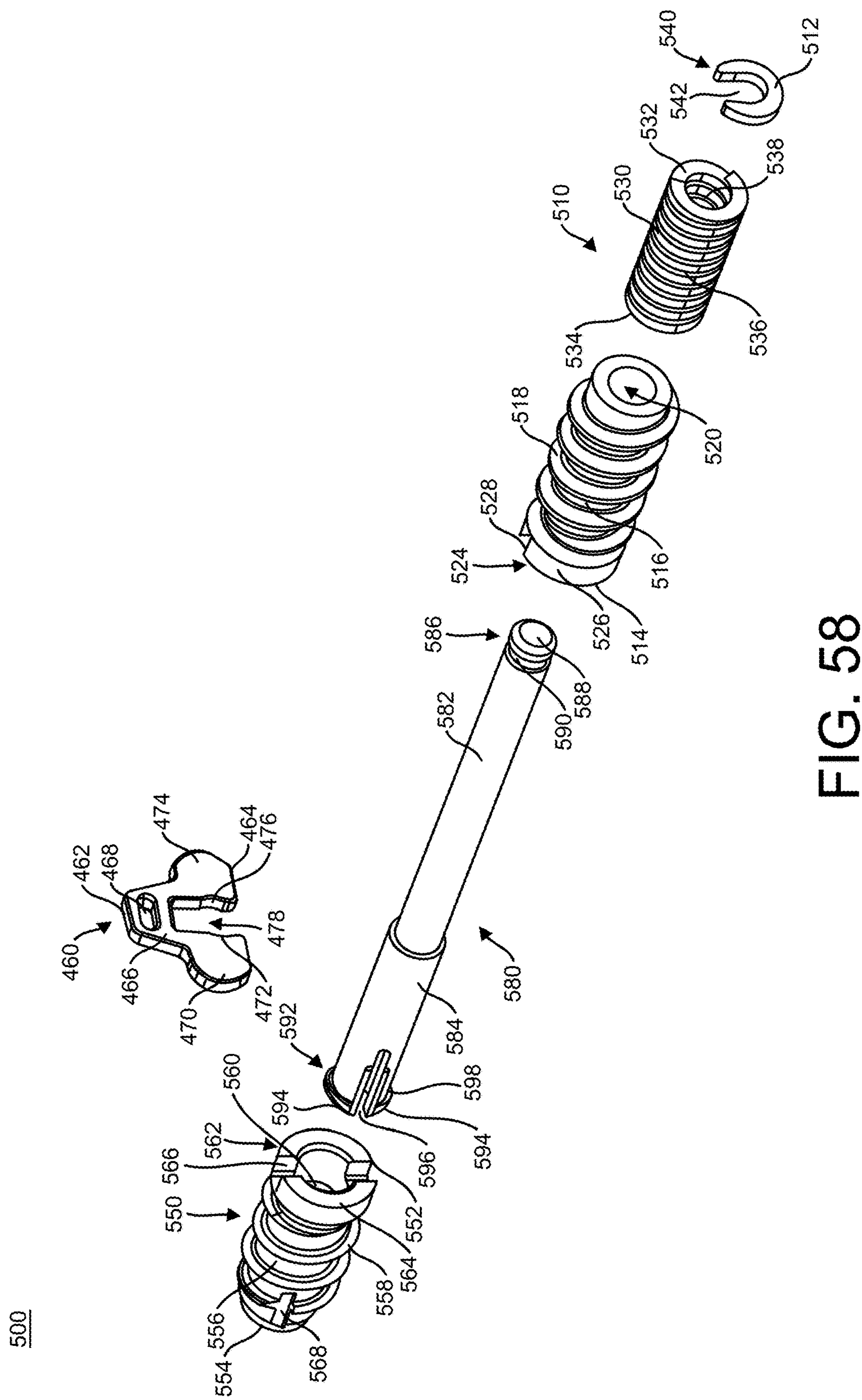
FIG. 58 is an exploded, first end perspective view of the implant of FIG. 50, in accordance with an aspect of the present disclosure.
Figure 59:
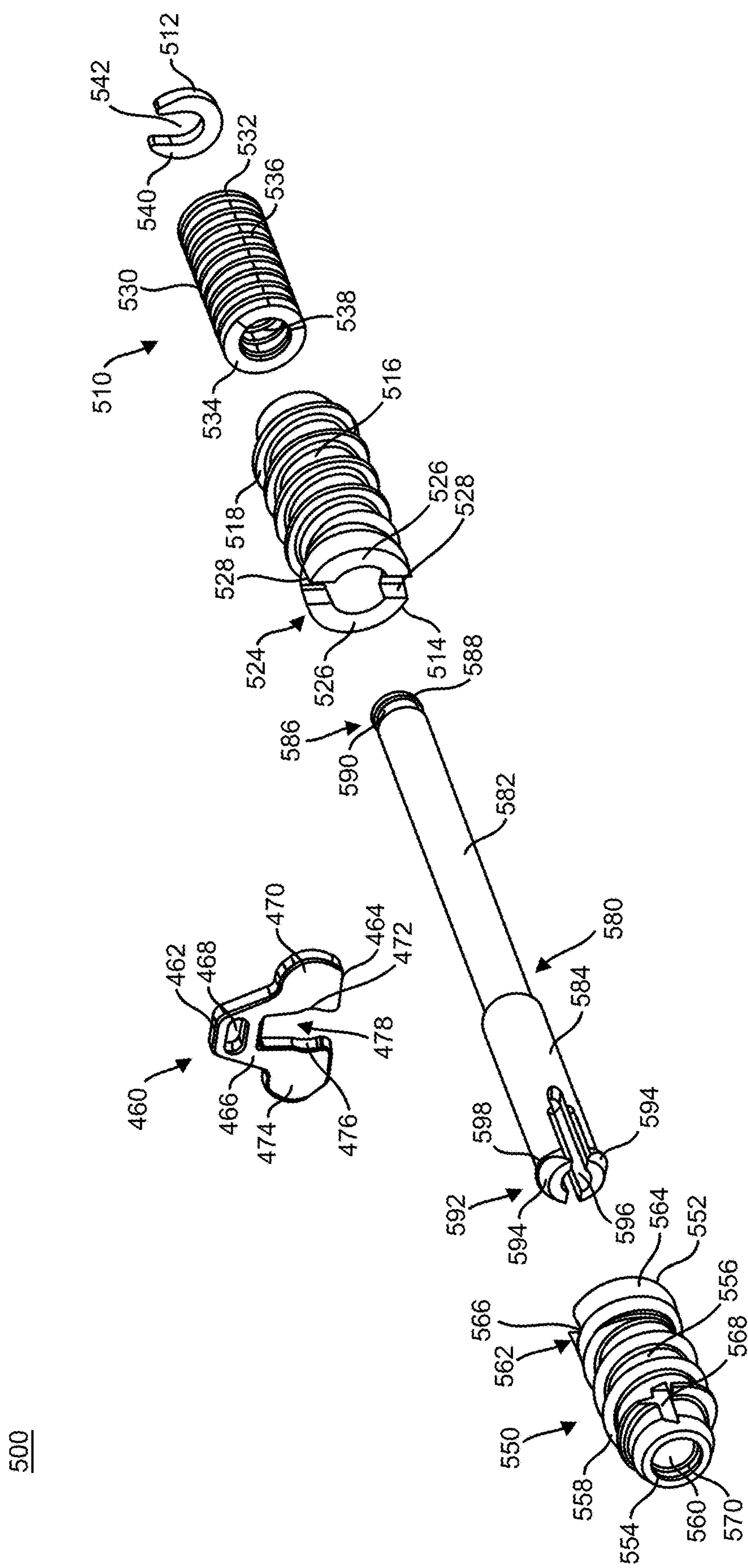
FIG. 59 is an exploded, second end perspective view of the implant of FIG. 50, in accordance with an aspect of the present disclosure.
Figure 60:
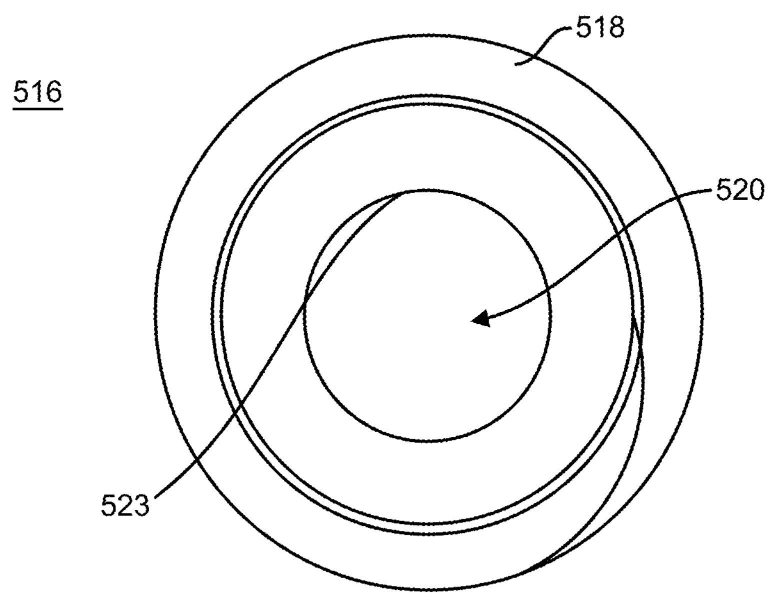
FIG. 60 is a first end view of a screw portion of the implant of FIG. 50, in accordance with an aspect of the present disclosure.
Figure 61:
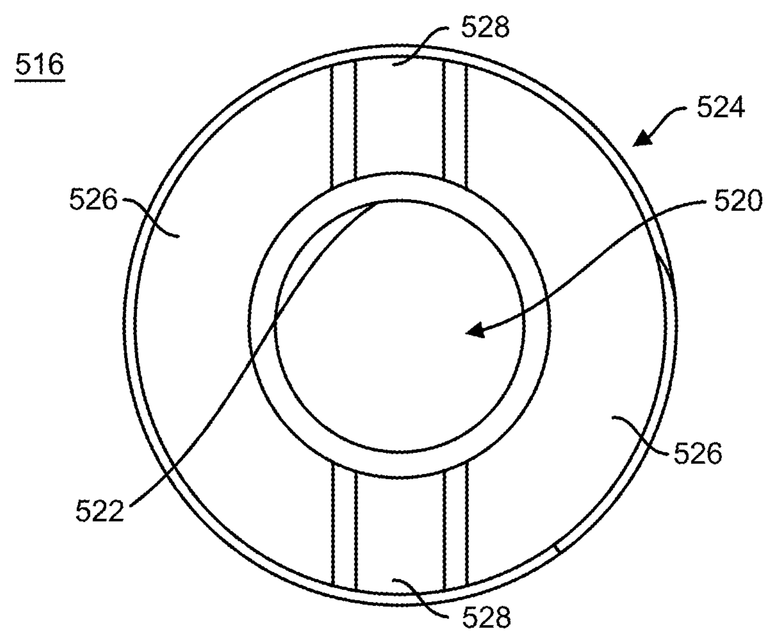
FIG. 61 is a second end view of the screw portion of the implant of FIG. 50, in accordance with an aspect of the present disclosure.
Figure 62:
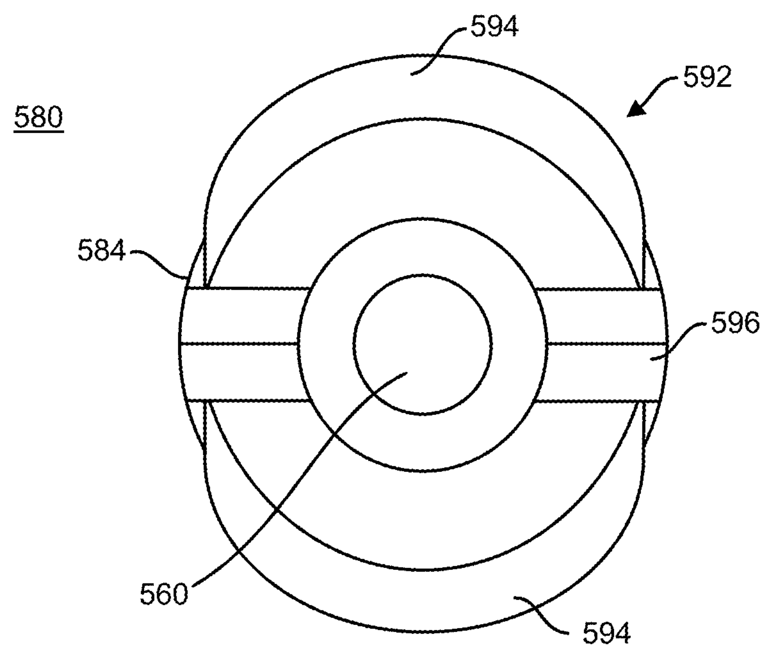
FIG. 62 is an end view of a coupling member of the implant of FIG. 50, in accordance with an aspect of the present disclosure.
Figure 63:
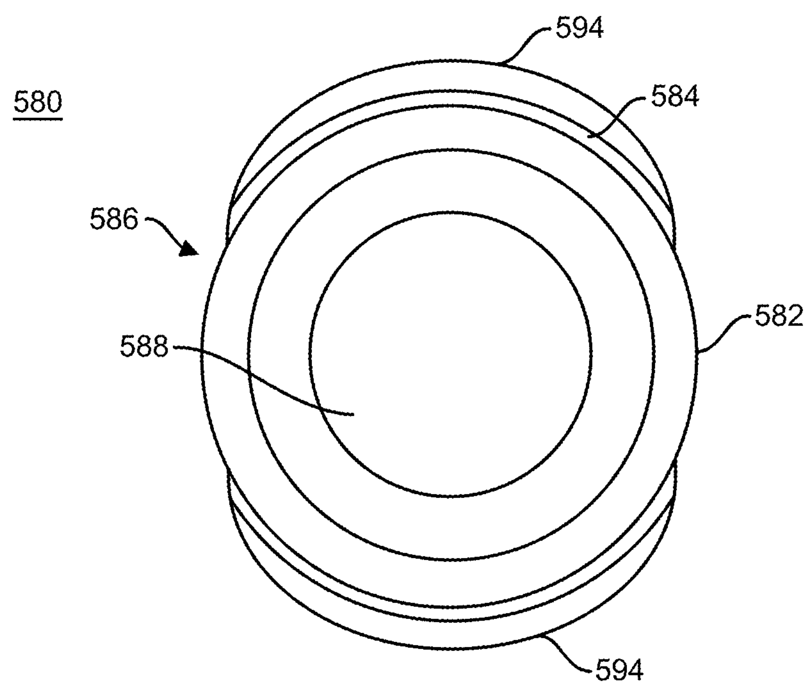
FIG. 63 is another end view of the coupling member of the implant of FIG. 50, in accordance with an aspect of the present disclosure.
Figure 64:
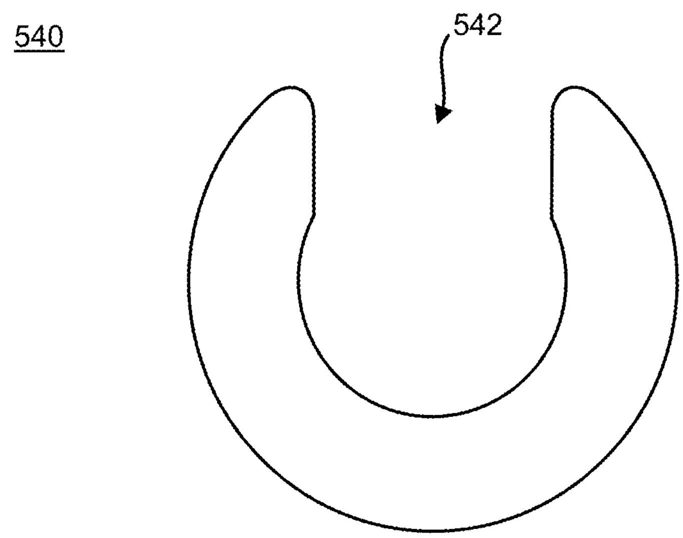
FIG. 64 is an end view of a retaining member of the implant of FIG. 50, in accordance with an aspect of the present disclosure.
Figure 65:
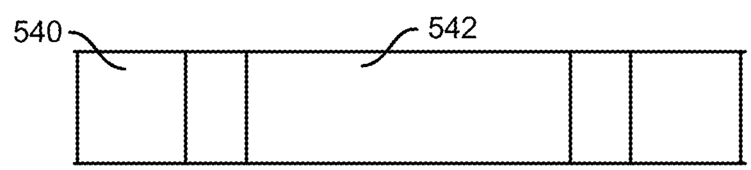
FIG. 65 is a top view of the retaining member of the implant of FIG. 50, in accordance with an aspect of the present disclosure.
Figure 66:
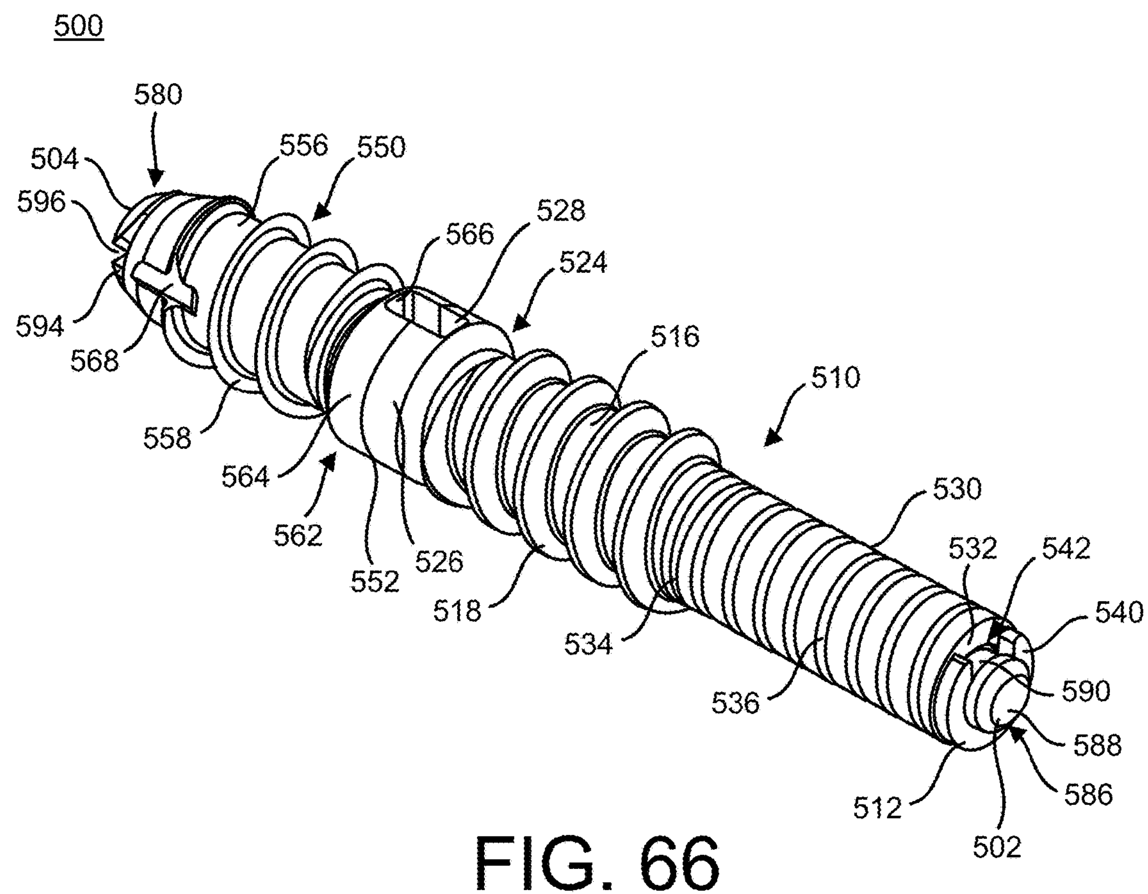
FIG. 66 is a first perspective view of the implant of FIG. 50 after a biasing member is removed, in accordance with an aspect of the present disclosure.
Figure 67:
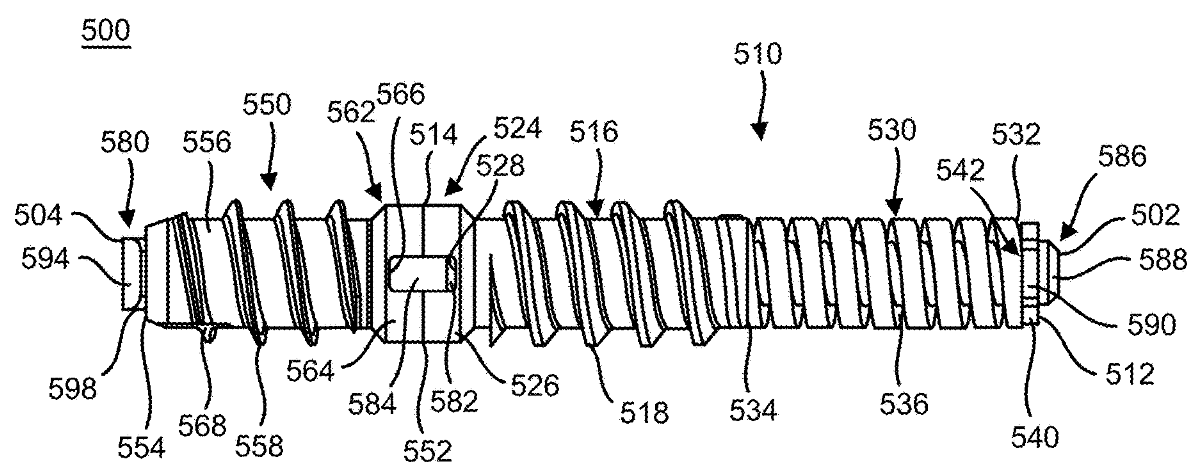
FIG. 67 is a side view of the implant of FIG. 66, in accordance with an aspect of the present disclosure.

Referring now to FIGS. 50-54, 56-59 and 66-67, the second or distal member 550 includes a first end 552 and a second end 554. The second member 550 also includes a body 556 extending between the first end 552 and the second end 554. The body 556 may include at least one thread 558 positioned on an exterior surface of the body 556. The second member 550 may also include an opening or through hole 560 extending between at least a portion of the first end 552 and the second end 554, as shown in FIGS. 54 and 57. As shown FIG. 57, the through hole 560 may include, for example, a first portion near the first end 552 and a second portion near the second end 554. The first portion of the through hole 560 may have a first diameter and the second portion of the through hole 560 may have a second diameter. The first diameter may be, for example, larger than the second diameter. The first portion may extend from the first end 552 into the body 556 and the second portion may extend from the second end 554 into the body 556 until it engages the first portion. The first end 552 of the body 556 may also include a drive feature or engagement end 562, as shown in FIGS. 56-58. The drive feature 562 may include, for example, at least one protrusion or tooth 564 and at least one recess or groove 566. In the depicted embodiment, the drive feature 562 includes two protrusions 564 and two recesses 566, although other numbers of protrusions 564 and recesses 566 are also contemplated. The second end 554 may also include at least one cutting flute 568 recessed into the thread 558 and the body 556 of the second member 550. As shown in FIGS. 50-53, 56, 58, 59 and 66, the second end 554 may include, for example, one cutting flute 568, although other numbers of cutting flutes 568 are also contemplated. The second member 550 may further include at least one groove or engagement channel 570 inset into an interior surface of the body 556 formed by the through hole 560, as shown in FIG. 57.

The coupling member or compression member 580, as shown in FIGS. 54 and 56-59, includes a first portion 582 and a second portion 584. The first portion 582 extends from a first end of the coupling member 580 toward the second end of the coupling member 580. The second portion 584 extends from a second end of the coupling member 580 toward the first end of the coupling member 580. The first portion 582 may have, for example, a first diameter and a first length. The second portion 584 may have, for example, a second diameter and a second length. The first diameter may be, for example, the same size or a different size than the second diameter. In the depicted embodiment, the first diameter is, for example, smaller than the second diameter. The first length may be, for example, the same size or a different size than the second length. In the depicted embodiment, the first length may be, for example, longer than the second length. Although the coupling member 580 is shown as a solid member, it is also contemplated that the coupling member 580 may include, for example, a through hole or cannulation extending from the first end to the second end of the coupling member 580.

The coupling member 580 may also include a proximal snap member 588 at the first end and a distal snap member 592 at the second end, as shown in FIGS. 54 and 56-59. The proximal snap member 588 may include an engagement tab or protrusion 588 extending out circumferentially from the longitudinal axis of the coupling member 580. The proximal snap member 588 may also include a channel or groove 590 recessed into the coupling member 580 near the first end and adjacent to the engagement tab 588. The channel 590 may be, for example, sized and shaped to receive the retaining member 540. The retaining member 540 may be, for example, a C clip or like coupling configured or sized and shaped to engage the channel 590 and secure the screw portion 516 and deformable member 530 to the coupling member 580. The distal snap member 592 may include at least one resilient member or deflecting member 594 extending away from the second portion 584 and at least one channel or groove 596. As shown in the depicted embodiment, the distal snap member 592 may include, for example, two resilient members 594 and one channel 596 extending into the second portion 584 between the two resilient members 594. In addition, each resilient member 594 may include an engagement tab or protrusion 598 positioned near the free end of the resilient member 594 opposite the end of the resilient member 594 coupled to the second portion 584.

The biasing member 460 may be as described above with reference to FIGS. 43-49, which will not be described again here for brevity sake.

Referring now to FIG. 50-54, the implant 500 may be assembled by, for example, inserting the proximal snap member 586 of the coupling member 580 into the through hole 520 of the screw portion 516 of the first member 510. Next, the proximal snap member 586 may be inserted into the through hole 538 of the deformable member 530 of the first member 510. The retaining member 540 may then be coupled to the groove 590 of the proximal snap member 586 of the coupling member 580 to secure the screw portion 516 and deformable member 530 of the first member 510 to the coupling member 580. A biasing member 460 may be inserted to engage the coupling member 580, for example, the first portion 582 of the coupling member 580. The biasing member 460 may be, for example, inserted on the first portion 582 adjacent to the second portion 584 of the coupling member 580 to tension the deformable member 530 of the first member 510 between the screw portion 516 and the retaining member 540 coupled to the groove 590 of the proximal snap member 586 of the coupling member 580. The second portion 584 of the coupling member 580 may then be inserted into the through hole 560 of the second member 550. The distal snap member 592 may be inserted until the engagement tabs 598 are received within the groove 570 of the second member 550 or engage the second end 554 of the second member 550. Once the coupling member 580 is engaged with the first and second members 510, 550, the biasing member 460 may be removed causing the deformable member 530 to apply a compressive load to any two bones coupled to the first and second members 510, 550. After the biasing member 460 is removed, at least a portion of the second portion 584 of the coupling member 580 may be, for example, positioned within the first portion 522 of the through hole 520 of the screw portion 516 of the first member 510.

Figure 68:
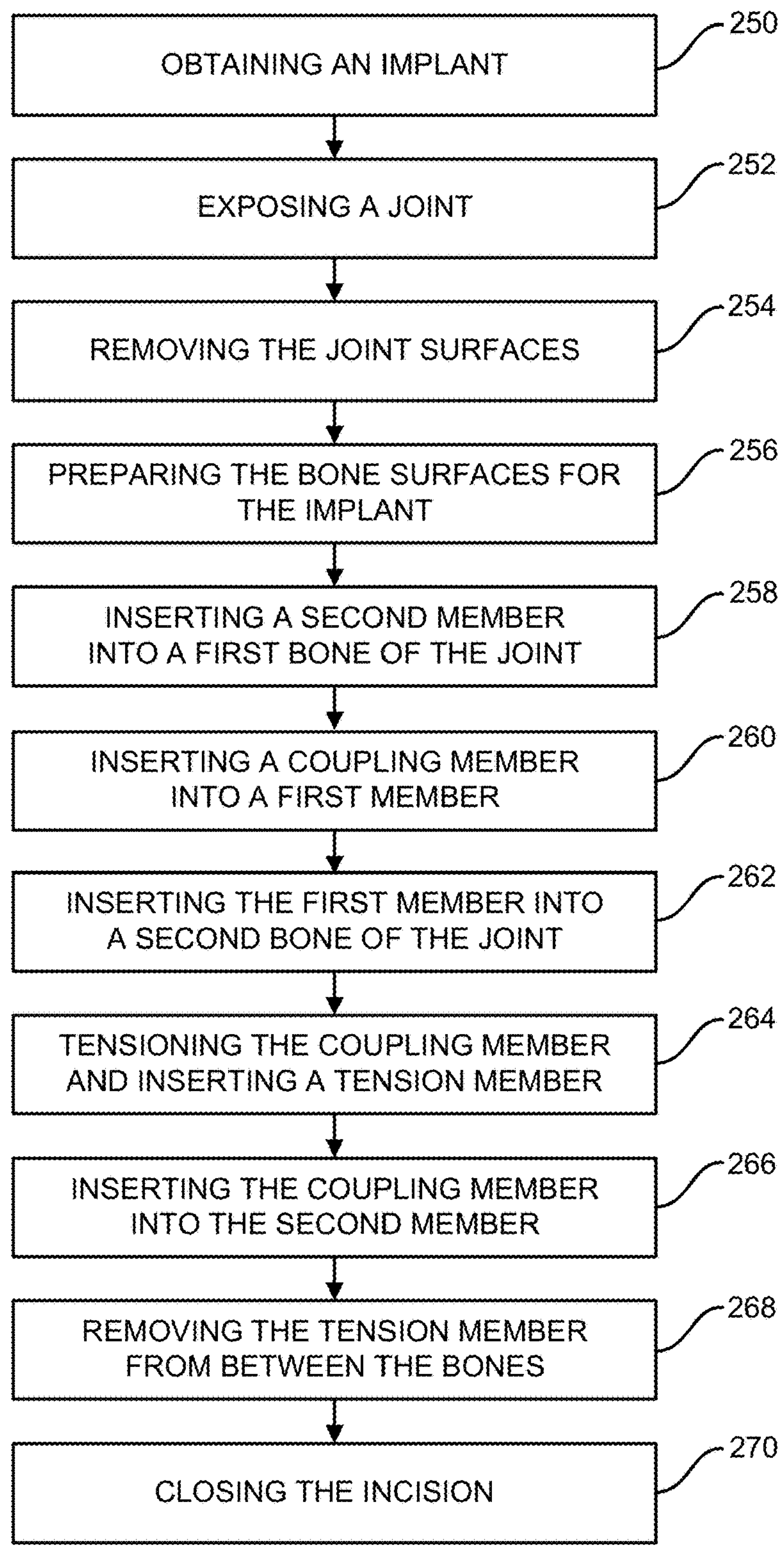
FIG. 68 is a method of using an implant of FIGS. 1, 16, 37 and 50, in accordance with an aspect of the present disclosure.
Figure 69:
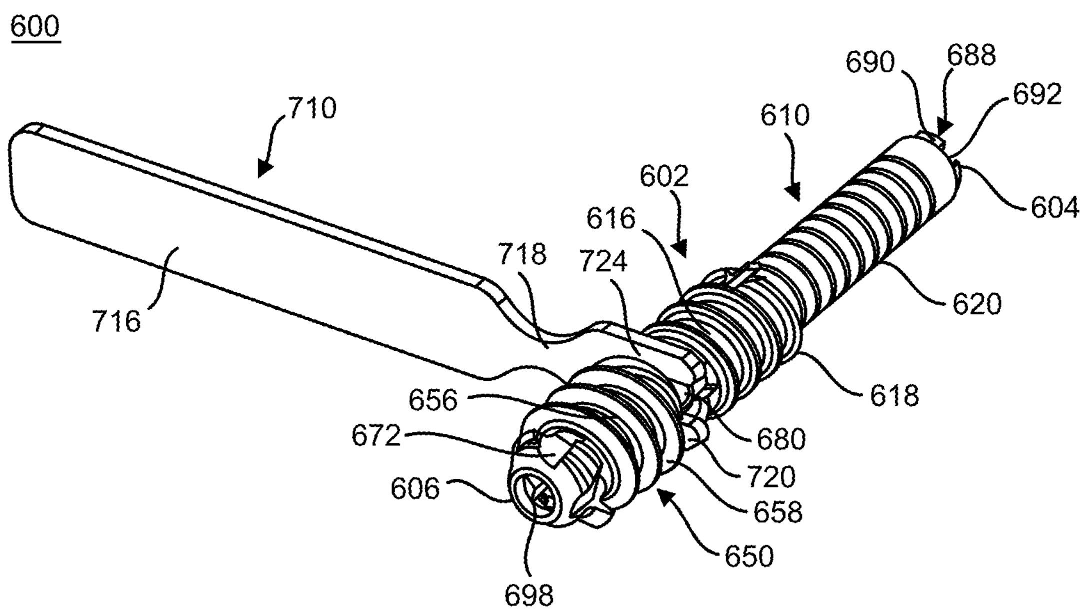
FIG. 69 is a first end perspective view of an implant system, in accordance with an aspect of the present disclosure.

A method of inserting an implant 100, 300, 450, 500 is shown in FIG. 68. The method may include, for example, obtaining an implant 250 and exposing a joint for inserting the implant 252. The method may also include removing the joint surfaces using, for example, a saw, 254. Next, the method may include preparing the bone surfaces for receiving the implant 256. The bone surface may be prepared by, for example, drilling or tapping the bones for inserting the implant. Once the bone surfaces are prepared, the second member may be inserted into a first bone of the joint 258. The second member 150, 350, 550 may be inserted into, for example, the middle phalanx of the affected joint. In an embodiment, the coupling member may be inserted into a first member of the implant 260. The coupling member 180, 380 may be inserted into the first member 110, 310 until the engagement tabs 202, 394 of the proximal snap member 196, 388 mate with the engagement channel 130 or the first end 112, 312 of the first member 110, 310. In another embodiment, the coupling member 180, 380 may come pre-assembled or be coupled to the first member 110, 310 prior to insertion into the patient. Alternatively, the coupling member 580 may be inserted into the screw portion 516 and deformable member 530 of the first member 510 until the groove 590 of the proximal snap member 586 extends beyond the first end 532 of the deformable member 530 and a retaining member 540 may be inserted into the groove 590. Next, the mated coupling member and first member may be inserted into a second bone of the joint 262 and the coupling member may be tensioned by inserting a biasing member onto the coupling member 264. Then, the coupling member may be inserted into the second member 266 and the biasing member may be removed from between the two bones to allow for compression 268. Finally, the method may include closing the incision.

If removal of the implant 100, 300, 450, 500 is desired, the joint may be exposed and distracted. Then, the coupling member 180, 380, 580 may be cut allowing for the first member 110, 310, 510 and second member 150, 350, 550 to be removed with a driver instrument, for example, the driver instrument that was used to insert the first and second members 110, 310, 510, 150, 350, 550.

Referring now to FIGS. 69-118, an implant system 600 is shown. The implant system 600 may include an implant 602 and a compression member or retention clip 710, 730. The retention clip 710, 730 is, for example, non-implantable in the present embodiments although it is contemplated that an alternative retention clip could be implantable. The implant system 600 may also optionally include a proximal driver 740, as shown in FIGS. 94-103, and a distal driver 780, as shown in FIGS. 104-111. The implant 602 may include a first or proximal member 610, a second or distal member 650, and a coupling member or tension member 680. The coupling member 680 is positioned to engage the first member 610 on one end and the second member 650 on another end. The implant 602 may also have a first end 604 and a second end 606. The first member 610 may be positioned, for example, at the first end 604 and the second member 650 may be positioned, for example, at the second end 606. The first member 610, second member 650, and coupling member 680 may be the same or similar to the first member 310, second member 350, and coupling member 380 of implant 300, which are described above and will not be described in complete detail again here for brevity sake. The components of the implant system 600 may be made of, for example, titanium, stainless steel, nitinol, PEEK, or another similar biocompatible material, as known by one of ordinary skill in the art.

Figure 70:
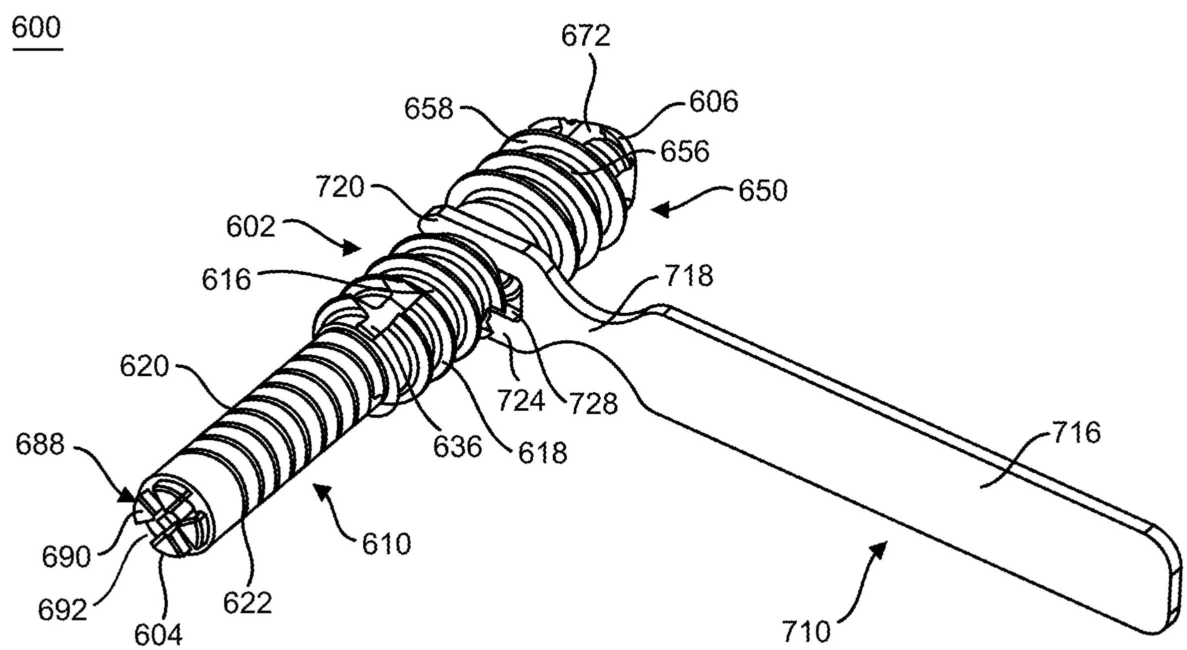
FIG. 70 is a second end perspective view of the implant system of FIG. 69, in accordance with an aspect of the present disclosure.
Figure 71:
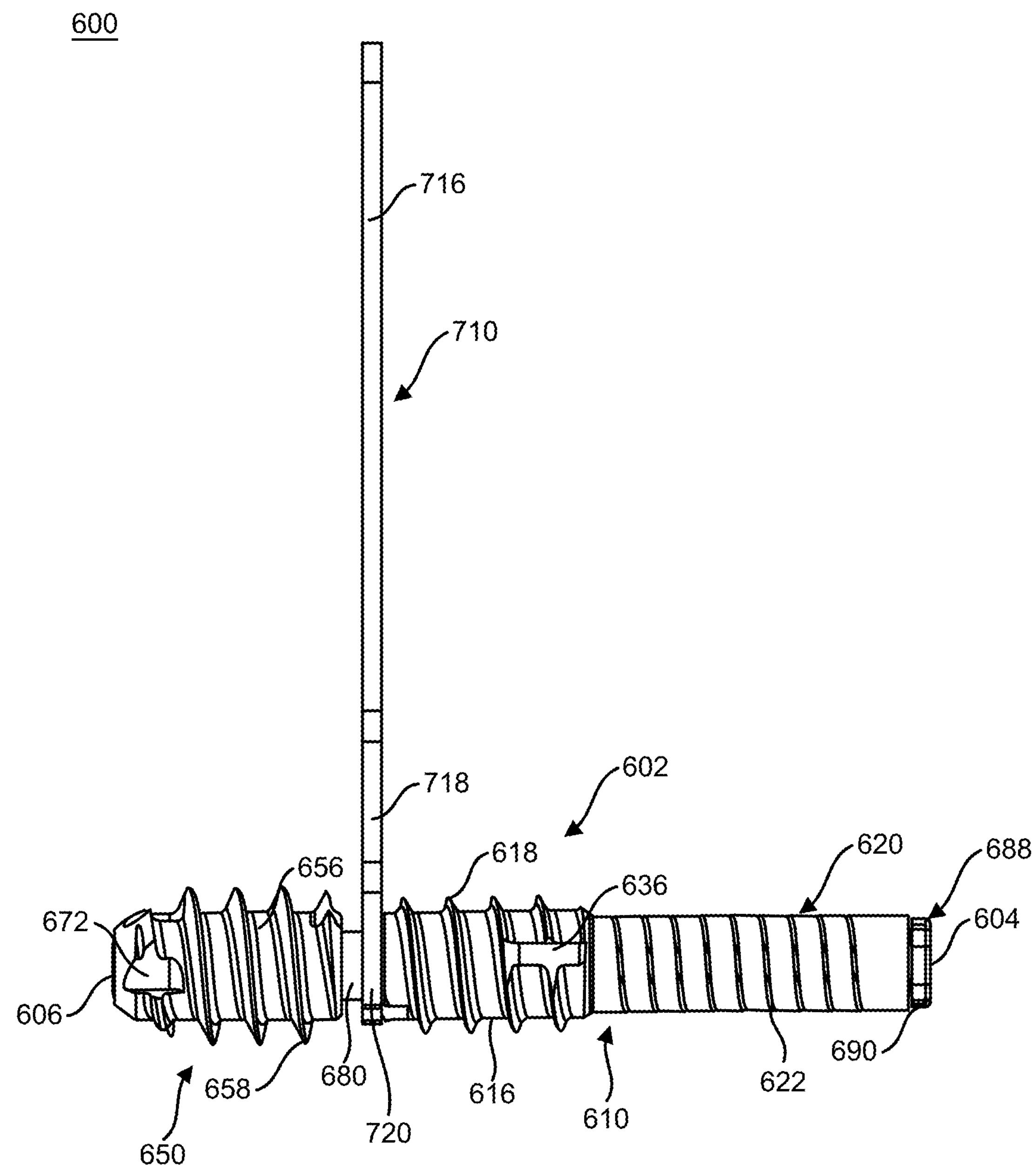
FIG. 71 is a first side view of the implant system of FIG. 69, in accordance with an aspect of the present disclosure.
Figure 72:
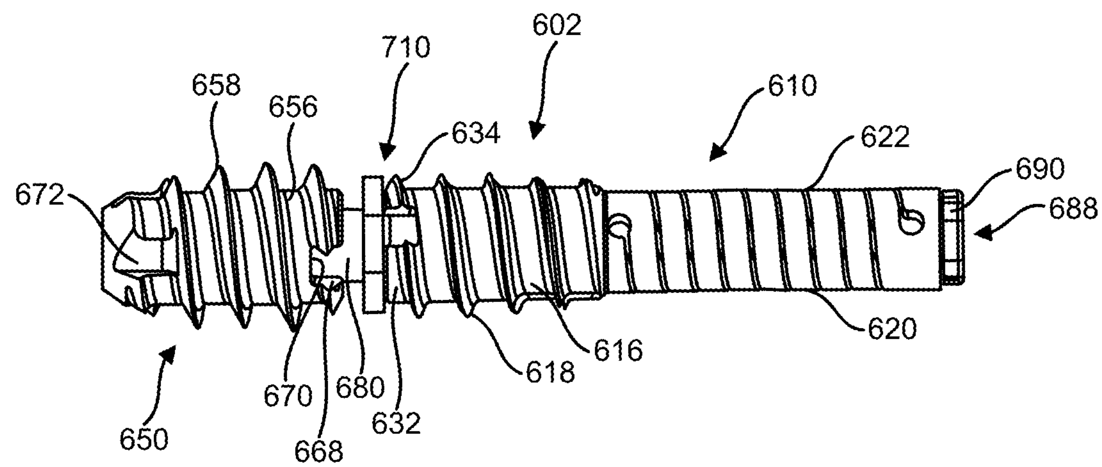
FIG. 72 is a second side view of the implant system of FIG. 69, in accordance with an aspect of the present disclosure.
Figure 73:
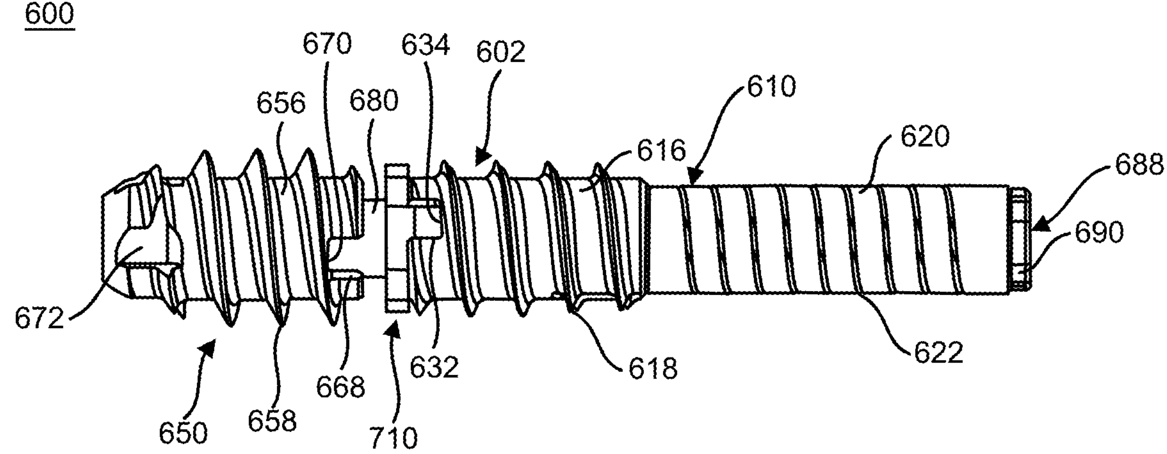
FIG. 73 is a third side view of the implant system of FIG. 69, in accordance with an aspect of the present disclosure.
Figure 74:
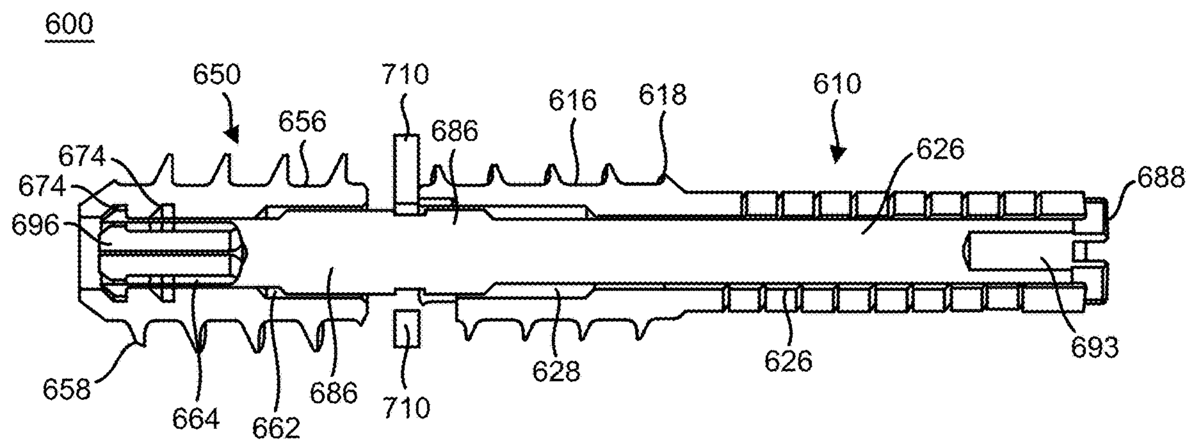
FIG. 74 is a cross-sectional view of the implant system of FIG. 69 taken along line 74-74 in FIG. 75, in accordance with an aspect of the present disclosure.
Figure 75:
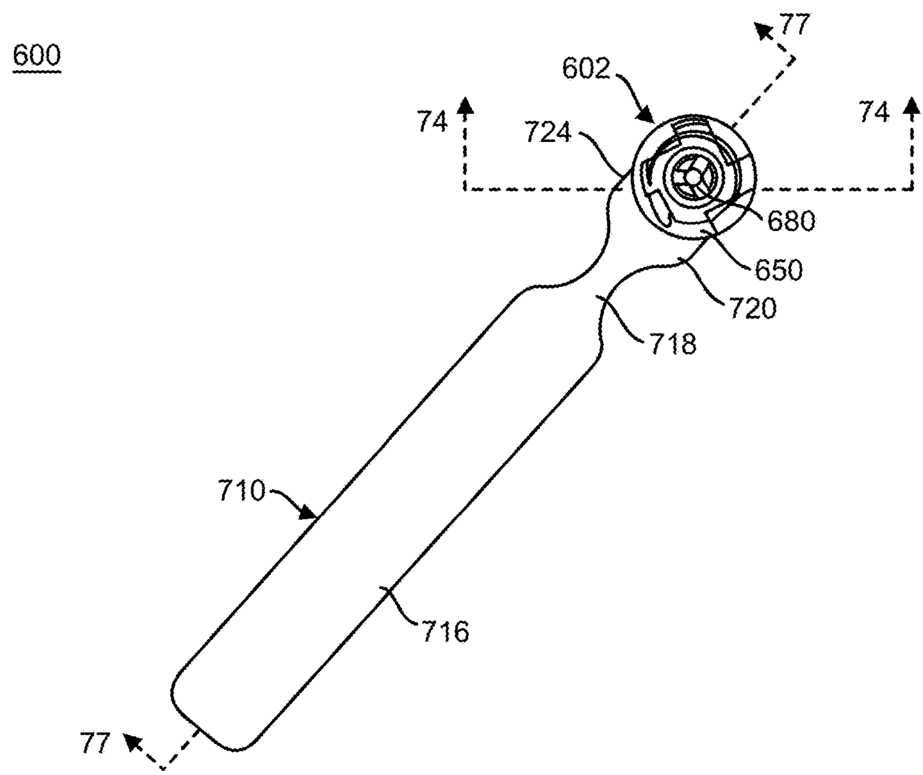
FIG. 75 is a first end view of the implant system of FIG. 69, in accordance with an aspect of the present disclosure.
Figure 76:
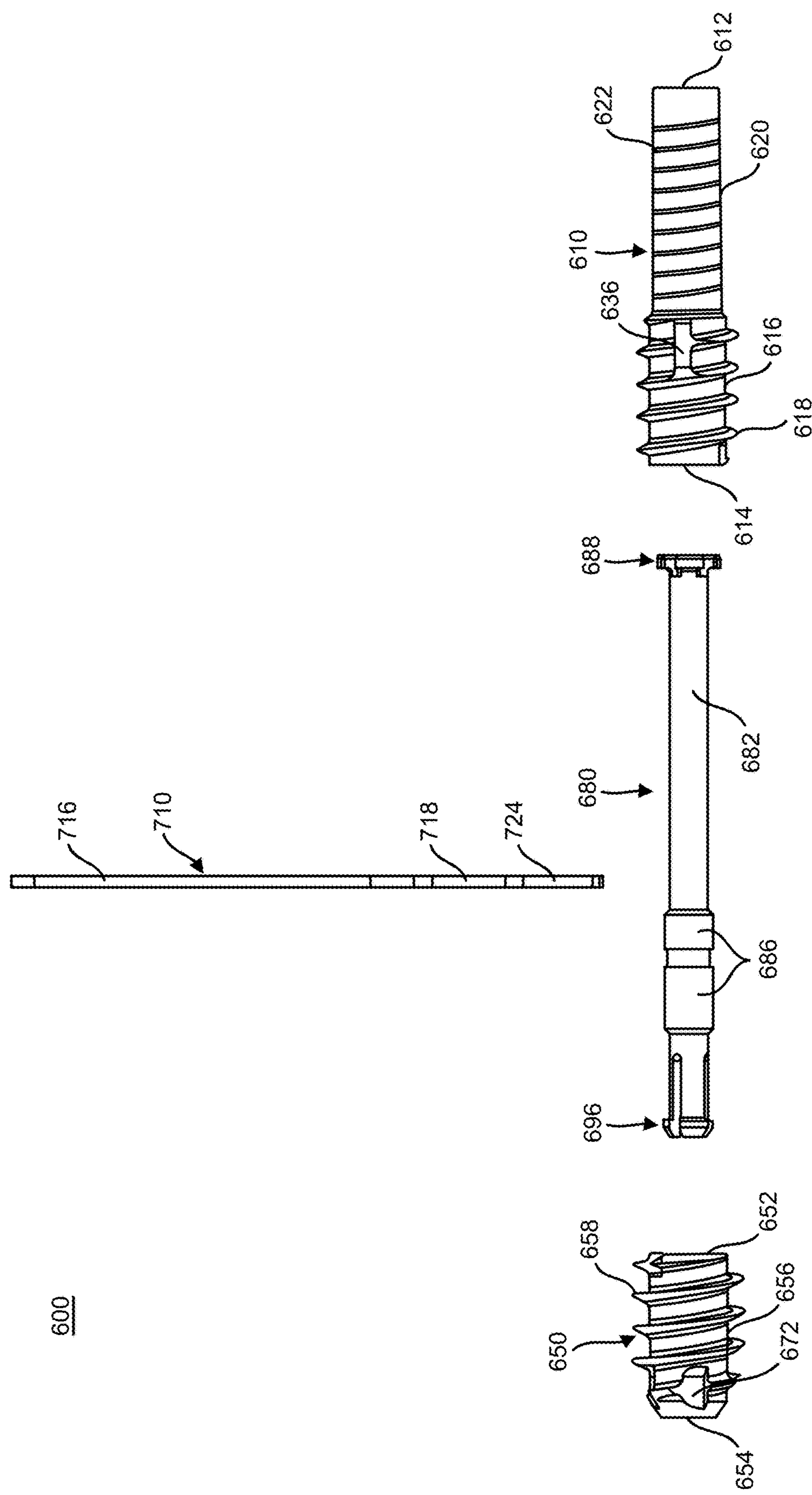
FIG. 76 is an exploded, side view of the implant system of FIG. 69, in accordance with an aspect of the present disclosure.
Figure 77:
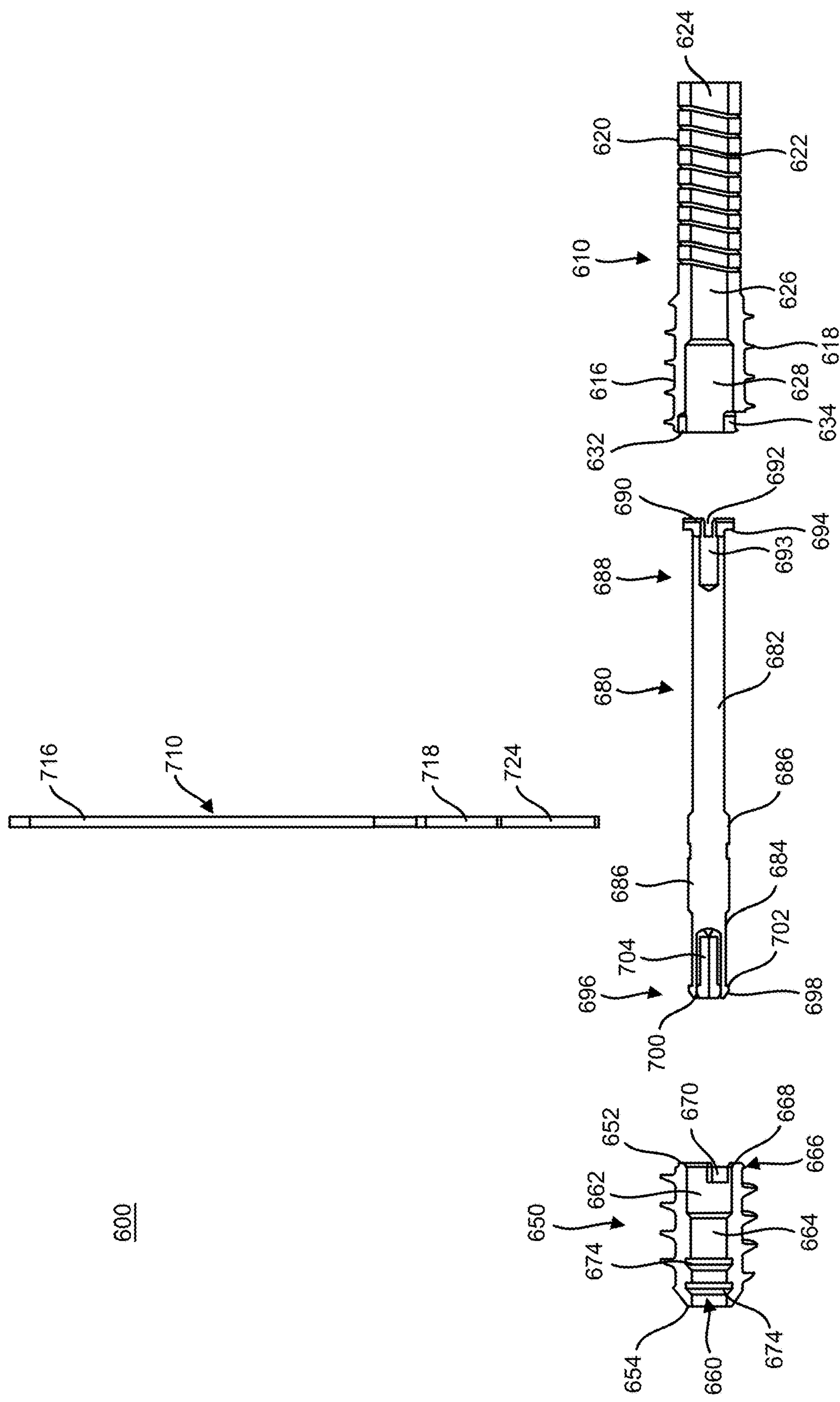
FIG. 77 is an exploded, cross-sectional view of the implant system of FIG. 69 taken along line 77-77 in FIG. 75, in accordance with an aspect of the present disclosure.
Figure 78:
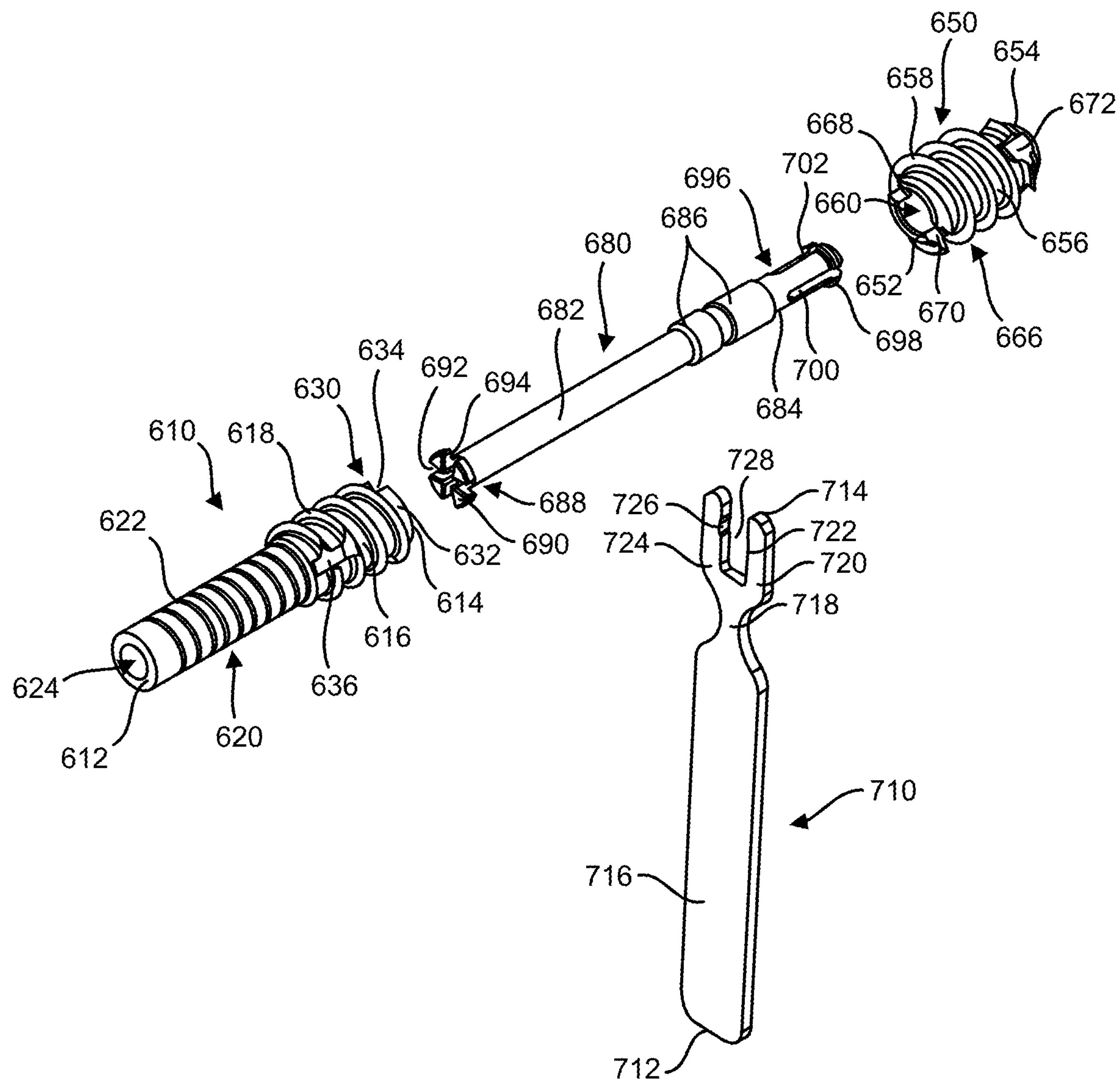
FIG. 78 is an exploded, second end view of the implant system of FIG. 69, in accordance with an aspect of the present disclosure.
Figure 79:
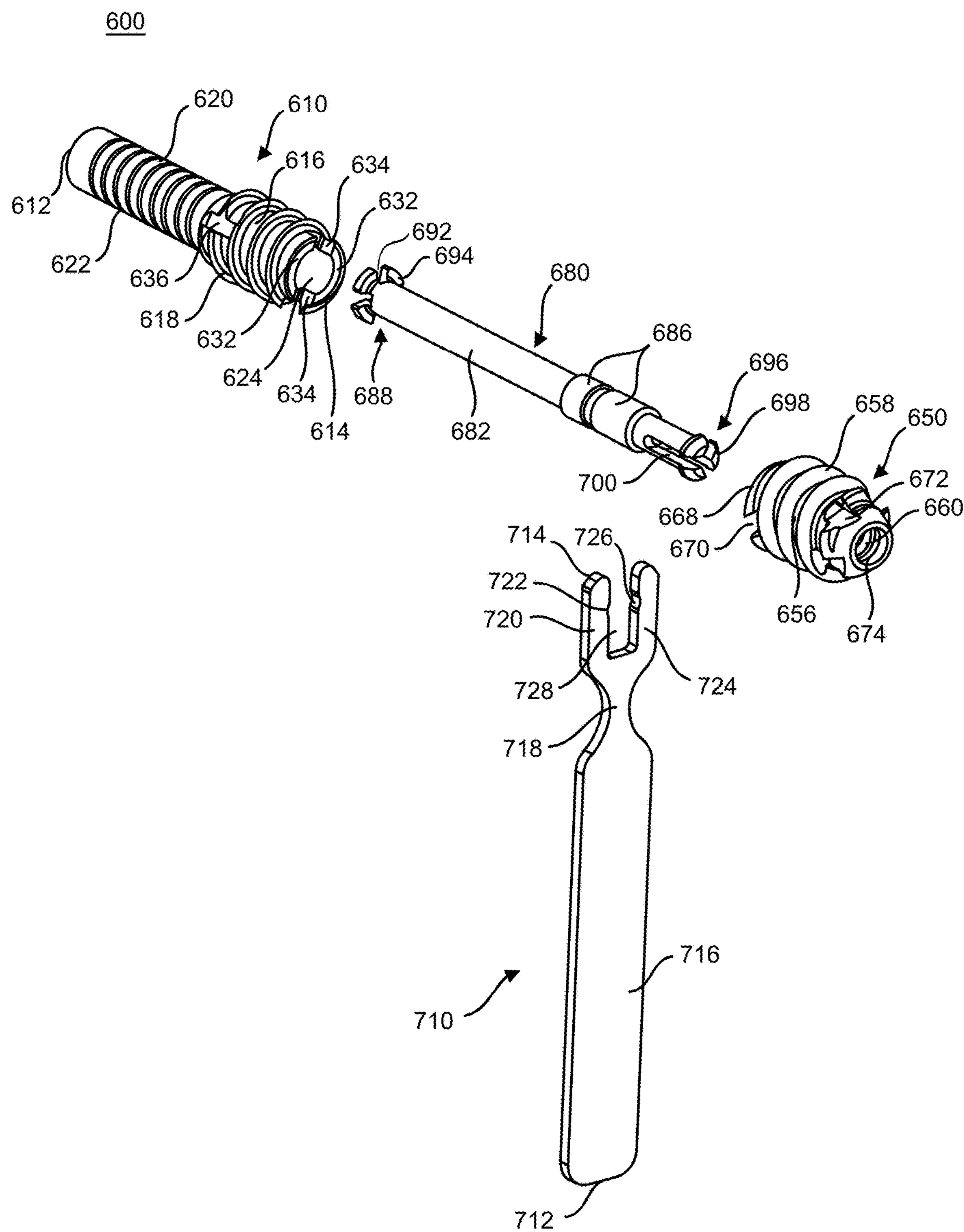
FIG. 79 is an exploded, first end view of the implant system of FIG. 69, in accordance with an aspect of the present disclosure.
Figure 80:
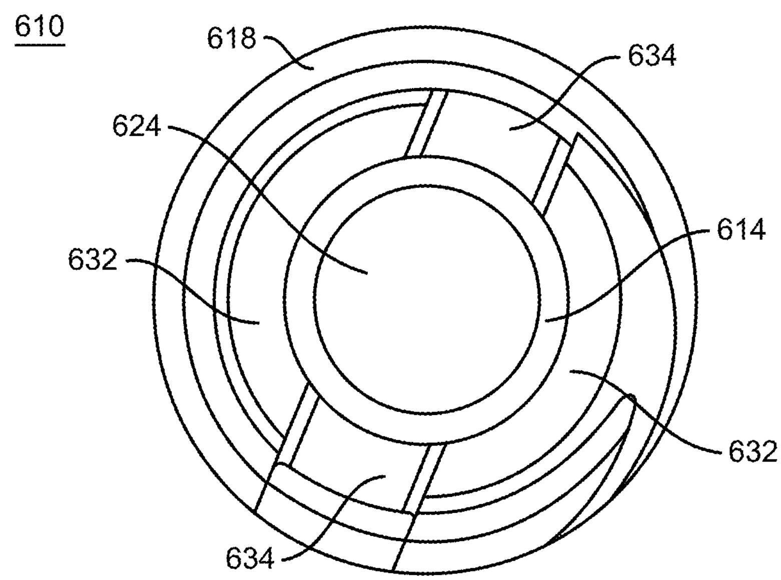
FIG. 80 is a first end view of a first member of the implant system of FIG. 69, in accordance with an aspect of the present disclosure.
Figure 81:
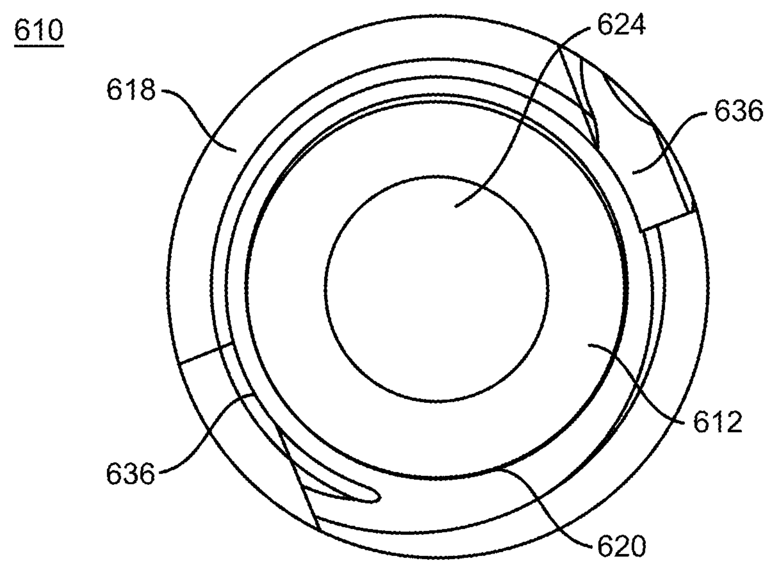
FIG. 81 is a second end view of the first member of FIG. 80, in accordance with an aspect of the present disclosure.

As shown in FIGS. 76-79, the first or proximal member 610 includes a first end 612 and a second end 614. The first member 610 also includes a body portion 616 coupled to or integral with a deformable member, spring member or spring portion 620. In the depicted embodiment of FIGS. 69-79, the body portion 616 and deformable member 620 are coupled together to form a one-piece construct. The one-piece construct may be, for example, monolithic. It is also contemplated that the body portion 616 and deformable member 620 could be, for example, at least two separate pieces that engage when assembled to form the first member 610. The body portion 616 extends from the second end 614 toward the first end 612, the deformable member 620 extends from the first end 612 toward the second end 614, and the body portion 616 transitions to the deformable member 620 at a point between the first and second ends 612, 614. The first member 610 may also include an opening or through hole 624 extending from the first end 612 to the second end 614, as shown in FIGS. 74 and 77. The through hole 624 may include, for example, a first portion 626 with a first diameter and a second portion 628 with a second diameter, as shown in FIG. 77. The first portion 626 may be positioned, for example, inside of the deformable member 620. The second portion 628 may be positioned, for example, inside of the body portion 616. The body portion 616 may include at least one thread 618 positioned on an exterior surface of the body portion 616. The deformable member 620 may include a helical opening or continuous helical opening 622 extending along the length of the deformable member 620. The helical opening 622 may extend from an exterior surface of the deformable member 620 into the through hole 624, as shown in FIGS. 70, 77, and 79. The helical opening 622 may form, for example, a spring portion allowing for deformation of the deformable member 620 when force is applied. The body portion 616 of the first member 610 may also include a drive feature or engagement end 630 at the second end 614, as shown in FIGS. 74 and 77-80. The drive feature 630 may include, for example, at least one protrusion 632 and at least one recess 634. In the depicted embodiment, the drive feature 630 includes two protrusions 632 and two recesses 634, although other numbers of protrusions 632 and recesses 634 are also contemplated.

Figure 82:
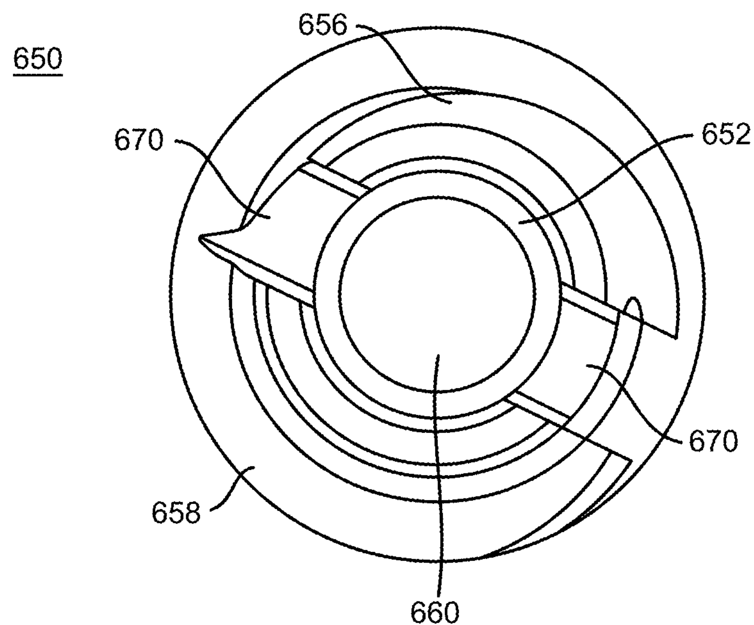
FIG. 82 is a first end view of a second member of the implant system of FIG. 69, in accordance with an aspect of the present disclosure.
Figure 83:
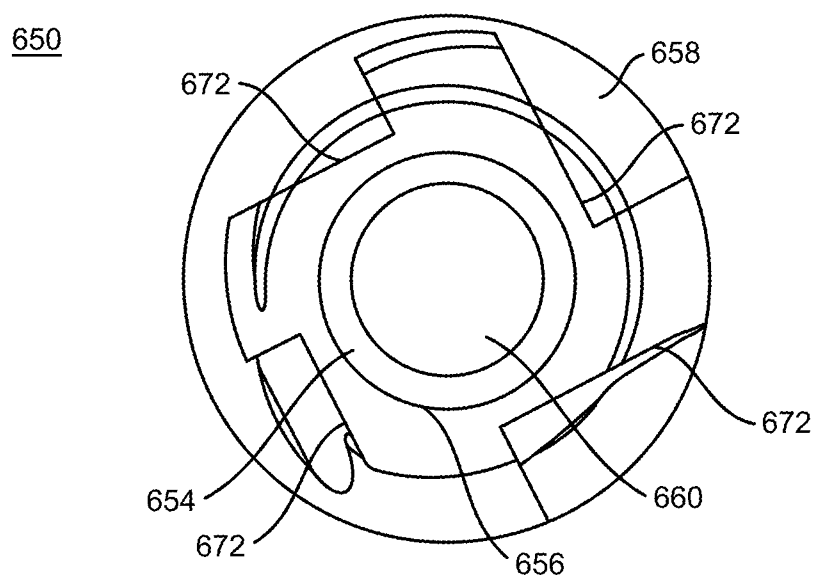
FIG. 83 is a second end view of the second member of FIG. 82, in accordance with an aspect of the present disclosure.
Figure 84:
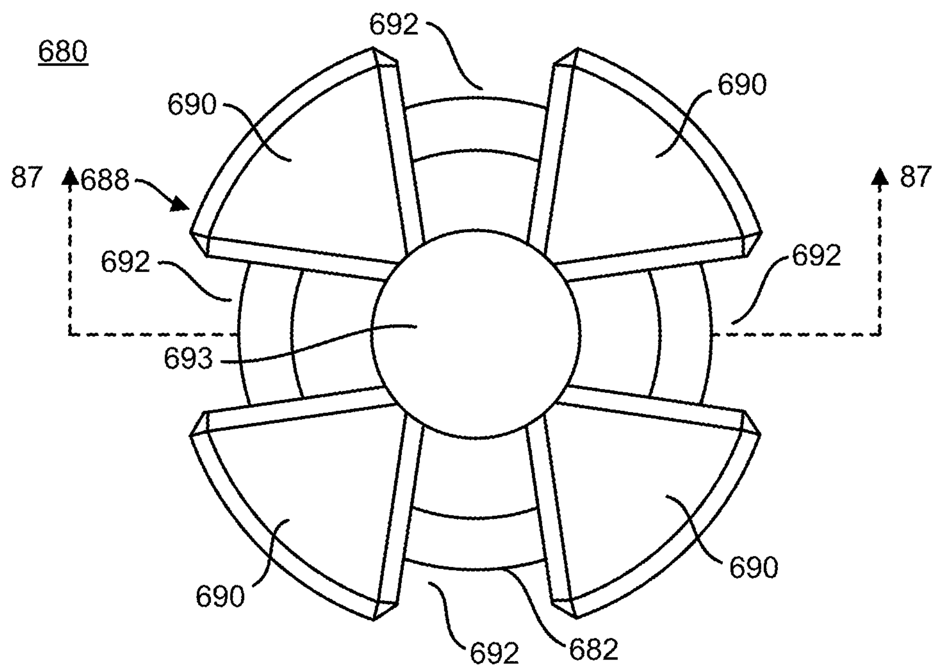
FIG. 84 is a first end view of a coupling member of the implant system of FIG. 69, in accordance with an aspect of the present disclosure.
Figure 85:
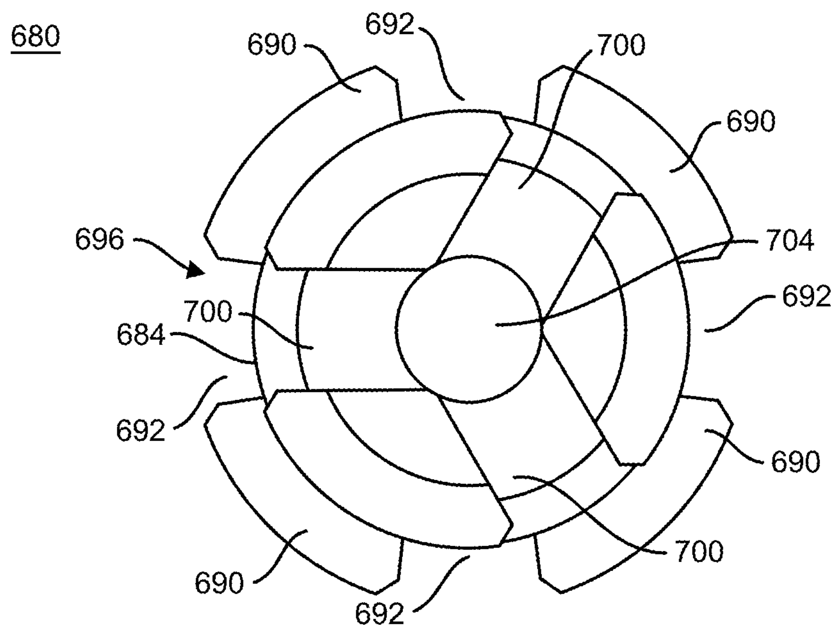
FIG. 85 is a second end view of the coupling member of FIG. 84, in accordance with an aspect of the present disclosure.
Figure 86:
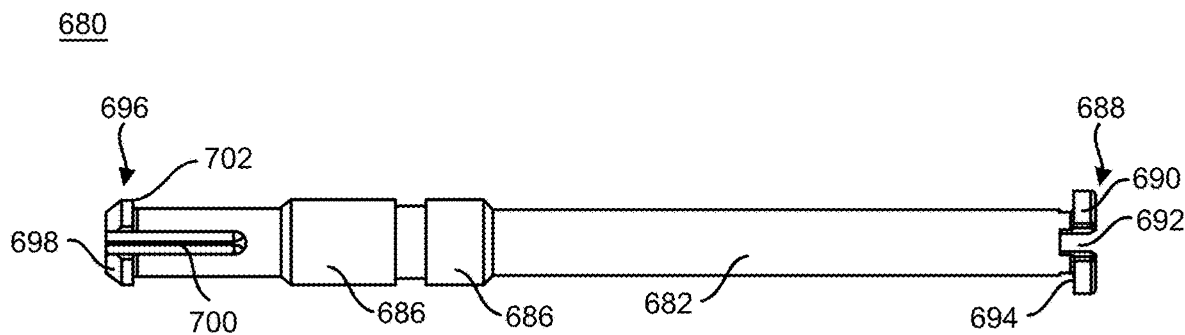
FIG. 86 is a side view of the coupling member of FIG. 84, in accordance with an aspect of the present disclosure.
Figure 87:
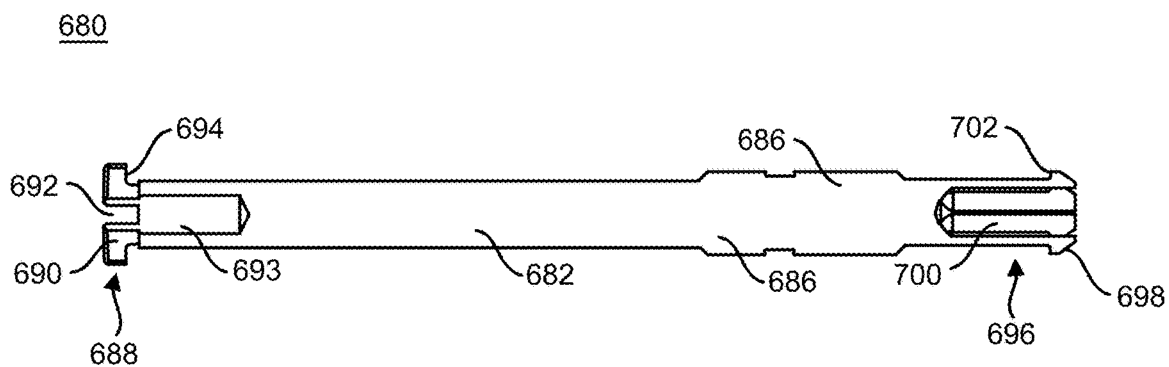
FIG. 87 is a cross-sectional view of the coupling member of FIG. 84 taken along line 87-87 in FIG. 84, in accordance with an aspect of the present disclosure.
Figure 88:
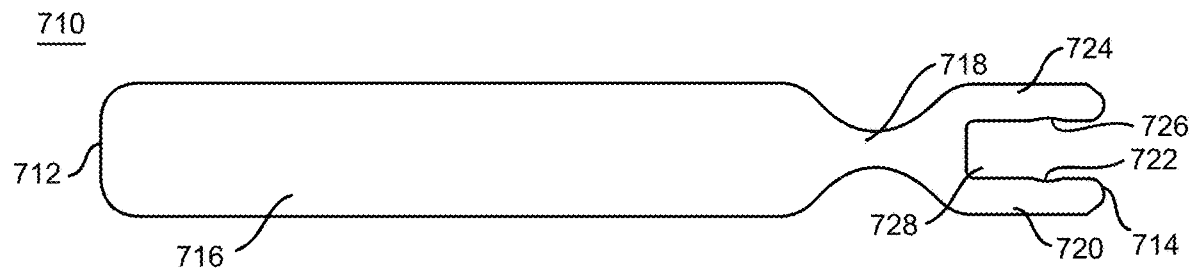
FIG. 88 is a top view of a retention clip of the implant system of FIG. 69, in accordance with an aspect of the present disclosure.
Figure 89:
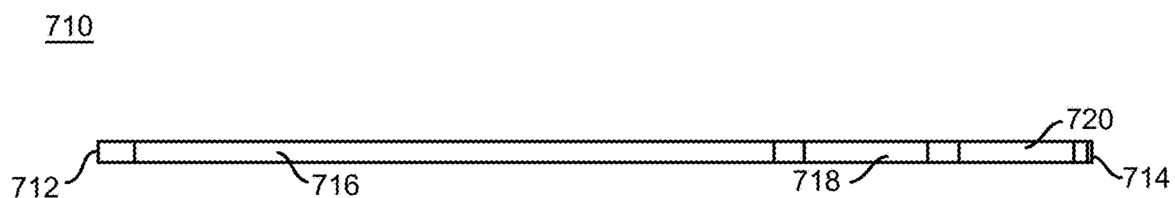
FIG. 89 is a side view of the retention clip of FIG. 88, in accordance with an aspect of the present disclosure.
Figure 90:
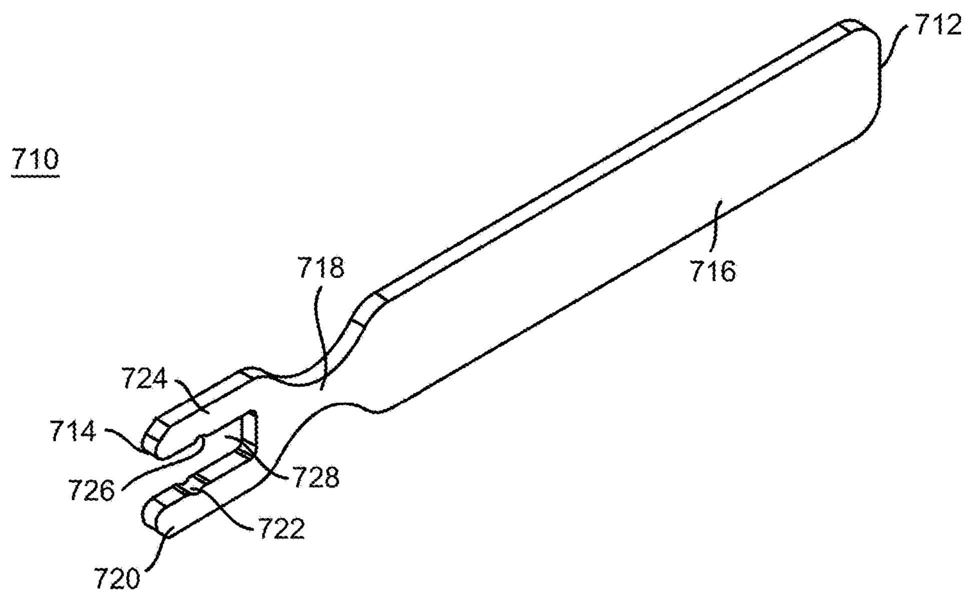
FIG. 90 is a perspective view of the retention clip of FIG. 88, in accordance with an aspect of the present disclosure.

Referring now to FIGS. 69-74 and 76-79, the second or distal member 650 includes a first end 652 and a second end 654. The second member 650 also includes a body 656 extending between the first end 652 and the second end 654. The body 656 may include at least one thread 658 positioned on an exterior surface of the body 656. The second member 650 may also include an opening or through hole 660 extending from the first end 652 to the second end 654, as shown in FIG. 77. The through hole 660 may include, for example, a first portion 662 and a second portion 664. The first portion 662 may extend from the first end 652 into the body 656 and the second portion 664 may extend from the second end 654 into the body 656 until the second portion 664 engages the first portion 662. The first end 652 of the body 656 may also include a drive feature or engagement end 666, as shown in FIGS. 77, 78, and 82. The drive feature 666 may include, for example, at least one protrusion 668 and at least one recess 670. In the depicted embodiment, the drive feature 666 includes two protrusions 668 and two recesses 670, although other numbers of protrusions 668 and recesses 670 are also contemplated. The second end 654 may also include at least one cutting flute 672 recessed into the thread 658 and the body 656. As shown in FIG. 83, the second end 654 may include, for example, at least one cutting flute 672. The second member 650 may further include at least one groove or engagement channel 674 inset into the body 656 from the through hole 660, as shown in FIG. 77.

The coupling member or tension member 680, as shown in FIGS. 76-79 and 84-87, includes a first portion 682, a second portion 684, and at least one stop member 686 positioned between and coupled to the first portion 682 and the second portion 684. The first portion 682 extends from a first end of the coupling member 680 to the at least one stop member 686. The second portion 684 extends from a second end of the coupling member 680 to the at least one stop member 686. The first portion 682 may have, for example, a first diameter and a first length. The second portion 684 may have, for example, a second diameter and a second length. The at least one stop member 686 may have, for example, at least one third diameter and at least one third length. The first diameter may be, for example, the same size or a different size than the second diameter. The third diameter may be, for example, larger than the first and second diameters. In the depicted embodiment, the first length may be, for example, longer than the second length and the first and second lengths may be, for example, longer than the third length. Although shown as a solid member, it is also contemplated that the coupling member 680 may include, for example, a through hole or cannulation extending from the first end of the coupling member 680 to the second end of the coupling member 680.

The coupling member 680 may also include a proximal snap member 688 at the first end and a distal snap member 696 at the second end, as shown in FIGS. 76-79 and 84-87. The proximal snap member 688 may include at least one resilient member or deflecting member 690 extending away from the first portion 682 and at least one channel or groove 692. The at least one channel 692 may be positioned between the at least one resilient member 690. As shown in the depicted embodiment, the proximal snap member 688 may include, for example, four resilient members 690 and four channels 692 extending into the first portion 682 between the resilient members 690, although alternative combinations of resilient members 690 and channels 692 are also contemplated. In addition, each resilient member 690 may include at least one engagement tab or protrusion 694 positioned near the free end of the resilient member 690 opposite the end of the resilient member 690 coupled to the first portion 682. The distal snap member 696 may include at least one resilient member or deflecting member 698 extending away from the second portion 684 and at least one channel or groove 700. The at least one channel 700 may be positioned between the at least one resilient member 698. As shown in the depicted embodiment, the distal snap member 696 may include, for example, three resilient members 698 and three channels 700 extending into the second portion 684 between the resilient members 698, although alternative numbers of resilient members 698 and channels 700 are also contemplated. In addition, each resilient member 698 may include at least one engagement tab or protrusion 702 positioned near the free end of the resilient member 698 opposite the end of the resilient member 698 coupled to the second portion 684.

As shown in FIGS. 69-79 and 88-90, a first biasing member, activation member, retention clip, or spring clip 710 may have a first end 712 and a second end 714. The biasing member 710 may also include a body portion 716 at the first end 712. The body portion 716 may be, for example, rectangular shaped or another polygonal shape. The biasing member 710 may further include a first leg 720 and a second leg 724. The legs 720, 724 may be coupled to and extend away from a neck portion 718 of the body portion 716 to the second end 714 of the biasing member 710. The legs 720, 724 may be separated by a channel 728 extending into the biasing member 710 from the second end 714 to the neck portion 718. The outer or outward facing surfaces of the legs 720, 724 may be, for example, curved or rounded. The inner or inward facing surfaces of the legs 720, 724 are positioned adjacent to the channel 728 and may have, for example, relatively parallel sides to each other. The inner surface of the first leg 720 may also include, for example, a first groove 722 inset into the inner surface of the first leg 720. The inner surface of the second leg 724 may also include, for example, a second groove 726 inset into the inner surface of the second leg 724. The first and second grooves 722, 726 may be, for example, sized and shaped or configured to receive the coupling member 680.

Figure 91:
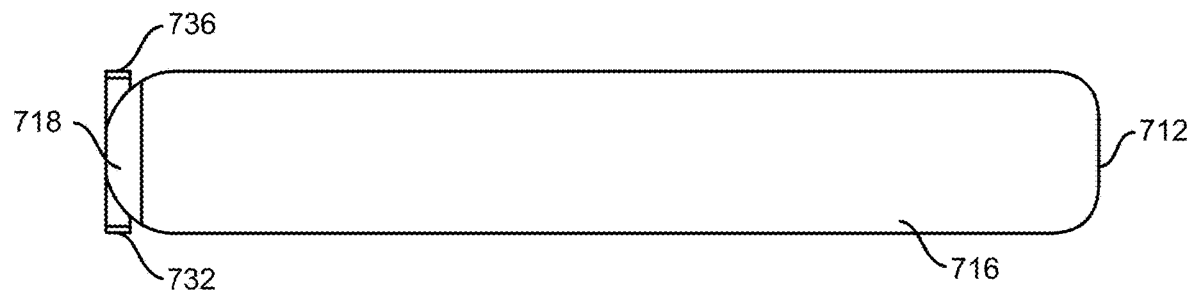
FIG. 91 is a top view of another retention clip of the implant system of FIG. 69, in accordance with an aspect of the present disclosure.
Figure 92:
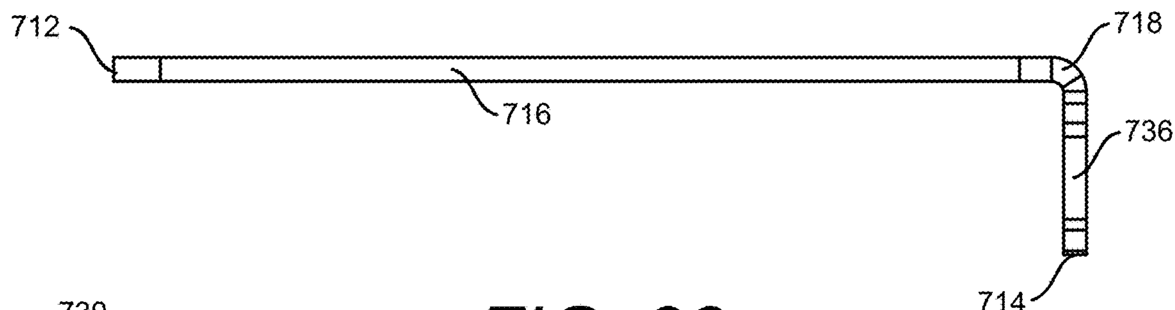
FIG. 92 is a side view of the retention clip of FIG. 91, in accordance with an aspect of the present disclosure.
Figure 93:
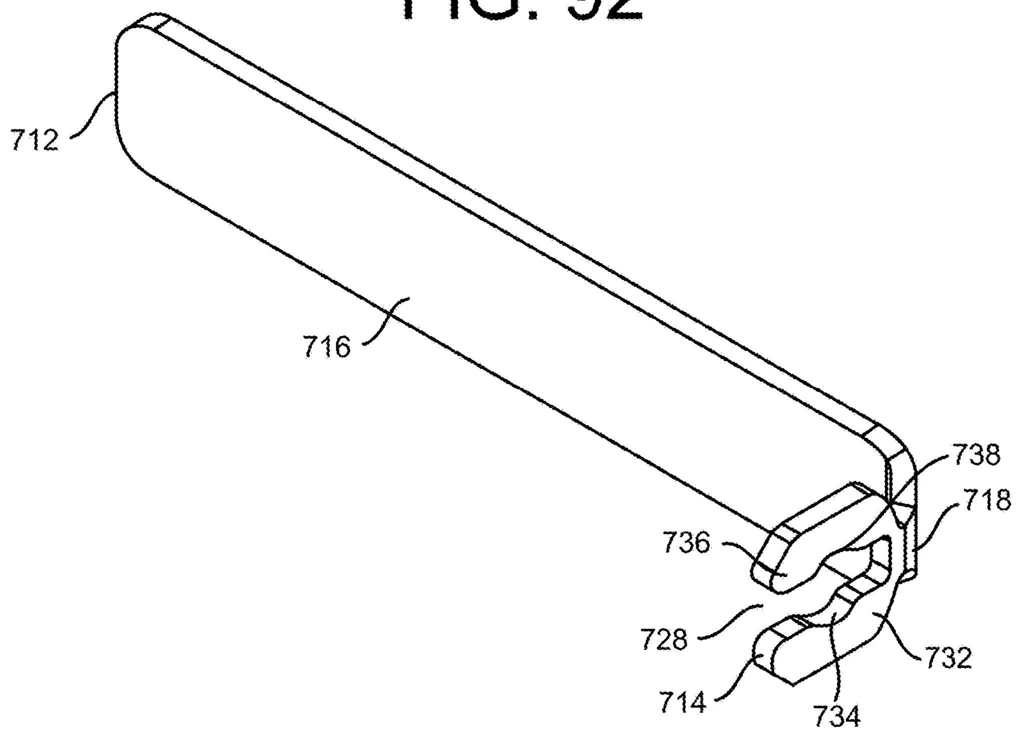
FIG. 93 is a perspective view of the retention clip of FIG. 91, in accordance with an aspect of the present disclosure.

Referring now to FIGS. 91-93, another biasing member, activation member, retention clip, or spring clip 730 is shown. The spring clip 730 may be similar to spring clip 710 and may have a first end 712 and a second end 714. The spring clip 730 may also include a body portion 716 at the first end 712. The body portion 716 may be, for example, rectangular shaped or another polygonal shape. The spring clip 730 may further include a first leg 732 and a second leg 736. The legs 732, 736 may be coupled to and extend away from a neck portion 718 of the body portion 716 to the second end 714 of the spring clip 730. The legs 732, 736 may be separated by a channel 728 extending into the spring clip 730 from the second end 714 toward the neck portion 718. The outer or outward facing surfaces of the legs 732, 736 may be, for example, curved or rounded. The inner or inward facing surfaces of the legs 732, 736 are positioned adjacent to the channel 728 and may have, for example, relatively parallel sides to each other. The inner surface of the first leg 732 may also include, for example, a first groove 734 inset into the inner surface of the first leg 732. The inner surface of the second leg 736 may also include, for example, a second groove 738 inset into the inner surface of the second leg 736. The first and second grooves 734, 738 may be, for example, sized and shaped or configured to receive the coupling member 680. The neck portion 718 of the spring clip 730 may be bent to place the body portion 716 at an angle with respect to the legs 732, 736. The angle of the neck 718 for the spring clip 730 may be, for example, approximately 90°.

Figure 112:
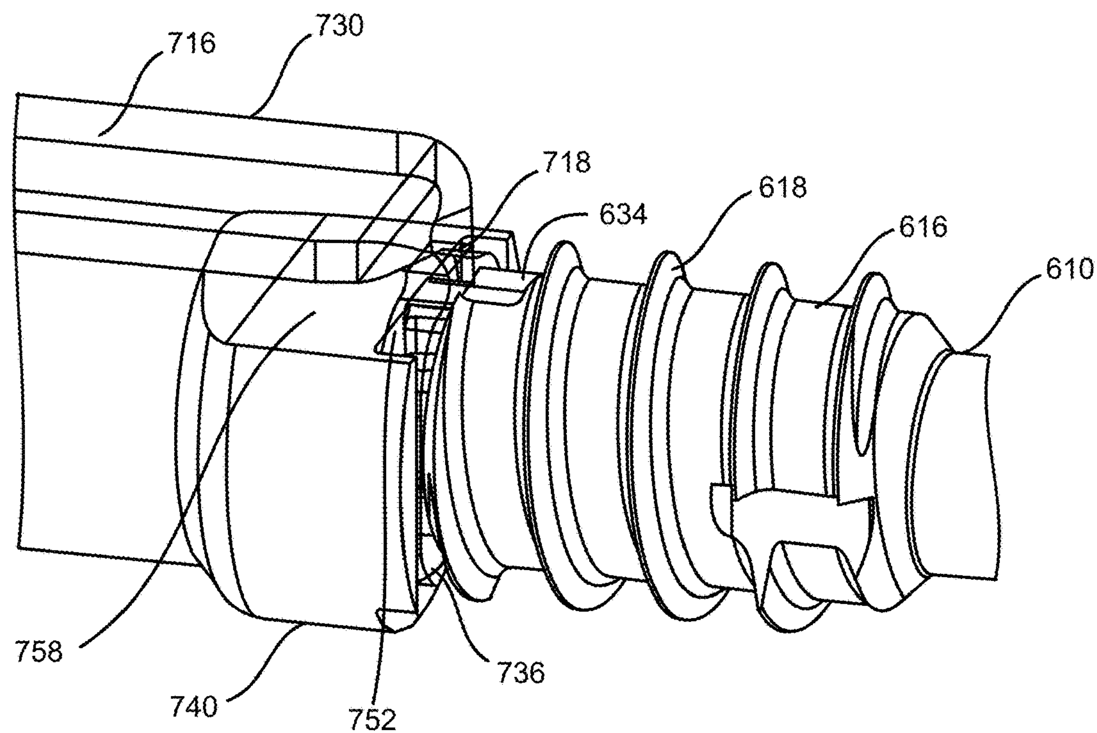
FIG. 112 is an enlarged, side perspective view of the retention clip of FIG. 91 and the proximal driver of FIG. 69 engaging the first member of FIG. 69, in accordance with an aspect of the present disclosure.
Figure 113:
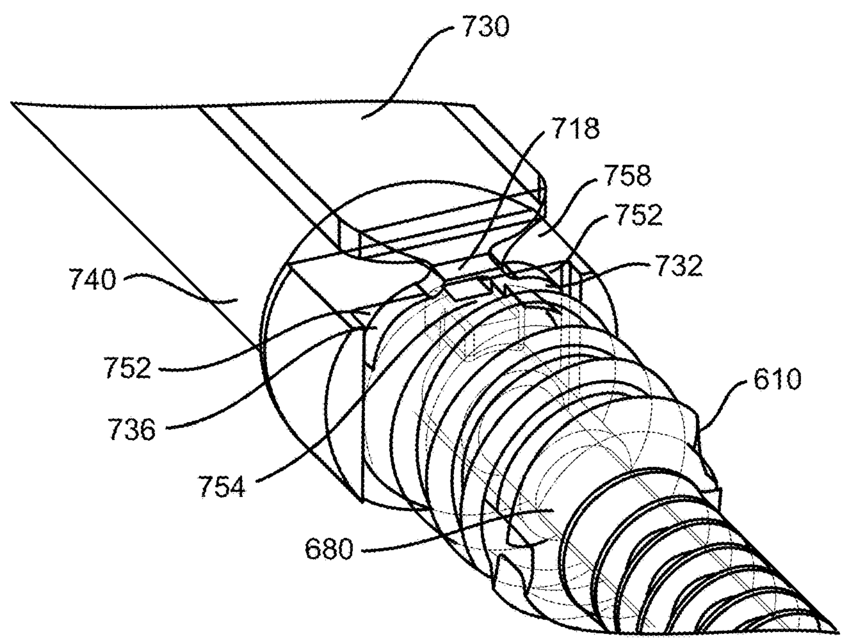
FIG. 113 is an enlarged, end perspective view of FIG. 112, in accordance with an aspect of the present disclosure.
Figure 117:
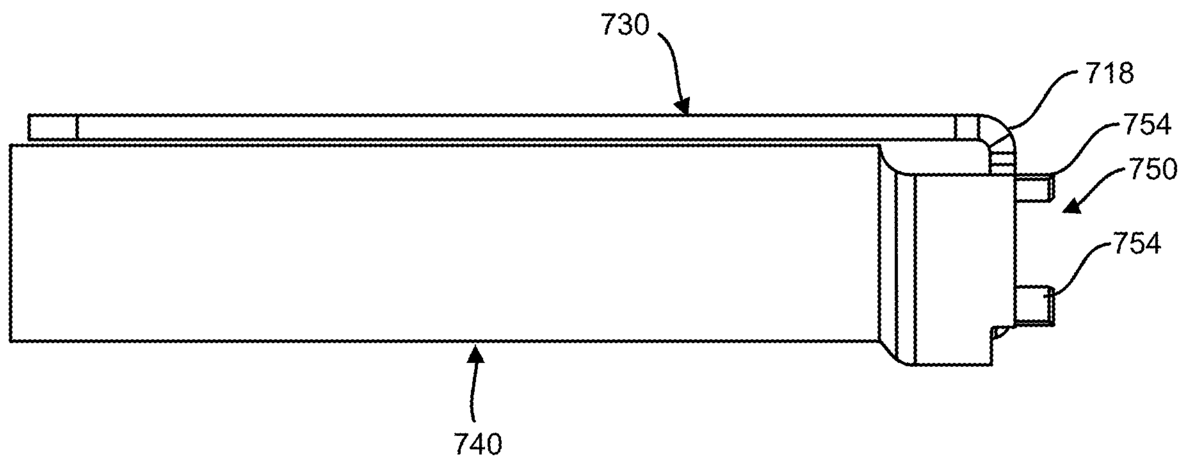
FIG. 117 is a side view of a proximal driver coupled with a retention clip of FIG. 91 positioned within the proximal driver, in accordance with an aspect of the present disclosure.
Figure 118:
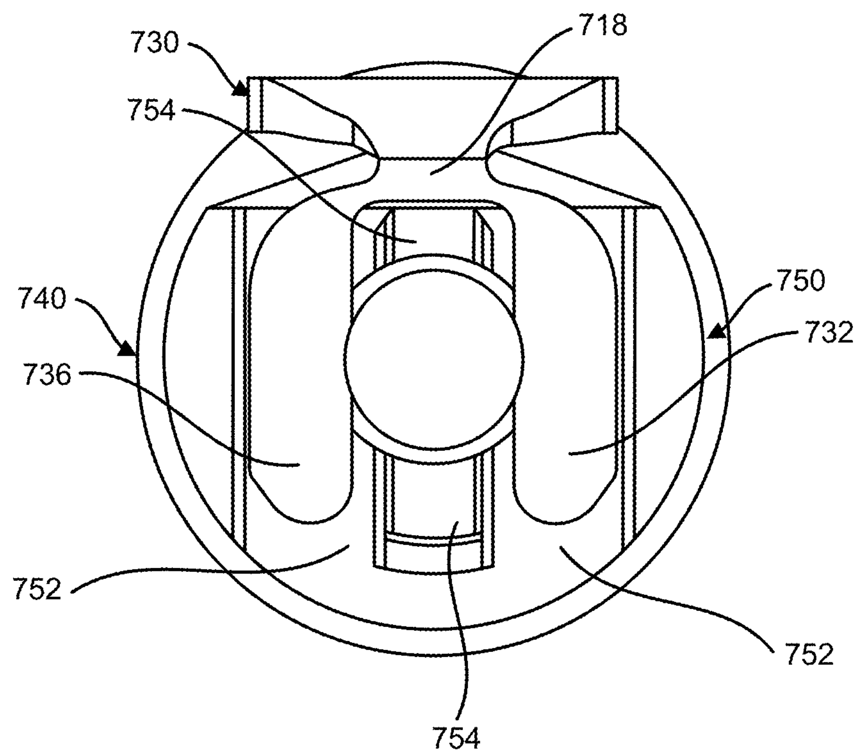
FIG. 118 is a first end view of the proximal driver and retention clip of FIG. 117, in accordance with an aspect of the present disclosure.
Figure 119:
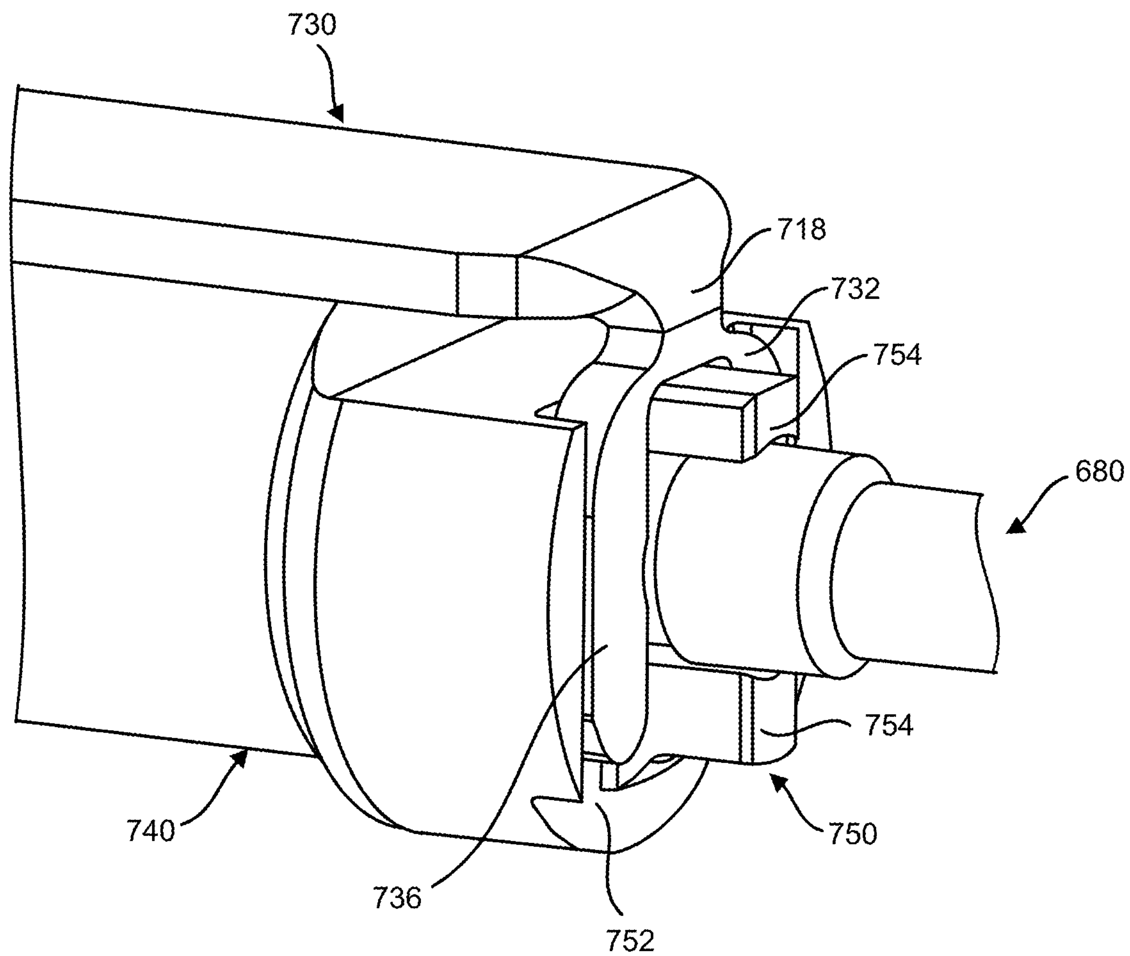
Figure 120:
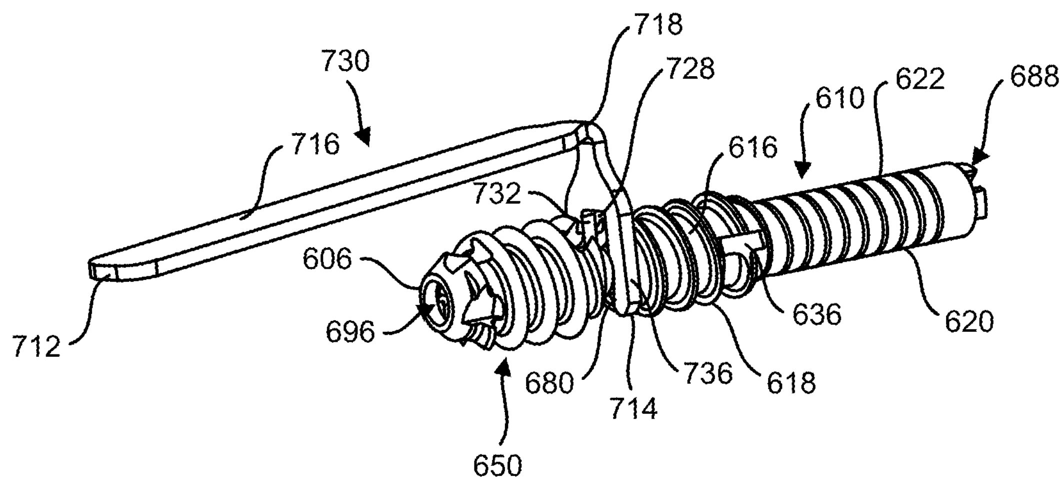
Figure 121:
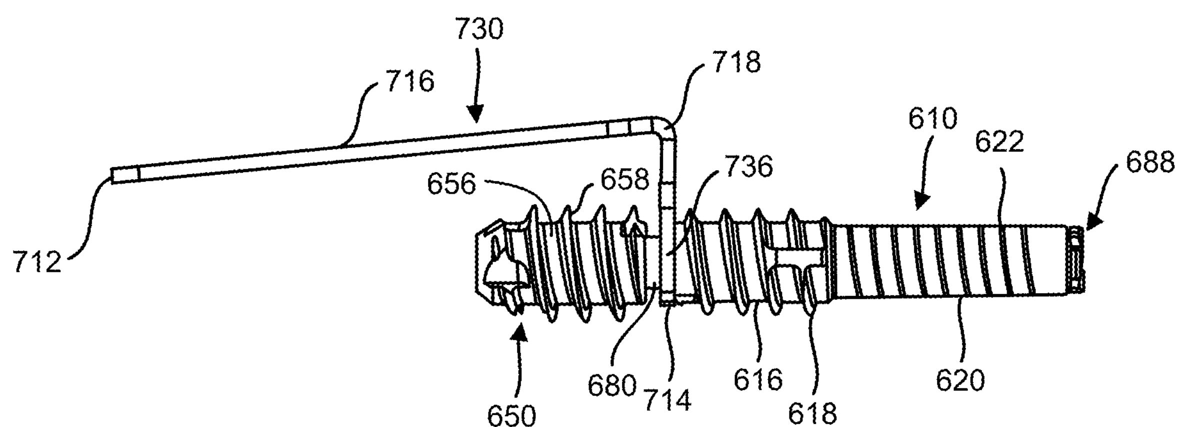

Another implant system 600 is shown in FIGS. 120-121. The implant system 600 includes the implant 602 and the retention clip 730. The body portion 716 of the retention clip 730 is bent at the neck portion 718 and extends over the second member 650. The body portion 716 may be, for example, bent to provide a low profile during insertion such that the body portion 716 may be position near or contact an exterior surface of the proximal driver 740, as shown in FIGS. 112-113. Thus, the body portion 716 may be bent, for example, approximately 90° relative to the legs 732, 736.

Referring now to FIG. 74, the implant 602 may be assembled by, for example, inserting the proximal snap member 688 of the coupling member 680 into the through hole 624 of the first member 610. The proximal snap member 688 may be inserted until the engagement tabs 694 engage the first end 612 of the first member 610 to secure the coupling member 680 to the first member 610. A spring clip 710, 730 may be inserted to engage the coupling member 680, for example, a portion between two stop members 686 of the coupling member 680. The spring clip 710, 730 may be, for example, inserted adjacent to at least one stop member 686 between the first portion 682 and second portion 684 of the coupling member 680 to tension the deformable member 620 of the first member 610 between at least one stop member 686 and the proximal snap member 688 of the coupling member 680. The second portion 684 of the coupling member 680 may be inserted into the through hole 660 of the second member 650. The distal snap member 696 may be inserted until the engagement tabs 702 are received within at least one groove 674 of the second member 650 or engage the second end 654 of the second member 650. Once the coupling member 680 is coupled to the first and second members 610, 650, the spring clip 710, 730 may be removed causing the deformable member 620 to apply a compressive force across any bone joint in which the first and second members 610, 650 are implanted. After the spring clip 710, 730 is removed, at least one stop member 686 may be, for example, positioned within the first portion 662 of the through hole 660 of the second member 650, the second portion 628 of the through hole 624 of the first member 610, or a distal stop member 686 positioned in the first portion 662 of the second member 650 and a proximal stop member 686 positioned in the second portion 628 of the first member 610.

Figure 94:
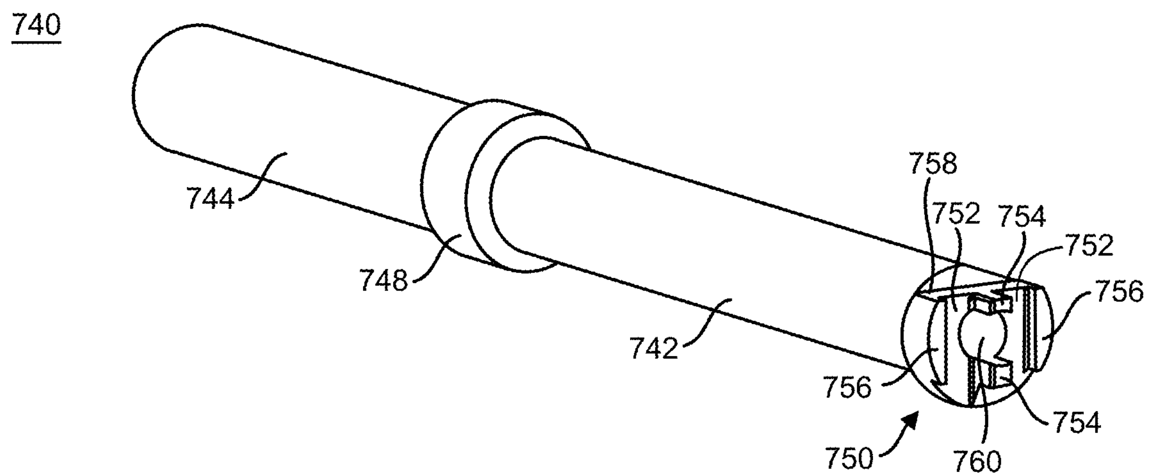
FIG. 94 is a first end perspective view of a proximal driver of the implant system of FIG. 69, in accordance with an aspect of the present disclosure.
Figure 95:
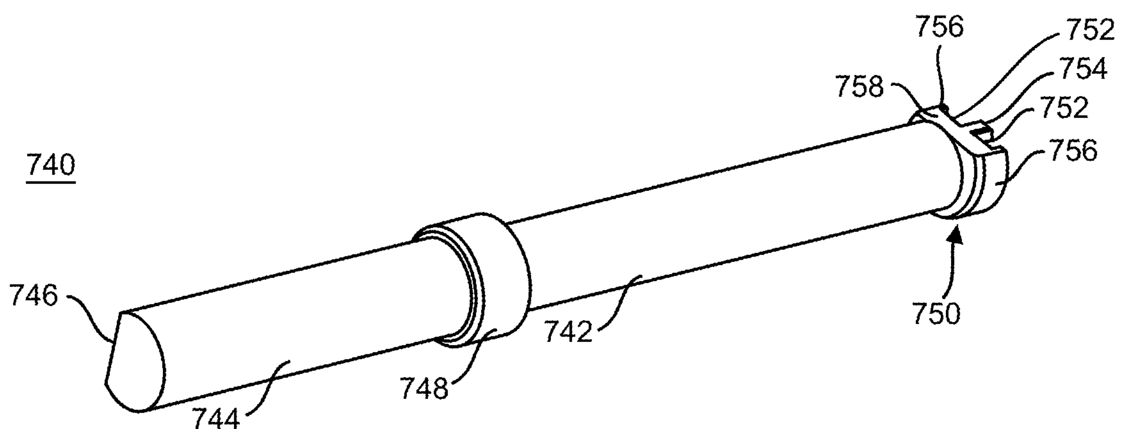
FIG. 95 is a second end perspective view of the proximal driver of FIG. 94, in accordance with an aspect of the present disclosure.
Figure 96:
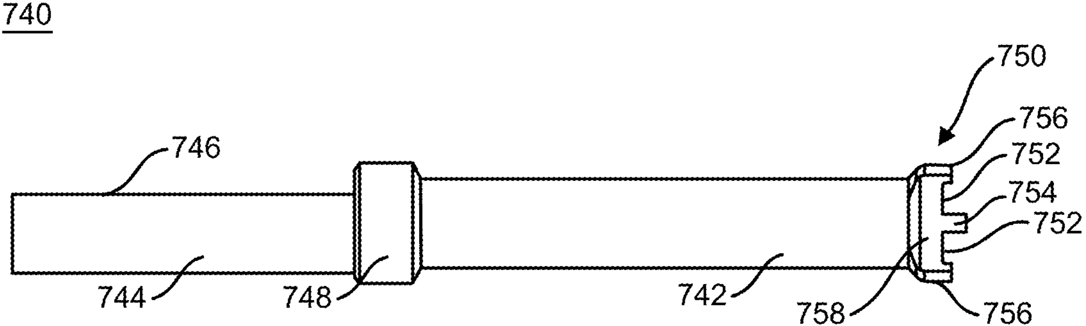
FIG. 96 is a top view of the proximal driver of FIG. 94, in accordance with an aspect of the present disclosure.
Figure 97:
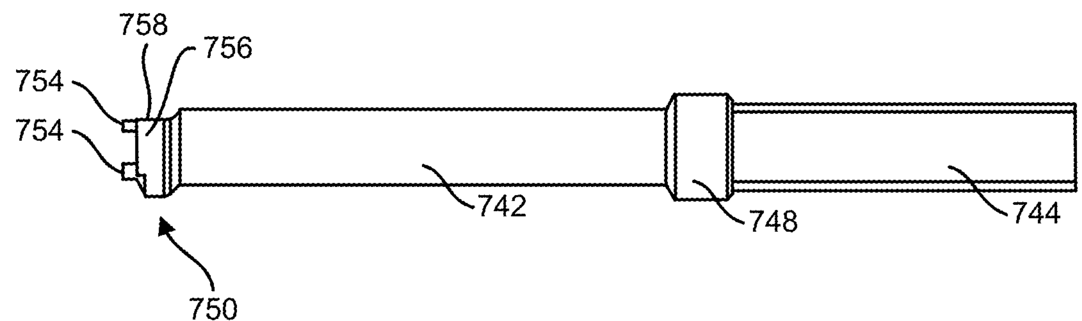
FIG. 97 is a first side view of the proximal driver of FIG. 94, in accordance with an aspect of the present disclosure.
Figure 98:
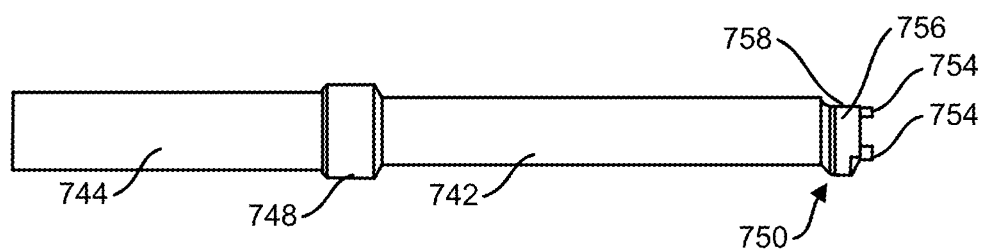
FIG. 98 is a second side view of the proximal driver of FIG. 94, in accordance with an aspect of the present disclosure.
Figure 99:
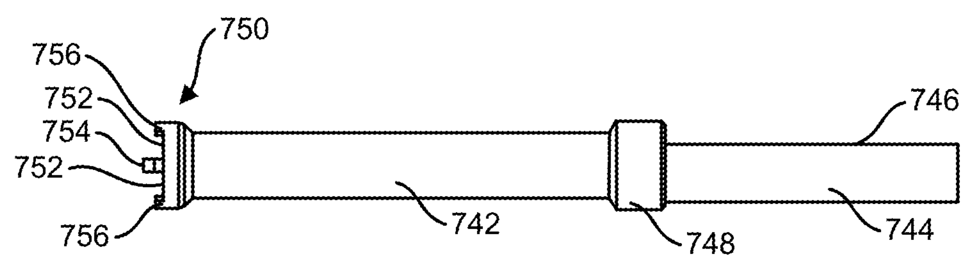
FIG. 99 is a bottom view of the proximal driver of FIG. 94, in accordance with an aspect of the present disclosure.
Figure 100:
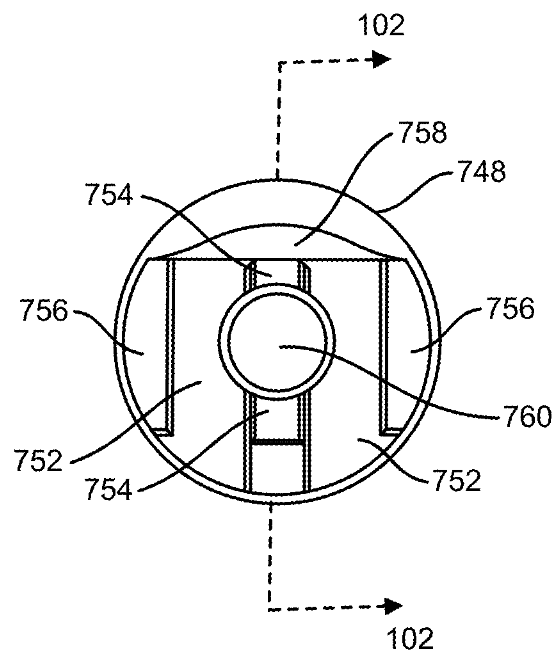
FIG. 100 is a first end view of the proximal driver of FIG. 94, in accordance with an aspect of the present disclosure.
Figure 101:
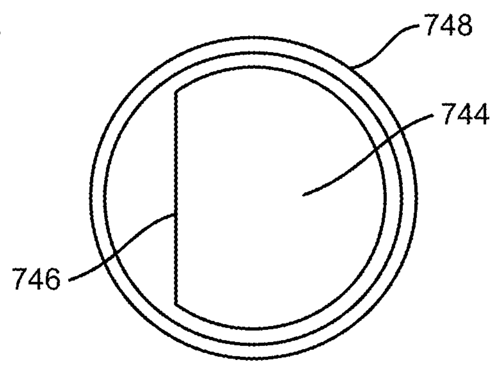
FIG. 101 is a second end view of the proximal driver of FIG. 94, in accordance with an aspect of the present disclosure.
Figure 102:
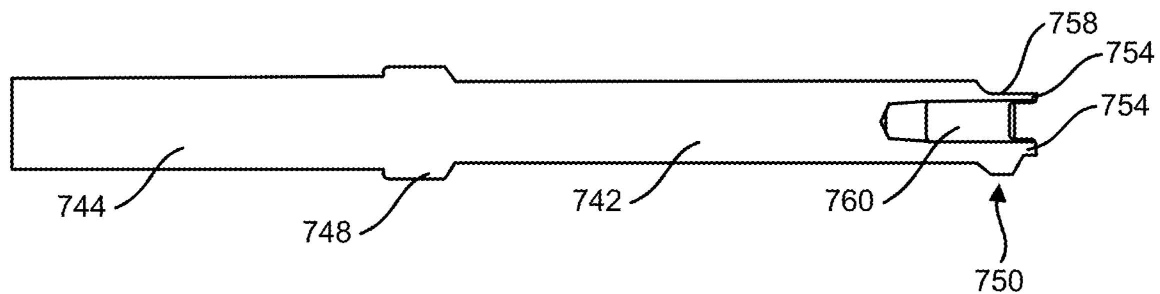
FIG. 102 is a cross-sectional view of the proximal driver of FIG. 94 taken along line 102-102 of FIG. 100, in accordance with an aspect of the present disclosure.
Figure 103:
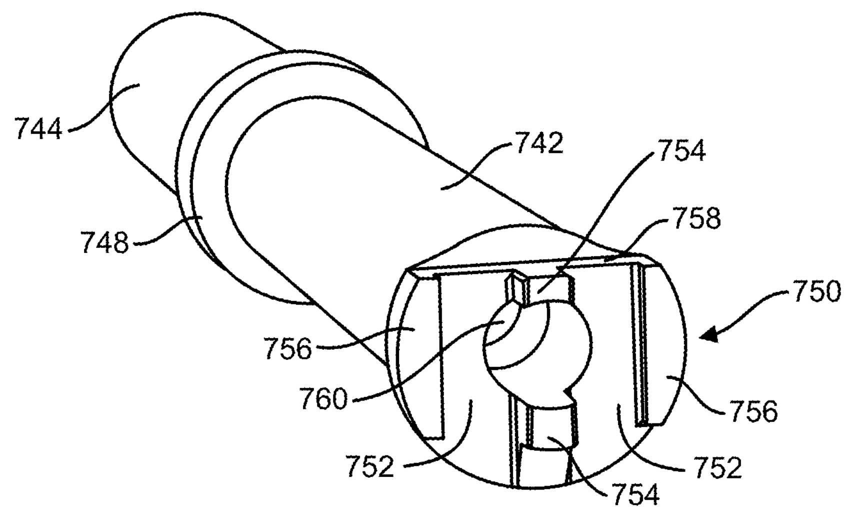
FIG. 103 is a perspective end view of the proximal driver of FIG. 94, in accordance with an aspect of the present disclosure.
Figure 104:
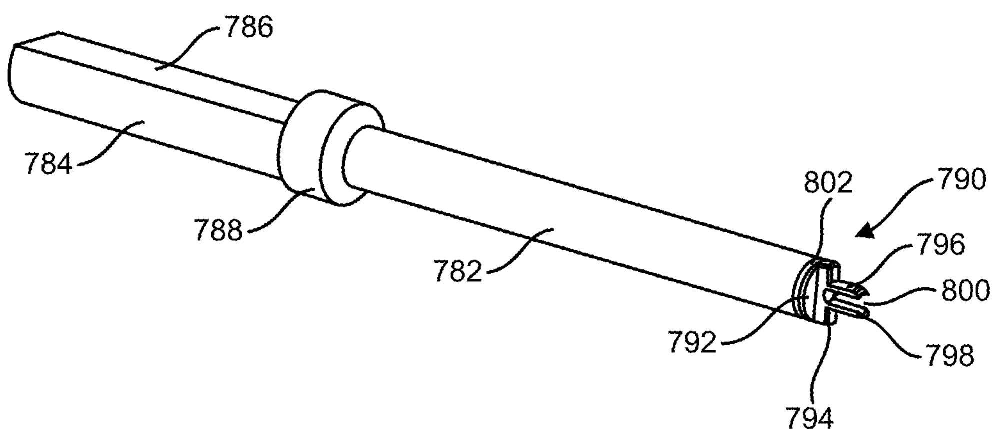
FIG. 104 is a first perspective view of a distal driver of the implant system of FIG. 69, in accordance with an aspect of the present disclosure.
Figure 105:
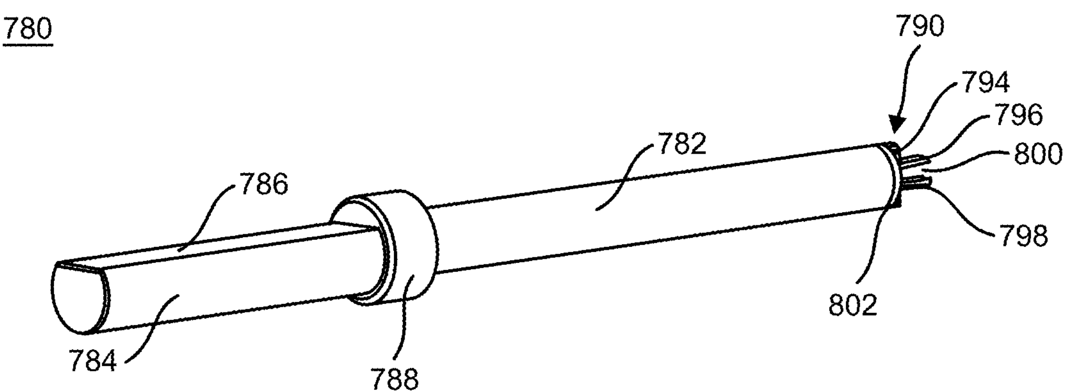
FIG. 105 is a second perspective view of the distal driver of FIG. 104, in accordance with an aspect of the present disclosure.
Figure 106:
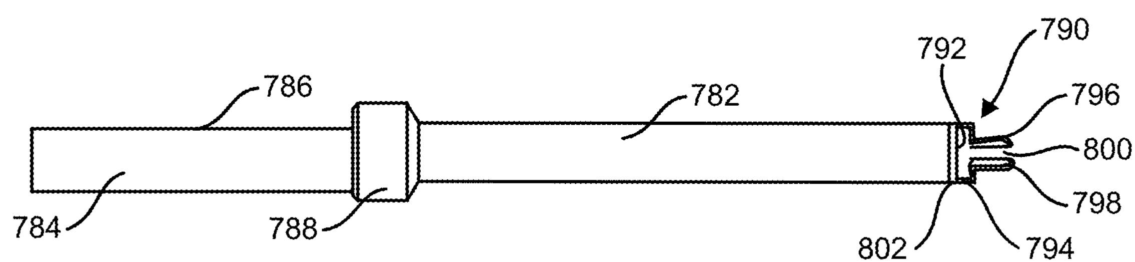
FIG. 106 is a top view of the distal driver of FIG. 104, in accordance with an aspect of the present disclosure.
Figure 107:
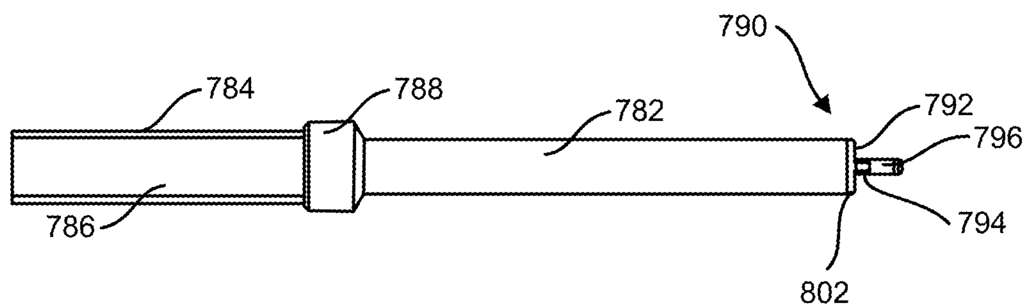
FIG. 107 is a side view of the distal driver of FIG. 104, in accordance with an aspect of the present disclosure.

The proximal driver or insertion tool 740 is shown in FIGS. 94-103 and 112, 113 and 117-119. The proximal driver 740 includes a body portion 742 at a first end, a tool engagement portion 744 at a second end, and a stop member 748 positioned between the body portion 742 and the tool engagement portion 744. The tool engagement portion 744 may include a flat surface or keyed surface 746 for insertion into a drill or driver tool (not shown) in a proper orientation. An engagement end 750 may be coupled to the body portion 742 at an end opposite the stop member 748 and tool engagement portion 744. The engagement end 750 may include at least one engagement channel 752. As shown in FIGS. 94, 100, and 103, the at least one engagement channel 752 is two engagement channels 752 extending parallel to each other. The two engagement channels 752 are separated by at least one protrusion 754. The at least one protrusion 754 may be, for example, two protrusions 754 as shown in the depicted embodiment. The two protrusion 754 may be, for example, asymmetrical allowing for the retention clip 730 to be bent over at a low profile while still maintaining or improving the strength of the driver 740. The two protrusions 754 are separated by an internal bore or opening 760 extending into the first end of the proximal driver 740 from the first end. The through hole or internal bore 760 receives the distal snap member 696 and may be, for example, tapered to deflect the deflecting members 698 and retain the coupling member 680 during insertion of the proximal member 610. The two engagement channels 752 each have a side member or side wall 756 positioned adjacent to the channels 752 on a side opposite the protrusions 754. The side walls 756 may, for example, allow the retention clip 710, 730 to rotate with the proximal driver 740, assist with preventing disengagement of the retention clip 710, 730, and assist with insertion of the proximal member 610. The proximal driver 740 may also include an alignment surface 758 extending perpendicular to the side walls 756 and channels 752. As shown in FIGS. 112, 113 and 117-119, the channels 752 are configured or sized and shaped to receive the legs 722, 724, 732, 736 of a retention clip 710, 730. The channels 752 form a recess between the protrusions 754 and the side walls 756 allowing for the legs 722, 724, 732, 736 of the retention clip 710, 740 to be flush with the end of the driver 740. In addition, the channels 752 serve as a depth stop. The protrusions 754 are configured or sized and shaped to engage the channel 728 of a retention clip 710, 730.

Referring now to FIGS. 104-111 and 114-116, the distal driver 780 is shown. The distal driver 780 includes a body portion 782 at a first end, a tool engagement portion 784 at a second end, and a stop member 788 positioned between the body portion 782 and the tool engagement portion 784. The tool engagement portion 784 may include a flat surface or keyed surface 786 for insertion into a drill or driver tool (not shown) in a proper orientation. The distal driver 780 may also include a drive feature 790 positioned on a first end of the body portion 782 on an end opposite the stop member 788 and tool engagement portion 784. The drive feature 790 may include an engagement end 792 with an engagement protrusion or alignment protrusion 794 extending away from the first end 792 of the body portion 782. The alignment protrusion 794 may extend across the diameter of the body portion 782 to have a length the same as the diameter of the body portion 782. In addition, the alignment protrusion 794 may have a width smaller than the diameter of the body portion 782 forming, for example, a rectangular or other polygonal shaped protrusion.

Figure 108:
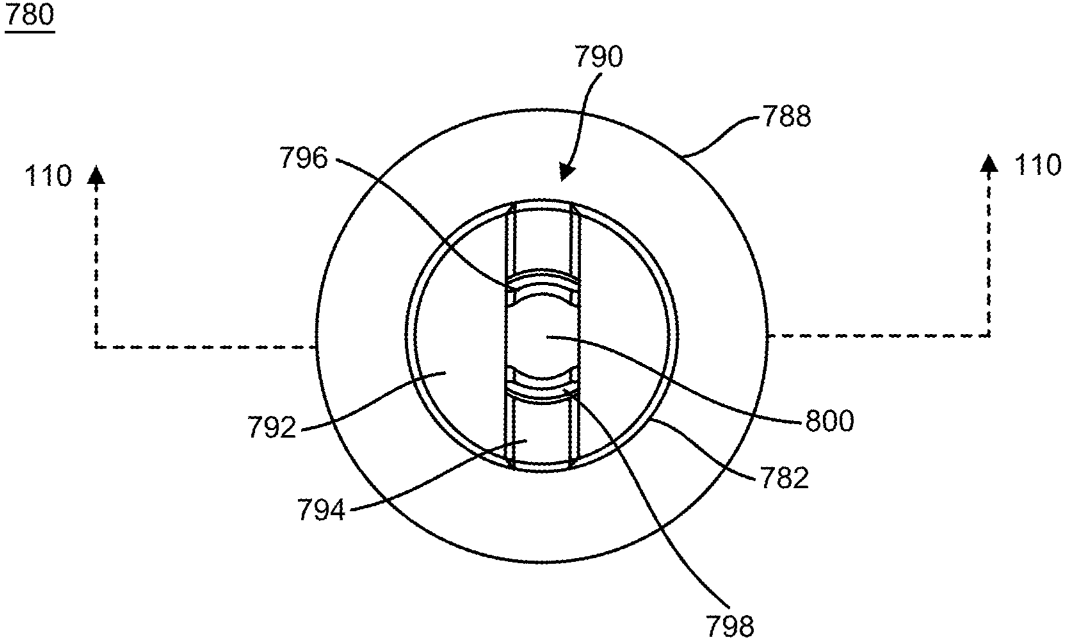
FIG. 108 is a first end view of the distal driver of FIG. 104, in accordance with an aspect of the present disclosure.
Figure 109:
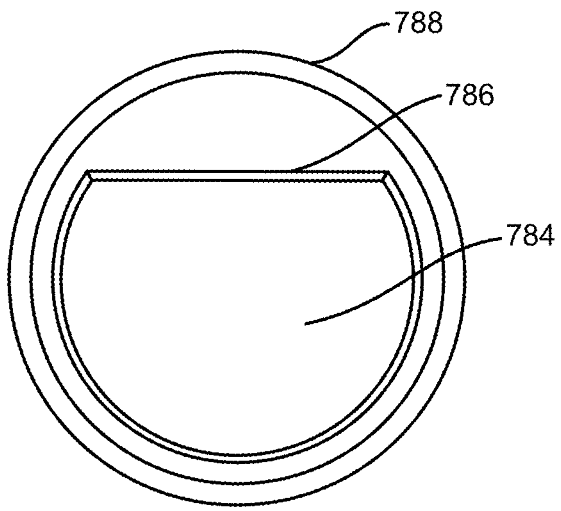
FIG. 109 is a second end view of the distal driver of FIG. 104, in accordance with an aspect of the present disclosure.
Figure 110:
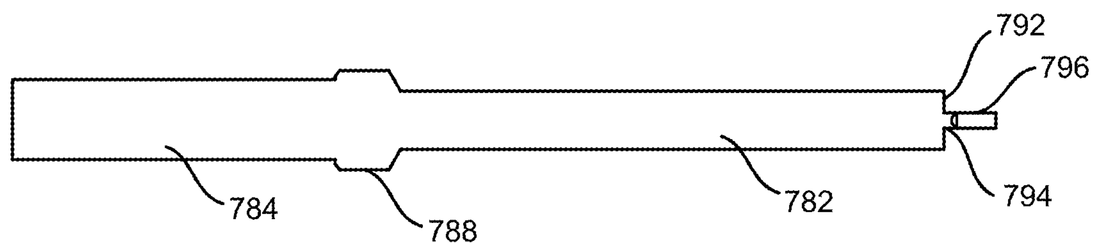
FIG. 110 is a cross-sectional view of the distal driver of FIG. 104 taken along line 110-110 in FIG. 108, in accordance with an aspect of the present disclosure.
Figure 111:
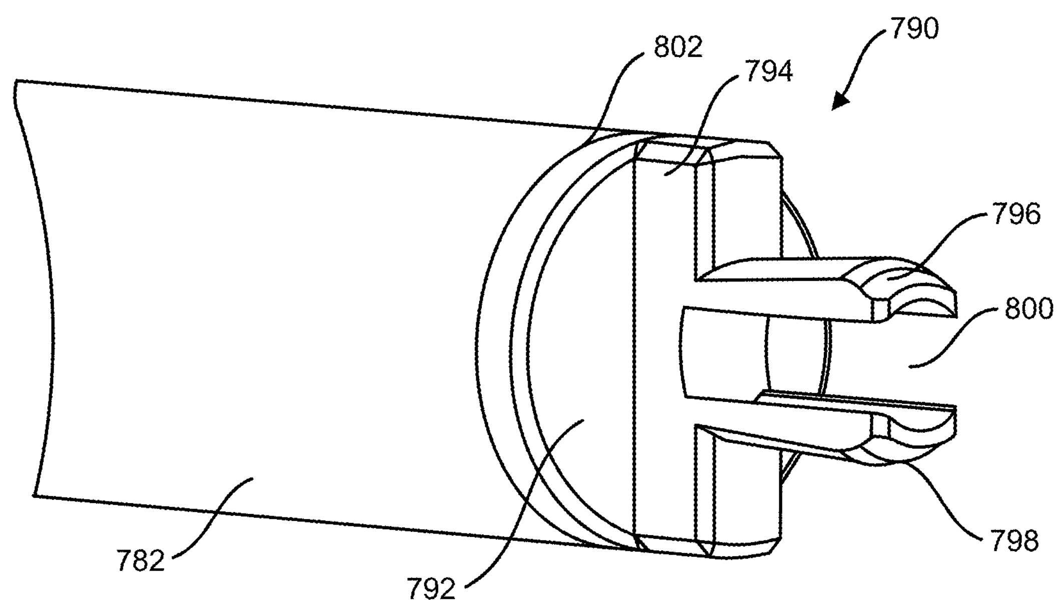
FIG. 111 is an enlarged view of the distal driver of FIG. 104, in accordance with an aspect of the present disclosure.

As shown in FIGS. 104-106, 108 and 111, the drive feature 790 may also include a first leg 796 and a second leg 798 extending out from or away from the alignment protrusion 794. The first leg 796 may be positioned adjacent to and spaced apart from the second leg 798 to form a channel 800 extending between the first leg 796 and the second leg 798 from a first end of the distal driver 780 to the alignment protrusion 794. The exterior surfaces of the first and second legs 796, 798 may be, for example, tapered as the legs 796, 798 extend from the first end or free end to the alignment protrusion 794 forming, for example, a tear drop shape. As shown in FIG. 108, the interior and exterior surfaces of the legs 796, 798 may be, for example, curved or arced. As shown in FIGS. 114 and 115, the alignment protrusion 794 is received within the recesses 670 of the distal member 650. Referring now to FIGS. 115 and 116, the legs 796, 798 are received within the second portion 664 of the distal member 650 to retain the distal member 650 during insertion. The distal driver 780 may also include, for example, at least one laser marking 802 along the length of the body portion 782, as shown in FIGS. 104-107. The at least one laser marking 802 may, for example, indicate the depth of insertion of the distal member 650.

A method of inserting an implant 602 using implant system 600 may include making an incision, for example, a longitudinal or transverse elliptical incision over the joint of the patient. Next, the method may include preparing and aligning the joint by using a saw or bone cutter to resect the cartilage at the head of the proximal phalanx. The cut may be made, for example, at the condyles to allow for passage of the implant 602 into the middle phalanx during insertion. The size of the implant 602 may be determined either pre-operatively using radiographic measurements or intra-operatively by visualizing the bone size. A retrograde k-wire technique may be used to assist with alignment and determining the final position of the toe. After the joint is prepared, the method may include bone preparation by drilling over the k-wires previously placed into the proximal and distal phalanx. Next, the distal member 650 may be inserted by distracting the distal portion of the toe distally and driving the distal member 650 into the drilled opening. The distal member 650 may be driven into the toe using the distal driver 780 and the driver 780 may be turned in, for example, a clockwise rotation until the distal member 650 is slightly buried below the head of the middle phalanx. The proximal member 610 may also be inserted by driving the proximal member 610 into the middle phalanx using, for example, the proximal driver 740. The proximal driver 740 may be, for example, rotated in a clockwise rotation until the head of the deformable member 620 is seated flush with the proximal phalanx head, i.e., when the retention clip 710, 730 is seated flush with the bone. Once the retention clip 710, 730 is flush with the bone, the proximal driver 740 is disengaged from the drive feature 630 of the proximal member 610 while remaining engaged with the retention clip 710, 730. Next, the retention clip 710, 730 is rotated using the proximal driver 740 until the neck 718 is positioned dorsal. When using retention clip 730 and with the proximal driver 740 still engaged with the retention clip 730, the body portion 716 may be bent dorsally into alignment with the legs 732, 736 to make the retention clip 730 linear. Once the retention clip 710, 730 is positioned dorsally and in a linear alignment between the body portion 716 and legs 720, 724, 732, 736, the proximal driver 740 may be disengaged from the retention clip 710, 730 and the proximal driver 740 removed from the surgical field leaving the retention clip 710, 730 coupled to the coupling member 680. Next, the distal portion of the toe may be translated dorsally to allow the coupling member 680 coupled to the proximal member 610 to be inserted into the distal member 650. While the retention clip 710, 730 is still coupled to the coupling member 680, ensure the proximal member 610 and the distal member 650 are mated with the coupling member 680. To ensure the members 610, 650 are mated the proximal and middle phalanges may be lightly distracted. Then, while bracing the proximal interphalangeal (PIP) joint, the retention clip 710, 730 may be removed allowing the deformable member 620 to deploy and allow for bone to bone apposition and compression across the joint. Finally, the soft tissue and incision may be closed.

As may be recognized by those of ordinary skill in the art based on the teachings herein, numerous changes and modifications may be made to the above-described and other embodiments of the present disclosure without departing from the scope of the disclosure. The components of the guides and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the guides and systems may include more or fewer components or features than the embodiments as described and illustrated herein. For example, the components and features of FIGS. 1-15, FIGS. 16-36, FIGS. 37-49, FIGS. 50-67, and FIGS. 69-119 may be used interchangeably and in alternative combinations as would be modified or altered by one of skill in the art. Specifically, the first members 110, 310, 510, 610, the second members 150, 350, 550, 650, the coupling members 180, 380, 580, 680, and the biasing members 410, 460, 710, 730 may be used in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. An implant system, comprising:

a first member;

a second member;

a coupling member with a first end and a second end, wherein the first end engages the first member and the second end engages the second member;

a proximal driver with an engagement end for coupling with the first member and a retention clip; and a distal driver with a drive feature for coupling with the second member, wherein the distal driver comprises:

a body portion; and an engagement portion at a first end of the body portion, wherein the engagement portion comprises:

a protrusion extending across a diameter of the body portion at the first end; and a drive feature extending away from the protrusion.

2. The implant system of claim 1, wherein the first member comprises:

a body portion with at least one thread positioned on an exterior surface of the body portion of the first member.

3. The implant system of claim 2, wherein the first member further comprises:

a deformable member coupled to the body portion.

4. The implant system of claim 3, wherein the deformable member further comprises:

a helical opening extending along at least a portion of a length of the deformable member, wherein the helical opening extends from an exterior surface of the deformable member into a through hole of the deformable member, wherein the through hole extends along a length of the deformable member.

5. The implant system of claim 3, wherein the body portion of the first member and the deformable member are integral.

6. The implant system of claim 2, wherein the body portion of the first member further comprises:

an engagement end positioned at a second end of the body portion of the first member.

7. The implant system of claim 6, wherein the engagement end comprises:

at least one protrusion extending away from the body portion of the first member; and at least one recess extending into the at least one protrusion.

8. The implant system of claim 1, wherein the first member further comprises:

a retaining member configured to engage the first end of the coupling member.

9. The implant system of claim 1, wherein the second member comprises:

a body;

at least one through hole extending through the body from a first end to a second end of the second member; and at least one thread positioned on an exterior surface of the body.

10. The implant system of claim 9, wherein the second member further comprises:

an engagement end positioned at the first end of the second member, wherein the engagement end of the second member comprises:

at least one protrusion extending away from the body; and at least one recess extending into the at least one protrusion.

11. The implant system of claim 10, wherein the second member further comprises:

at least one groove inset into an interior surface of the body, wherein the interior surface is formed by the at least one through hole of the second member.

12. The implant system of claim 1, wherein the coupling member comprises:

a first portion; and a second portion coupled to the first portion at an end, wherein the first portion extends from the first end of the coupling member toward the second portion, and the second portion extends from the second end of the coupling member toward the first portion.

13. The implant system of claim 12, wherein the coupling member further comprises:

at least one stop member with a first end and a second end, wherein the first end is proximate to the first portion and the second end is proximate to the second portion.

14. The implant system of claim 13, wherein the coupling member further comprises:

a proximal snap member positioned at the first end of the coupling member; and a distal snap member positioned at the second end of the coupling member.

15. The implant system of claim 14, wherein the proximal snap member comprises:

at least one engagement tab extending away from the first portion; and at least one groove extending partially into the first portion of the coupling member.

16. The implant system of claim 15, wherein the proximal snap member comprises:

four engagement tabs extending out from the first end of the coupling member; and four grooves positioned adjacent to the four engagement tabs and extending around a circumference of the coupling member.

17. The implant system of claim 16, wherein the distal snap member comprises:

at least one resilient member extending away from the second end of the coupling member; and at least one channel extending into the at least one resilient member.

18. The implant system of claim 17, wherein the distal snap member further comprises:

at least one engagement tab extending away from the at least one resilient member, wherein the at least one engagement tab is positioned at a free end of the at least one resilient member.

19. The implant system of claim 1, further comprising:

a biasing member positioned to engage the coupling member between the first member and the second member.

20. The implant system of claim 19, wherein the biasing member comprises:

a body portion positioned at a first end of the biasing member;

a first leg extending away from a bottom surface of the body portion of the biasing member to a second end of the biasing member, wherein the first leg is positioned on a first side of the body portion of the biasing member;

a second leg extending away from the bottom surface of the body portion of the biasing member to the second end of the biasing member, wherein the second leg is positioned on a second side of the body portion of the biasing member; and a channel extending from the second end into the biasing member between the first leg and the second leg.

21. The implant system of claim 20, wherein the biasing member further comprises:

a first groove extending into the first leg from the channel; and a second groove extending into the second leg from the channel;

wherein the first and second grooves are configured to receive the coupling member.

22. The implant system of claim 1, further comprising:

a biasing member positioned to engage the coupling member between the first member and the second member.

23. The implant system of claim 22, wherein the biasing member comprises:

a body portion positioned at a first end of the biasing member;

a first leg extending away from a bottom surface of the body portion of the biasing member to a second end of the biasing member, wherein the first leg is positioned on a first side of the body portion of the biasing member;

a second leg extending away from the bottom surface of the body portion of the biasing member to the second end of the biasing member, wherein the second leg is positioned on a second side of the body portion of the biasing member; and a channel extending from the second end into the biasing member between the first leg and the second leg.

24. The implant system of claim 23, wherein the biasing member further comprises:

a first groove extending into the first leg from the channel; and a second groove extending into the second leg from the channel;

wherein the first and second grooves are configured to receive the coupling member.

25. The implant system of claim 22, wherein the biasing member is a retention clip.

26. The implant system of claim 25, wherein the retention clip comprises:

a body portion;

a neck extending away from the body portion;

a first leg extending away from the neck on a side opposite the body portion;

a second leg extending away from the neck adjacent to the first leg; and a channel separating the first leg and the second leg.

27. The implant system of claim 26, wherein the retention clip further comprises:

a first groove recessed into an interior surface of the first leg; and a second groove recessed into an interior surface of the second leg.

28. The implant system of claim 27, wherein the retention clip is bent at the neck to position the first leg at an angle relative to the second leg.

29. The implant system of claim 26, wherein the first leg of the retention clip removably engages a first engagement channel and the second leg of the retention clip removably engages a second engagement channel.

30. An implant system, comprising:

a first member;

a second member;

a coupling member with a first end and a second end, wherein the first end engages the first member and the second end engages the second member;

a proximal driver comprising:

an engagement end for coupling with the first member, wherein the engagement end comprises:

a first engagement channel;

a second engagement channel positioned parallel to the first engagement channel; and at least one protrusion extending away from an end of the proximal driver and positioned between the first and second engagement channels;

a retention clip; and an internal bore for receiving the coupling member; and a distal driver with a drive feature for coupling with the second member.

31. The implant system of claim 30, wherein the first member comprises:

a body portion with at least one thread positioned on an exterior surface of the body portion.

32. The implant system of claim 31, wherein the first member further comprises:

a deformable member coupled to the body portion of the first member.

33. The implant system of claim 32, wherein the deformable member further comprises:

a helical opening extending along at least a portion of a length of the deformable member, wherein the helical opening extends from an exterior surface of the deformable member into a through hole of the deformable member, wherein the through hole extends along the length of the deformable member.

34. The implant system of claim 33, wherein the first member further comprises:

a retaining member configured to engage the first end of the coupling member.

35. The implant system of claim 34, wherein the body portion of the first member further comprises:

an engagement end positioned at a second end of the body portion of the first member.

36. The implant system of claim 35, wherein the engagement end of the first member comprises:

at least one protrusion extending away from the body portion of the first member; and at least one recess extending into the at least one protrusion.

37. The implant system of claim 36, wherein the second member comprises:

a body;

at least one through hole extending through the body from a first end to a second end of the second member; and at least one thread positioned on an exterior surface of the body.

38. The implant system of claim 37, wherein the second member further comprises:

an engagement end of the second member positioned at the first end of the second member, wherein the engagement end comprises:

at least one protrusion extending away from the body; and at least one recess extending into the at least one protrusion.

39. The implant system of claim 38, wherein the second member further comprises:

at least one groove inset into an interior surface of the body, wherein the interior surface is formed by the at least one through hole of the second member.

40. The implant system of claim 39, wherein the coupling member comprises:

a first portion; and a second portion coupled to the first portion at an end, wherein the first portion extends from the first end of the coupling member toward the second portion, and the second portion extends from the second end of the coupling member toward the first portion.

41. The implant system of claim 40, wherein the coupling member further comprises:

at least one stop member with a first end and a second end, wherein the first end is proximate to the first portion and the second end is proximate to the second portion.

42. The implant system of claim 41, wherein the coupling member further comprises:

a proximal snap member positioned at the first end of the coupling member; and a distal snap member positioned at the second end of the coupling member.

43. The implant system of claim 42, wherein the proximal snap member comprises:

at least one engagement tab extending away from the first portion; and at least one groove extending partially into the first portion of the coupling member.

44. The implant system of claim 43, wherein the proximal snap member comprises:

four engagement tabs extending out from the first end of the coupling member; and four grooves positioned adjacent to the four engagement tabs and extending around a circumference of the coupling member.

45. The implant system of claim 44, wherein the distal snap member comprises:

at least one resilient member extending away from the second end of the coupling member; and at least one channel extending into the at least one resilient member.

46. The implant system of claim 45, wherein the distal snap member further comprises:

at least one engagement tab extending away from the at least one resilient member, wherein the at least one engagement tab is positioned at a free end of the at least one resilient member.

47. The implant system of claim 46, wherein the body portion of the first member and the deformable member are integral.

48. The implant system of claim 30, wherein the at least one protrusion is two protrusions and the two protrusions are asymmetrical.

49. The implant system of claim 48, wherein the two protrusions are separated by the internal bore.

50. The implant system of claim 30, wherein the internal bore is tapered along a length of the internal bore.

51. The implant system of claim 30, wherein the distal driver comprises:

a body portion; and an engagement portion at a first end of the body portion of the distal driver, wherein the engagement portion comprises:

a protrusion extending across a diameter of the body portion of the distal driver at the first end; and a drive feature extending away from the protrusion.

52. The implant system of claim 51, wherein the drive feature comprises:

a first leg extending out from the protrusion; and a second leg extending out from the protrusion and spaced apart from the first leg;

wherein the first and second legs taper as the first and second legs extend from a free end to the protrusion.

53. The implant system of claim 52, wherein an exterior surface of the first leg is curved and wherein an exterior surface of the second leg is curved.

54. The implant system of claim 30, wherein the distal driver comprises:

a body portion; and an engagement portion at a first end of the body portion of the distal driver, wherein the engagement portion comprises:

a protrusion extending across a diameter of the body portion of the distal driver at the first end; and a drive feature extending away from the protrusion, wherein the drive feature comprises:

a first leg extending out from the protrusion; and a second leg extending out from the protrusion and spaced apart from the first leg;

wherein the first and second legs taper as the first and second legs extend from a free end to the protrusion; and wherein the drive feature engages at least one through hole of the second member.

55. A method for using an implant, comprising:

obtaining the implant, wherein the implant comprises:

a first member;

a second member; and a coupling member with a first end and a second end;

making an incision to expose a joint with a first bone and a second bone;

preparing the first and second bones for receiving the implant;

inserting the second member into the first bone;

inserting the first end of the coupling member into the first member, comprising:

inserting the first end of the coupling member into a screw portion of the first member;

inserting the first end of the coupling member into a deformable member of the first member; and engaging a retaining member of the first member with the first end of the coupling member to secure the screw portion and the deformable member onto the coupling member;

inserting a retention clip to engage the coupling member;

inserting the first member with the engaged coupling member into the second bone;

inserting the second end of the coupling member into the second member;

removing the retention clip from engagement with the coupling member; and closing the incision.

56. The method of claim 55, wherein the first bone is a middle phalanx and the second bone is a proximal phalanx.

* * * * *

UNITED STATES PATENT AND TRADEMARK OFFICE

CERTIFICATE OF CORRECTION

PATENT NO. : 10,772,733 B2
APPLICATION NO. : 16/519270
DATED : September 15, 2020
INVENTOR(S) : Lintula et al.

It is certified that error appears in the above-identified patent and that said Letters Patent is hereby corrected as shown below:

In the Claims

Column 26, Line 38: Claim 19, Delete “claim 1” and insert -- claim 18 --

Signed and Sealed this
Tenth Day of November, 2020

Andrei Iancu
*Director of the United States Patent and Trademark Office*